US006274312B1

(12) United States Patent
Gish et al.

(10) Patent No.: US 6,274,312 B1
(45) Date of Patent: Aug. 14, 2001

(54) INTRACELLULAR REGULATORY MOLECULES; RELATED REAGENTS

(75) Inventors: Kurt C. Gish, Sunnyvale; Wolfgang Seghezzi; Frances Shanahan, both of Mountain View; Emma M. Lees, San Francisco; Terrill K. McClanahan, Sunnyvale, all of CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 08/999,774

(22) Filed: Dec. 10, 1997

Related U.S. Application Data

(60) Provisional application No. 60/032,818, filed on Dec. 11, 1996.

(51) Int. Cl.[7] .............................. C12Q 1/68; C07H 21/04; C12P 21/06; C12N 15/00

(52) U.S. Cl. ........................... 435/6; 536/23.2; 536/23.5; 435/69.1; 435/252.3; 435/325; 435/320.1

(58) Field of Search ............................... 435/69.1, 320.1, 435/325, 252.3, 6; 536/23.5

(56) References Cited

U.S. PATENT DOCUMENTS

| 5,449,755 | 9/1995 | Roberts et al. ...................... 530/350 |
| 5,543,291 | 8/1996 | Keyomarsi et al. .................... 435/6 |

FOREIGN PATENT DOCUMENTS

| WO 97/08433 | 3/1997 | (WO) . |
| WO 97/18333 | 5/1997 | (WO) . |
| WO 98/39448 | 9/1998 | (WO) . |

OTHER PUBLICATIONS

Harris et al., swis=prot38 Database, accession No. Q10178, Oct. 1996.*
Wilson et al., Nature, 368, 32–38, Mar. 1994.*
Hillier et al., Embl database, Accession no. N25983, Dec. 1995.*
Miyamoto et al., genbank database, Accession No.Accession No. D84487, Apr. 1996.*
Database DGENE, Last updated Mar. 19, 1999, Result from sequence search using Human p150 (SEQ ID No.:2) as the query and citing Accession Numbers: 98P–W56163, 95P–R80191, 87P–P70709, 96P–R95242, 95P–R74201, 96P–R98523, 98P–W48267, 96P–W05400, 95P–R73029, 93P–R40227, 98P–W31554, 92P–R22675, 98PW68207, 97P–W16337, 97P–W01787, 95P–R70491, 96P–R97866, 96P–W03627, 96P–W03626, 97P–W30763, 97P–W18317, 97P–W18317, 95P–R76640, 95P–R76640; Derwent Information Ltd., London.
Database DGENE, Last updated May 16, 1999, Result from sequence search using Human p130 (Seq ID No.:4) as the query; Derwent Information Ltd., London.
Database DGENE, Last updated Mar. 19, 1999, Result from sequence search using Partial Human p130 (Seq Id No.:4) as the query and citing Accession Numbers: 94P–R54202, 99P–W89951, 98P–W73121, 98P–W73120, 98P–W73119, 99P–W86313, 91P–R12534, 90P–R07670, 92P–R26049, 97P–W26726; Derwent Information Ltd., London.
Database DGENE, Last updated Mar. 19, 1999, Result from sequence search using Human VCP (Seq ID No.:6) as the query and citing Accession Numbers: 98P–W74883, 98P–W53457, 96P–W07873, 93P–R41727, 98P–W64559, 98P–W75006, 98P–W37959, 97P–W25639, 97P–W25635, 97P–W55684, 96P–R97282, 98P–W80620, 98P–W38478, 98P–W75006, 19P–W32324, 98P–W64459, 98P–W80620, 97P–W55684, 94P–R53529, 97P–W31867, 96P–W01102, 96P–W01101, 93P–R43580, 98P–W46462; Derwent Information Ltd., London.
Database DGENE, Last updated Mar. 19, 1999, Result from sequence search using Human tsg101 (Seq ID No.:8) as the query and citing Accession Numbers: 97P–W19111, 97P–W19110, 90P–R03928, 97P–W19604, 96P–W01464, 97P–W14517, 96P–W03758, 93P–R4123; Derwent Information Ltd., London.
Database DGENE, Last updated Mar. 19, 1999, Result from sequence search using Human KWC02 (Seq ID No.:10) as the query and citing Accession Numbers: 96P–R99426, 98P–W38426, 96P–R99427, 93P–R44217, 90P–R05369, 98P–W74784, 98P–W57403, 97P–W18098, 97P–W18094; Derwent Information Ltd., London.
Wei–Chun Au, et al., *Proc. Natl. Acad. Sci. U.S.A.*, 92:11657–11661, Dec. 5, 1995. "Identification of a member of the interferon regulatory factor family that binds to the inteferon–stimulated response element and activates expression of inteferon–induced genes".
W.C. Au, et al., *GenBank*, Accession No. Z56281, Mar. 29, 1996. Definition: "H. sapiens mRNA for interferon regulatory factor 3".
M. Egerton, et al.,*EMBO Journal*, 11(10):3533–3540, 1992. "VCP, the mammalian homolog of cdc48, is tyrosine phosphorylated in response to T cell antigen receptor activation".
Kai–Uwe Fröhlich, et al., *J. Cell Biology*, 114(3):443–453, Aug. 1991. "Yeast Cell Cycle Protein CDC48p Shows Full–Length Homology to the Mammalian Protein VCP and Is a Member of a Protein Family Involved in Secretion, Peroxisome Formation, and Gene Expression".

(List continued on next page.)

*Primary Examiner*—Rebecca E. Prouty
*Assistant Examiner*—M. Monshipouri
(74) *Attorney, Agent, or Firm*—Edwin P. Ching; Sheela Mohan-Peterson; Gerald P. Keleher

(57) ABSTRACT

Purified genes encoding intracellular regulatory molecules from a human, reagents related thereto including purified proteins, specific antibodies, and nucleic acids encoding these molecules are provided. Methods of using said reagents and diagnostic kits are also provided.

9 Claims, No Drawings

OTHER PUBLICATIONS

Caroline E. Grant, et al., *Nucleic Acids Research*, 23(12):2137–2146, 1995. "cIRF–3, a new member of the interferon regulatory factor (IRF) family that is rapidly and transiently induced by dsRNA".

C.E. Grant, et al., *GenBank*, Accession No. U20338, Feb. 9, 1996. Definition: "Gallus gallus interferon regulatory factor 3 (cIRF–3) mRNA, complete cds".

A. Grossman, et al., *GenBank*, Accession No. U73036, Oct. 21, 1996. Definition: "interferon regulatory factor 7 (humirf7) mRNA, complete cds.".

A. Grossman, et al., *GenPept*, Accession No. 1621457, Oct. 11, 1996. Definition: "interferon regulatory factor 7".

A Grossman, et al., *GenBank*, Accession No. U51127, Apr. 4, 1996. Definition: "Human interferon regulatory factor 3 (Humirf5) mRNA, complete cds".

L. Hillier, et al., *GenBank*, Accession No. H20148, Jul. 3, 1995. Definition: "yn56f05.s1 Homo sapiens cDNA clone 172449 3'".

L. Hillier, et al., *GenBank*, Accession No. N52794, Feb. 15, 1996. Definition: "yz18f06.s1 Homo sapiens cDNA clone 283427 3'".

L. Hillier, et al., *GenBank*, Accession No. N57616, Feb. 22, 1996. Definition: "yz18f06.r1 Soares_multiple_sclerosis_2NbHMSP Homo sapiens cDNA clone 283427 5', mRNA sequence".

L. Hillier, et al., *GenBank*, Accession No. R47967, May 18, 1995. Definition: "yj63b03.s1 Soares breast 2NbHBst Homo sapiens cDNA clone 153389 3', mRNA sequence".

Robert E. Kingston, et al., *Genes and Development*, 10:905–920, 1996. "Repression and activation by multiprotein complexes that alter chromatin structure".

Kerry J. Koller and Michael J. Brownstein, *Nature*, 325:542–545, Feb. 5, 1987. "Use of a cDNA clone to identify a supposed precursor protein containing valosin".

Limin Li and Stanley N. Cohen, et al., *Cell*, 85:319–329, May 3, 1996. "tsg101: A Novel Tumor Susceptibility Gene Isolated by Controlled Homozygous Functional Knockout of Allelic Loci in Mammalian Cells".

Limin Li, et al., *Cell*, 88:143–154, Jan. 10, 1997. "The TSG101 Tumor Susceptibility Gene Is Located in Chromosome 11 Band p15 and Is Mutated in Human Breast Cancer".

Alexandre Maucuer, et al., *Proc. Natl. Acad. Sci. U.S.A.*, 92:3100–3104, Apr. 11, 1995. "Stathmin interaction with a putative kinase and coiled–coil–forming protein domains".

Nancy Nelson, et al., *Journal of Immunology*, 156(10)3711–3720, May 15, 1996. "Expression of IFN Regulatory Factor Family Proteins in Lymphocytes Induction of Stat–1 and IFN Consensus Sequence Binding Protein Expression by T Cell Activation".

Craig L. Peterson and Ira Herskowitz, *Cell*, 68:573–583, Feb. 7, 1992. "Characterization of the Yeast SWI1, SWI2, and SWI3 Genes, Which Encode a Global Activator of Transcription".

W.E. Schmidt, et al., *GenPept*, Accession No. 2144498, Mar. 13, 1997. Definition: "transition endoplasmic reticulum ATPase—pig".

Roberta J. Schulte, et al., *Journal of Immunology*, 153:5465–5472, 1994. "Tyrosine Phosphorylation of VCP, the Mammalian Homologue of the *Saccharomyces cerevisiae* CDC48 Protein, Is Unusually Sensitive to Stimulation by Sodium Vanadate and Hydrogen Peroxide".

Tadatsugu Taniguchi, et al., *J. Cancer Res. Clin. Oncol.*, 121(9–10):516–520, 1995. "Regulation of the interferon system and cell growth by the IRF transcription factors".

Weidong Wang, et al., *Genes and Development*, 10:2117–2130, 1996. "Diversity and specialization of mammalian SWI/SNF complexes".

W. Wang, et al., *GenBank*, Accession No. U66615, Sep. 18, 1996. Definition: "Human SWI/SNF complex 155KDa subunit (BAF155) mRNA, complete cds.".

Anat Weisz, et al., *J. Biol. chem.*, 267(35):25589–25596, Dec. 15, 1992. Human Interferon Consensus Sequence Binding Protein Is a Negative Regulator of Enhancer Elements Common to Interferon–Inducible Genes.

J. Fernando Bazan, *Science*, 257:410–413, Jul. 17, 1992. "Unraveling the Structure of IL–2".

J. Fernando Bazan, *Immunology Today*, 11(10):350–354, 1990. "Haemopoietic and helical cytokines".

Göran Brattsand, et al., *European Journal of Biochemistry*, 220:359–368, 1994. "Cell–cycle–regulated phosphorylation of oncoprotein 18 on Ser 16, Ser 25 and Ser 38".

Bruce A. Edgar and Christian F. Lehner, *Science*, 274:1646–1652, Dec. 6, 1996. "Developmental Control of Cell Cycle Regulators: A Fly's Perspective".

Sephen J. Elledge, *Science*, 274:1664–1672, Dec. 6, 1996. "Cell Cycle Checkpoints: Preventing an Identity Crisis".

David P. Gearing and David Cosman, *Cell*, 66:9–10, Jul. 12, 1991. "Homology of the p40 Subunit of Natural Killer Cell Stimulatory Factor (NKSF) with the Extracellular Domain of the Interleukin–6 Receptor".

Karen A. Heichman and James M. Roberts, *Cell*, 79:557–562, Nov. 18, 1994. "Rules to Replicate By".

L. Hillier, et al., *GenBank*, Accession No. N90895, Apr. 3, 1996. Definition: "zb20h08.s1 Soares fetal lung NbHL19W Homo sapiens cDNA clone 302655 3' similar to contains element PTR7 repetitive element;, mRNA sequence.".

L. Hillier, et al., *GenBank*, Accession No. R89324, Aug. 24, 1995. Definition: "yq01d02.s1 Homo sapiens cDNA clone 195651 3'.".

L. Hillier, et al., *GenBank*, Accession No. R96476, Aug. 24, 1995. Definition: "yq37h11.s1 Homo sapiens cDNA clone 198021 3'.".

L. Hillier, et al., *GenBank*, Accession No. T79440, Mar. 15, 1995. Definition: "yd75e02.s1 Homo sapiens cDNA clone 114074 3?.".

Deborah T. Hung, et al., *Chemistry & Biology*, 3:623–639, Aug. 1996. "Understanding and controlling the cell cycle with natural products".

Randall W. King, et al., *Science*, 274:1652–1659, Dec. 6, 1996. "How Proteolysis Drives the Cell Cycle".

Emma Lees, *Current Opinion in Cell Biology*, 7:773–780, 1995. "Cyclin dependent kinase regulation".

Kim Nasmyth, *Science*, 274:1643–1645, Dec. 6, 1996. "Viewpoint: Putting the Cell Cycle in Order".

Motoaki Ohtsubo, et al., *Molecular and Cellular Biology*, 15(5):2612–2624, May 1995. "Human Cyclin E, a Nuclear Protein Essential for the $G_1$–to–S Phase Transition".

Charles J. Sherr, *Science*, 274:1672–1677, Dec. 6, 1996. "Cancer Cell Cycles".

Bruce Stillman, *Science*, 274:1659–1664, Dec. 6, 1996. "Cell Cycle Control of DNA Replication".

John R. Strahler, et al., *Biochem. and Biophys. Res. Comm.*, 185(1):197–203, May 29, 1992. "Cell Cycle Progression is Associated with Distinct Patterns of Phosphorylation of OP18".

Takashi Fujita, et al., *Proc. Natl. Acad. Sci. U.S.A.*, 80:7437–7441, 1983. "Structure of the human interleukin 2 gene".

* cited by examiner

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 4081 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 117..3431

(xi) SEQUENCE DESCRIPTION: SEQ ID NO:1:

```
GGAATTCCCG GGTCGACCCA CGCGTCCGCT ACGCGCGCGG GGGTGCGCGC GGGAACGACC      60

GGGAAACACC GCGAGGGCCG GGGTGGGCCA GGCTGTGGGG ACGACGGGCT GCGACG        116
```

```
ATG GCC GCA GCG GCG GGC GGC GGC GGG CCG GGG ACA GCG GTA GGC GCC        164
Met Ala Ala Ala Ala Gly Gly Gly Gly Pro Gly Thr Ala Val Gly Ala
 1               5                  10                  15

ACG GGC TCG GGG ATT GCG GCG GCA GCC GCA GGC CTA GCT GTT TAT CGA        212
Thr Gly Ser Gly Ile Ala Ala Ala Ala Ala Gly Leu Ala Val Tyr Arg
                20                  25                  30

CGG AAG GAT GGG GGC CCG GCC ACC AAG TTT TGG GAG AGC CCG GAG ACG        260
Arg Lys Asp Gly Gly Pro Ala Thr Lys Phe Trp Glu Ser Pro Glu Thr
            35                  40                  45

GTG TCC CAG CTG GAT TCG GTG CGG GTC TGG CTG GGC AAG CAC TAC AAG        308
Val Ser Gln Leu Asp Ser Val Arg Val Trp Leu Gly Lys His Tyr Lys
        50                  55                  60

AAG TAT GTT CAT GCG GAT GCT CCT ACC AAT AAA ACA CTG GCT GGG CTG        356
Lys Tyr Val His Ala Asp Ala Pro Thr Asn Lys Thr Leu Ala Gly Leu
 65                 70                  75                  80

GTG GTG CAG CTT CTT CAG TTC CAG GAA GAT GCC TTT GGG AAG CAT GTC        404
Val Val Gln Leu Leu Gln Phe Gln Glu Asp Ala Phe Gly Lys His Val
                85                  90                  95

ACC AAC CCG GCC TTC ACC AAA CTC CCT GCA AAG TGT TTC ATG GAT TTC        452
Thr Asn Pro Ala Phe Thr Lys Leu Pro Ala Lys Cys Phe Met Asp Phe
            100                 105                 110

AAA GCT GGA GGC GCC TTA TGT CAC ATT CTT GGG GCT GCT TAC AAG TAT        500
Lys Ala Gly Gly Ala Leu Cys His Ile Leu Gly Ala Ala Tyr Lys Tyr
        115                 120                 125

AAA AAT GAA CAG GGA TGG CGG AGG TTT GAC CTA CAG AAC CCA TCT CGA        548
Lys Asn Glu Gln Gly Trp Arg Arg Phe Asp Leu Gln Asn Pro Ser Arg
130                 135                 140

ATG GAT CGT AAT GTG GAA ATG TTT ATG AAC ATT GAA AAA ACA TTG GTG        596
Met Asp Arg Asn Val Glu Met Phe Met Asn Ile Glu Lys Thr Leu Val
145                 150                 155                 160

CAG AAC AAT TGT TTG ACC AGA CCC AAC ATC TAC CTC ATT CCA GAC ATT        644
Gln Asn Asn Cys Leu Thr Arg Pro Asn Ile Tyr Leu Ile Pro Asp Ile
                165                 170                 175

GAT CTG AAG TTG GCT AAC AAA TTG AAA GAT ATC ATC AAA CGA CAT CAG        692
Asp Leu Lys Leu Ala Asn Lys Leu Lys Asp Ile Ile Lys Arg His Gln
            180                 185                 190

GGA ACA TTT ACG GAT GAG AAG TCA AAA GCT TCC CAC CAC ATT TAC CCA        740
Gly Thr Phe Thr Asp Glu Lys Ser Lys Ala Ser His His Ile Tyr Pro
        195                 200                 205

TAT TCT TCC TCA CAA GAC GAT GAA GAA TGG TTG AGA CCG GTG ATG AGA        788
Tyr Ser Ser Ser Gln Asp Asp Glu Glu Trp Leu Arg Pro Val Met Arg
210                 215                 220

AAA GAG AAG CAA GTG TTA GTG CAT TGG GGC TTT TAC CCA GAC AGC TAT        836
Lys Glu Lys Gln Val Leu Val His Trp Gly Phe Tyr Pro Asp Ser Tyr
225                 230                 235                 240

GAT ACT TGG GTC CAT AGT AAT GAT GTT GAT GCT GAA ATT GAA GAT CCA        884
Asp Thr Trp Val His Ser Asn Asp Val Asp Ala Glu Ile Glu Asp Pro
                245                 250                 255

CCA ATT CCA GAA AAA CCA TGG AAG GTT CAT GTG AAA TGG ATT TTG GAC        932
Pro Ile Pro Glu Lys Pro Trp Lys Val His Val Lys Trp Ile Leu Asp
            260                 265                 270

ACT GAT ATT TTC AAT GAA TGG ATG AAT GAG GAG GAT TAT GAG GTG GAT        980
Thr Asp Ile Phe Asn Glu Trp Met Asn Glu Glu Asp Tyr Glu Val Asp
        275                 280                 285

GAA AAT AGG AAG CCT GTG AGT TTT CGT CAG CGG ATT TCA ACC AAG AAT       1028
Glu Asn Arg Lys Pro Val Ser Phe Arg Gln Arg Ile Ser Thr Lys Asn
290                 295                 300

GAA GAG CCA GTC AGA AGT CCA GAA AGA AGA GAT AGA AAA GCA TCA GCT       1076
Glu Glu Pro Val Arg Ser Pro Glu Arg Arg Asp Arg Lys Ala Ser Ala
```

```
            305                 310                 315                 320
AAT GCT CGA AAG AGG AAA CAT TCG CCT TCG CCT CCC CCT CCG ACA CCA         1124
Asn Ala Arg Lys Arg Lys His Ser Pro Ser Pro Pro Pro Pro Thr Pro
                325                 330                 335

ACA GAA TCA CGG AAG AAG AGT GGG AAG AAA GGC CAA GCT AGC CTT TAT         1172
Thr Glu Ser Arg Lys Lys Ser Gly Lys Lys Gly Gln Ala Ser Leu Tyr
                340                 345                 350

GGG AAG CGC AGA AGT CAG AAA GAG GAA GAT GAG CAA GAA GAT CTA ACC         1220
Gly Lys Arg Arg Ser Gln Lys Glu Glu Asp Glu Gln Glu Asp Leu Thr
                355                 360                 365

AAG GAT ATG GAA GAC CCA ACA CCT GTA CCC AAT ATA GAA GAA GTA GTA         1268
Lys Asp Met Glu Asp Pro Thr Pro Val Pro Asn Ile Glu Glu Val Val
        370                 375                 380

CTT CCC AAA AAT GTG AAC CTA AAG AAA GAT AGT GAA AAT ACA CCT GTT         1316
Leu Pro Lys Asn Val Asn Leu Lys Lys Asp Ser Glu Asn Thr Pro Val
385                 390                 395                 400

AAA GGA GGA ACT GTA GCG GAT CTA GAT GAG CAG GAT GAA GAA ACA GTC         1364
Lys Gly Gly Thr Val Ala Asp Leu Asp Glu Gln Asp Glu Glu Thr Val
                    405                 410                 415

ACA GCA GGA GGA AAG GAA GAT GAA GAT CCT GCC AAA GGT GAT CAG AGT         1412
Thr Ala Gly Gly Lys Glu Asp Glu Asp Pro Ala Lys Gly Asp Gln Ser
                420                 425                 430

CGA TCA GTT GAC CTT GGG GAA GAT AAT GTG ACA GAG CAG ACC AAT CAC         1460
Arg Ser Val Asp Leu Gly Glu Asp Asn Val Thr Glu Gln Thr Asn His
            435                 440                 445

ATT ATT ATT CCT AGT TAT GCA TCA TGG TTT GAT TAT AAC TGT ATT CAT         1508
Ile Ile Ile Pro Ser Tyr Ala Ser Trp Phe Asp Tyr Asn Cys Ile His
        450                 455                 460

GTG ATT GAA CGG CGT GCT CTT CCT GAG TTC TTC AAT GGA AAA AAC AAA         1556
Val Ile Glu Arg Arg Ala Leu Pro Glu Phe Phe Asn Gly Lys Asn Lys
465                 470                 475                 480

TCC AAG ACT CCA GAA ATA TAC TTG GCA TAT CGA AAT TTT ATG ATT GAC         1604
Ser Lys Thr Pro Glu Ile Tyr Leu Ala Tyr Arg Asn Phe Met Ile Asp
                    485                 490                 495

ACG TAT CGT CTA AAC CCC CAA GAG TAT TTA ACT AGC ACT GCT TGT CGG         1652
Thr Tyr Arg Leu Asn Pro Gln Glu Tyr Leu Thr Ser Thr Ala Cys Arg
                500                 505                 510

AGG AAC TTG ACT GGA GAT GTG TGT GCT GTG ATG AGG GTC CAT GCC TTT         1700
Arg Asn Leu Thr Gly Asp Val Cys Ala Val Met Arg Val His Ala Phe
            515                 520                 525

TTA GAG CAG TGG GGA CTC GTT AAT TAC CAA GTT GAC CCG GAA AGT AGA         1748
Leu Glu Gln Trp Gly Leu Val Asn Tyr Gln Val Asp Pro Glu Ser Arg
        530                 535                 540

CCC ATG GCA ATG GGA CCT CCT CCT ACT CCT CAT TTT AAT GTA TTA GCT         1796
Pro Met Ala Met Gly Pro Pro Pro Thr Pro His Phe Asn Val Leu Ala
545                 550                 555                 560

GAT ACC CCC TCT GGG CTT GTG CCT CTG CAT CTT CGA TCA CCT CAG GTT         1844
Asp Thr Pro Ser Gly Leu Val Pro Leu His Leu Arg Ser Pro Gln Val
                    565                 570                 575

CCT GCT GCT CAA CAG ATG CTA AAT TTT CCT GAG AAA AAC AAG GAA AAA         1892
Pro Ala Ala Gln Gln Met Leu Asn Phe Pro Glu Lys Asn Lys Glu Lys
                580                 585                 590

CCA GTT GAT TTG CAG AAC TTT GGT CTC CGT ACT GAC ATT TAC TCC AAG         1940
Pro Val Asp Leu Gln Asn Phe Gly Leu Arg Thr Asp Ile Tyr Ser Lys
            595                 600                 605

AAA ACA TTA GCA AAG AGT AAA GGT GCT AGT GCT GGA AGA GAA TGG ACT         1988
Lys Thr Leu Ala Lys Ser Lys Gly Ala Ser Ala Gly Arg Glu Trp Thr
        610                 615                 620

GAA CAG GAG ACC CTT CTA CTC CTG GAG GCC CTG GAG ATG TAC AAG GAT         2036
```

```
                    -continued

Glu Gln Glu Thr Leu Leu Leu Glu Ala Leu Glu Met Tyr Lys Asp
625                 630                 635                 640

GAT TGG AAC AAA GTG TCG GAA CAT GTT GGA AGT CGT ACT CAG GAT GAA   2084
Asp Trp Asn Lys Val Ser Glu His Val Gly Ser Arg Thr Gln Asp Glu
                        645                 650                 655

TGC ATC CTC CAC TTT TTG AGA CTT CCC ATT GAG GAC CCA TAC CTT GAG   2132
Cys Ile Leu His Phe Leu Arg Leu Pro Ile Glu Asp Pro Tyr Leu Glu
                660                 665                 670

AAT TCA GAT GCT TCC CTT GGG CCT TTG GCC TAC CAG CCT GTC CCC TTC   2180
Asn Ser Asp Ala Ser Leu Gly Pro Leu Ala Tyr Gln Pro Val Pro Phe
            675                 680                 685

AGT CAG TCA GGA AAT CCA GTT ATG AGT ACT GTT GCT TTT TTG GCA TCT   2228
Ser Gln Ser Gly Asn Pro Val Met Ser Thr Val Ala Phe Leu Ala Ser
        690                 695                 700

GTG GTG GAC CCT CGC GTG GCA TCT GCT GCA GCA AAA GCG GCT TTG GAG   2276
Val Val Asp Pro Arg Val Ala Ser Ala Ala Ala Lys Ala Ala Leu Glu
705                 710                 715                 720

GAG TTT TCT CGG GTC CGG GAG GAG GTA CCA CTG GAA TTG GTT GAA GCT   2324
Glu Phe Ser Arg Val Arg Glu Glu Val Pro Leu Glu Leu Val Glu Ala
                725                 730                 735

CAT GTC AAG AAA GTA CAA GAA GCA GCA CGA GCC TCT GGG AAA GTG GAT   2372
His Val Lys Lys Val Gln Glu Ala Ala Arg Ala Ser Gly Lys Val Asp
                740                 745                 750

CCC ACC TAC GGT CTG GAG AGC AGC TGC ATT GCA GGC ACA GGG CCC GAT   2420
Pro Thr Tyr Gly Leu Glu Ser Ser Cys Ile Ala Gly Thr Gly Pro Asp
            755                 760                 765

GAG CCA GAG AAG CTT GAA GGA GCT GAA GAG GAA AAA ATG GAA GCC GAC   2468
Glu Pro Glu Lys Leu Glu Gly Ala Glu Glu Glu Lys Met Glu Ala Asp
        770                 775                 780

CCT GAT GGT CAG CAG CCT GAA AAG GCA GAA AAT AAA GTG GAA AAT GAA   2516
Pro Asp Gly Gln Gln Pro Glu Lys Ala Glu Asn Lys Val Glu Asn Glu
785                 790                 795                 800

ACG GAT GAA GGT GAT AAA GCA CAA GAT GGA GAA AAT GAA AAA AAT AGT   2564
Thr Asp Glu Gly Asp Lys Ala Gln Asp Gly Glu Asn Glu Lys Asn Ser
                805                 810                 815

GAA AAG GAA CAG GAT AGT GAA GTG AGT GAG GAT ACC AAA TCA GAA GAA   2612
Glu Lys Glu Gln Asp Ser Glu Val Ser Glu Asp Thr Lys Ser Glu Glu
                820                 825                 830

AAG GAG ACT GAA GAG AAC AAA GAA CTC ACT GAT ACA TGT AAA GAA AGA   2660
Lys Glu Thr Glu Glu Asn Lys Glu Leu Thr Asp Thr Cys Lys Glu Arg
            835                 840                 845

GAA AGT GAT ACT GGG AAG AAG AAA GTA GAA CAT GAA ATT TCC GAA GGA   2708
Glu Ser Asp Thr Gly Lys Lys Lys Val Glu His Glu Ile Ser Glu Gly
        850                 855                 860

AAT GTT GCC ACA GCC GCA GCA GCT GCT CTT GCC TCA GCG GCT ACC AAA   2756
Asn Val Ala Thr Ala Ala Ala Ala Ala Leu Ala Ser Ala Ala Thr Lys
865                 870                 875                 880

GCC AAG CAC CTG GCT GCA GTG GAA GAA AGA AAG ATC AAG TCC CTG GTA   2804
Ala Lys His Leu Ala Ala Val Glu Glu Arg Lys Ile Lys Ser Leu Val
                885                 890                 895

GCT CTC TTG GTT GAG ACA CAA ATG AAG AAA CTA GAG ATC AAA CTT CGA   2852
Ala Leu Leu Val Glu Thr Gln Met Lys Lys Leu Glu Ile Lys Leu Arg
                900                 905                 910

CAT TTT GAA GAG CTG GAA ACT ATC ATG GAC AGA GAG AAA GAA GCT CTA   2900
His Phe Glu Glu Leu Glu Thr Ile Met Asp Arg Glu Lys Glu Ala Leu
            915                 920                 925

GAA CAA CAG AGG CAG CAG TTG CTT ACT GAA CGC CAA AAC TTC CAC ATG   2948
Glu Gln Gln Arg Gln Gln Leu Leu Thr Glu Arg Gln Asn Phe His Met
        930                 935                 940
```

-continued

```
GAA CAG CTG AAG TAT GCT GAA TTA CGA GCA CGA CAG CAA ATG GAA CAG        2996
Glu Gln Leu Lys Tyr Ala Glu Leu Arg Ala Arg Gln Gln Met Glu Gln
945                 950                 955                 960

CAG CAG CAT GGC CAG AAC CCT CAA CAG GCA CAC CAG CAC TCA GGA GGA        3044
Gln Gln His Gly Gln Asn Pro Gln Gln Ala His Gln His Ser Gly Gly
            965                 970                 975

CCT GGC CTG GCC CCA CTT GGA GCA GCA GGG CAC CCT GGC ATG ATG CCT        3092
Pro Gly Leu Ala Pro Leu Gly Ala Ala Gly His Pro Gly Met Met Pro
        980                 985                 990

CAT CAA CAG CCC CCT CCC TAC CCT CTG ATG CAC CAC CAG ATG CCA CCA        3140
His Gln Gln Pro Pro Pro Tyr Pro Leu Met His His Gln Met Pro Pro
    995                 1000                1005

CCT CAT CCA CCC CAG CCA GGT CAG ATA CCA GGC CCA GGT TCC ATG ATG        3188
Pro His Pro Pro Gln Pro Gly Gln Ile Pro Gly Pro Gly Ser Met Met
1010                1015                1020

CCC GGG CAG CAC ATG CCA GGC CGC ATG ATT CCC ACT GTT GCA GCC AAC        3236
Pro Gly Gln His Met Pro Gly Arg Met Ile Pro Thr Val Ala Ala Asn
1025                1030                1035                1040

ATC CAC CCC TCT GGG AGT GGC CCT ACC CCT CCT GGC ATG CCA CCA ATG        3284
Ile His Pro Ser Gly Ser Gly Pro Thr Pro Pro Gly Met Pro Pro Met
                1045                1050                1055

CCA GGA AAC ATC TTA GGA CCC CGG GTA CCC CTG ACA GCA CCT AAC GGC        3332
Pro Gly Asn Ile Leu Gly Pro Arg Val Pro Leu Thr Ala Pro Asn Gly
            1060                1065                1070

ATG TAT CCC CCT CCA CCA CAG CAG CAG CCA CCG CCA CCA CCA CCT GCA        3380
Met Tyr Pro Pro Pro Pro Gln Gln Gln Pro Pro Pro Pro Pro Pro Ala
        1075                1080                1085

GAT GGG GTC CCT CCG CCT CCT GCT CCT GGC CCG CCA GCC TCA GCT GCT        3428
Asp Gly Val Pro Pro Pro Pro Ala Pro Gly Pro Pro Ala Ser Ala Ala
    1090                1095                1100

CCT TAGCCTGGAA GATGCAGGGA ACCTCCACGC CCACCACCAT GAGCTGGAGT             3481
Pro
1105

GGGGATGACA AGACTTGTGT TCCTCAACTT TCTTGGTTTC TTTCAGGATT TTTCTTCTCA      3541

CAGCTCCAAG CACGTGTCCC GTGCCTCCCC ACTCCTCTTA CCACCCCTCT CTCTGACACT      3601

TTTTGTGTTG GGTCCTCAGC AACACTCAA GGGGAAACCT GTAGTGACAG TGTGCCCTGG       3661

TCATCCTTAA AATAACCTGC ATCTCCCCTG TCCTGGTGTG GGAGTAAGCT GACAGTTTCT      3721

CTGCAGGTCC TGTCAACTTT AGCATGCTAT GTCTTTACCA TTTTTGCTCT CTTGCAGTTT      3781

TTTGCTTTGT CTTATGCTTC TATGGATAAT GCTATATAAT CATTATCTTT TTATCTTTCT      3841

GTTATTATTG TTTTAAAGGA GAGCATCCTA AGTTAATAGG AACCAAAAAA TAATGATGGG      3901

CAGAAGGGGG GGAATAGCCA CAGGGGACAA ACCTTAAGGC ATTATAAGTG ACCTTATTTC      3961

TGCTTTTCTG AGCTAAGAAT GGTGCTGATG GTAAAGTTTG AGACTTTTGC CACACACAAA     4021

TTTGTGAAAA TTAAACGAGA TGTTGGAAGG AGAAAAAAAA AAAAAAAAAA GGGCGGCCGC     4081

(2) INFORMATION FOR SEQ ID NO:2:

(i) SEQUENCE CHARACTERISTICS:
        (A) LENGTH: 1105 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ala Ala Ala Gly Gly Gly Gly Pro Gly Thr Ala Val Gly Ala
  1               5                  10                  15
```

-continued

```
Thr Gly Ser Gly Ile Ala Ala Ala Ala Gly Leu Ala Val Tyr Arg
         20                  25                  30

Arg Lys Asp Gly Gly Pro Ala Thr Lys Phe Trp Glu Ser Pro Glu Thr
     35                  40                  45

Val Ser Gln Leu Asp Ser Val Arg Val Trp Leu Gly Lys His Tyr Lys
     50                  55                  60

Lys Tyr Val His Ala Asp Ala Pro Thr Asn Lys Thr Leu Ala Gly Leu
 65                  70                  75                  80

Val Val Gln Leu Leu Gln Phe Gln Glu Asp Ala Phe Gly Lys His Val
                 85                  90                  95

Thr Asn Pro Ala Phe Thr Lys Leu Pro Ala Lys Cys Phe Met Asp Phe
            100                 105                 110

Lys Ala Gly Gly Ala Leu Cys His Ile Leu Gly Ala Ala Tyr Lys Tyr
            115                 120                 125

Lys Asn Glu Gln Gly Trp Arg Arg Phe Asp Leu Gln Asn Pro Ser Arg
        130                 135                 140

Met Asp Arg Asn Val Glu Met Phe Met Asn Ile Glu Lys Thr Leu Val
145                 150                 155                 160

Gln Asn Asn Cys Leu Thr Arg Pro Asn Ile Tyr Leu Ile Pro Asp Ile
                165                 170                 175

Asp Leu Lys Leu Ala Asn Lys Leu Lys Asp Ile Ile Lys Arg His Gln
            180                 185                 190

Gly Thr Phe Thr Asp Glu Lys Ser Lys Ala Ser His His Ile Tyr Pro
        195                 200                 205

Tyr Ser Ser Gln Asp Asp Glu Glu Trp Leu Arg Pro Val Met Arg
    210                 215                 220

Lys Glu Lys Gln Val Leu Val His Trp Gly Phe Tyr Pro Asp Ser Tyr
225                 230                 235                 240

Asp Thr Trp Val His Ser Asn Asp Val Asp Ala Glu Ile Glu Asp Pro
                245                 250                 255

Pro Ile Pro Glu Lys Pro Trp Lys Val His Val Lys Trp Ile Leu Asp
            260                 265                 270

Thr Asp Ile Phe Asn Glu Trp Met Asn Glu Glu Asp Tyr Glu Val Asp
        275                 280                 285

Glu Asn Arg Lys Pro Val Ser Phe Arg Gln Arg Ile Ser Thr Lys Asn
    290                 295                 300

Glu Glu Pro Val Arg Ser Pro Glu Arg Arg Asp Arg Lys Ala Ser Ala
305                 310                 315                 320

Asn Ala Arg Lys Arg Lys His Ser Pro Ser Pro Pro Pro Thr Pro
                325                 330                 335

Thr Glu Ser Arg Lys Lys Ser Gly Lys Lys Gly Gln Ala Ser Leu Tyr
        340                 345                 350

Gly Lys Arg Arg Ser Gln Lys Glu Glu Asp Glu Gln Glu Asp Leu Thr
    355                 360                 365

Lys Asp Met Glu Asp Pro Thr Pro Val Pro Asn Ile Glu Glu Val Val
    370                 375                 380

Leu Pro Lys Asn Val Asn Leu Lys Lys Asp Ser Glu Asn Thr Pro Val
385                 390                 395                 400

Lys Gly Gly Thr Val Ala Asp Leu Asp Glu Gln Asp Glu Glu Thr Val
                405                 410                 415

Thr Ala Gly Gly Lys Glu Asp Glu Asp Pro Ala Lys Gly Asp Gln Ser
            420                 425                 430

Arg Ser Val Asp Leu Gly Glu Asp Asn Val Thr Glu Gln Thr Asn His
```

-continued

```
            435                 440                 445
Ile Ile Ile Pro Ser Tyr Ala Ser Trp Phe Asp Tyr Asn Cys Ile His
        450                 455                 460
Val Ile Glu Arg Arg Ala Leu Pro Glu Phe Phe Asn Gly Lys Asn Lys
465                 470                 475                 480
Ser Lys Thr Pro Glu Ile Tyr Leu Ala Tyr Arg Asn Phe Met Ile Asp
                485                 490                 495
Thr Tyr Arg Leu Asn Pro Gln Glu Tyr Leu Thr Ser Thr Ala Cys Arg
            500                 505                 510
Arg Asn Leu Thr Gly Asp Val Cys Ala Val Met Arg Val His Ala Phe
        515                 520                 525
Leu Glu Gln Trp Gly Leu Val Asn Tyr Gln Val Asp Pro Glu Ser Arg
    530                 535                 540
Pro Met Ala Met Gly Pro Pro Thr Pro His Phe Asn Val Leu Ala
545                 550                 555                 560
Asp Thr Pro Ser Gly Leu Val Pro Leu His Leu Arg Ser Pro Gln Val
                565                 570                 575
Pro Ala Ala Gln Gln Met Leu Asn Phe Pro Glu Lys Asn Lys Glu Lys
            580                 585                 590
Pro Val Asp Leu Gln Asn Phe Gly Leu Arg Thr Asp Ile Tyr Ser Lys
        595                 600                 605
Lys Thr Leu Ala Lys Ser Lys Gly Ala Ser Ala Gly Arg Glu Trp Thr
    610                 615                 620
Glu Gln Glu Thr Leu Leu Leu Leu Glu Ala Leu Glu Met Tyr Lys Asp
625                 630                 635                 640
Asp Trp Asn Lys Val Ser Glu His Val Gly Ser Arg Thr Gln Asp Glu
                645                 650                 655
Cys Ile Leu His Phe Leu Arg Leu Pro Ile Glu Asp Pro Tyr Leu Glu
            660                 665                 670
Asn Ser Asp Ala Ser Leu Gly Pro Leu Ala Tyr Gln Pro Val Pro Phe
        675                 680                 685
Ser Gln Ser Gly Asn Pro Val Met Ser Thr Val Ala Phe Leu Ala Ser
    690                 695                 700
Val Val Asp Pro Arg Val Ala Ser Ala Ala Lys Ala Ala Leu Glu
705                 710                 715                 720
Glu Phe Ser Arg Val Arg Glu Glu Val Pro Leu Glu Leu Val Glu Ala
                725                 730                 735
His Val Lys Lys Val Gln Glu Ala Ala Arg Ala Ser Gly Lys Val Asp
            740                 745                 750
Pro Thr Tyr Gly Leu Glu Ser Ser Cys Ile Ala Gly Thr Gly Pro Asp
        755                 760                 765
Glu Pro Glu Lys Leu Glu Gly Ala Glu Glu Lys Met Glu Ala Asp
    770                 775                 780
Pro Asp Gly Gln Gln Pro Glu Lys Ala Glu Asn Lys Val Glu Asn Glu
785                 790                 795                 800
Thr Asp Glu Gly Asp Lys Ala Gln Asp Gly Glu Asn Glu Lys Asn Ser
                805                 810                 815
Glu Lys Glu Gln Asp Ser Glu Val Ser Glu Asp Thr Lys Ser Glu Glu
            820                 825                 830
Lys Glu Thr Glu Glu Asn Lys Glu Leu Thr Asp Thr Cys Lys Glu Arg
        835                 840                 845
Glu Ser Asp Thr Gly Lys Lys Val Glu His Glu Ile Ser Glu Gly
    850                 855                 860
```

```
Asn Val Ala Thr Ala Ala Ala Ala Leu Ala Ser Ala Ala Thr Lys
865                 870                 875                 880

Ala Lys His Leu Ala Ala Val Glu Glu Arg Lys Ile Lys Ser Leu Val
            885                 890                 895

Ala Leu Leu Val Glu Thr Gln Met Lys Lys Leu Glu Ile Lys Leu Arg
                900                 905                 910

His Phe Glu Glu Leu Glu Thr Ile Met Asp Arg Glu Lys Glu Ala Leu
            915                 920                 925

Glu Gln Gln Arg Gln Gln Leu Leu Thr Glu Arg Gln Asn Phe His Met
    930                 935                 940

Glu Gln Leu Lys Tyr Ala Glu Leu Arg Ala Arg Gln Gln Met Glu Gln
945                 950                 955                 960

Gln Gln His Gly Gln Asn Pro Gln Gln Ala His Gln His Ser Gly Gly
            965                 970                 975

Pro Gly Leu Ala Pro Leu Gly Ala Ala Gly His Pro Gly Met Met Pro
            980                 985                 990

His Gln Gln Pro Pro Pro Tyr Pro Leu Met His His Gln Met Pro Pro
            995                 1000                1005

Pro His Pro Pro Gln Pro Gly Gln Ile Pro Gly Pro Gly Ser Met Met
    1010                1015                1020

Pro Gly Gln His Met Pro Gly Arg Met Ile Pro Thr Val Ala Ala Asn
1025                1030                1035                1040

Ile His Pro Ser Gly Ser Gly Pro Thr Pro Pro Gly Met Pro Pro Met
                1045                1050                1055

Pro Gly Asn Ile Leu Gly Pro Arg Val Pro Leu Thr Ala Pro Asn Gly
            1060                1065                1070

Met Tyr Pro Pro Pro Gln Gln Gln Pro Pro Pro Pro Pro Pro Pro Ala
        1075                1080                1085

Asp Gly Val Pro Pro Pro Ala Pro Gly Pro Pro Ala Ser Ala Ala
        1090                1095                1100

Pro
1105

(2) INFORMATION FOR SEQ ID NO:3:

(i) SEQUENCE CHARACTERISTICS:
        (A) LENGTH: 642 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..642

(xi) SEQUENCE DESCRIPTION: SEQ ID NO:3:

ATG GAG GCG CAA CTT CCA GTG CTC GTA AAA ACA GAT GGG ATG AAA CCC       48
Met Glu Ala Gln Leu Pro Val Leu Val Lys Thr Asp Gly Met Lys Pro
1               5                   10                  15

CCA AAA CAG AGA GAG ATA CTC TTG GGC ATG GAA GTG GAT GGG GTG AGA      96
Pro Lys Gln Arg Glu Ile Leu Leu Gly Met Glu Val Asp Gly Val Arg
                20                  25                  30

CTC CTC GAA CAG ATC GAG GCG GAG ATT ATA TTG GTG AAA CAC CGA CTC      144
Leu Leu Glu Gln Ile Glu Ala Glu Ile Ile Leu Val Lys His Arg Leu
            35                  40                  45

CTG GAG CCA GTA AAA GAA ACT CAC GGT GGG ATG AAA CAC CAG CTA GTC      192
```

```
Leu Glu Pro Val Lys Glu Thr His Gly Gly Met Lys His Gln Leu Val
     50                  55                  60

AGA TGG GTG GAA GCA CTC CCA GTT CTG ACC CCT GGA AAG ACA CCA ATT      240
Arg Trp Val Glu Ala Leu Pro Val Leu Thr Pro Gly Lys Thr Pro Ile
 65                  70                  75                  80

GGC ACA CCA GCC ATG AAC ATG GCT ACC CCT ACT CCA GGT CAC ATA ATG      288
Gly Thr Pro Ala Met Asn Met Ala Thr Pro Thr Pro Gly His Ile Met
                 85                  90                  95

AGT ATG ACT CCT GAA CAG CTT CAG GCT TGG CGG TGG GAA AGA GAA ATT      336
Ser Met Thr Pro Glu Gln Leu Gln Ala Trp Arg Trp Glu Arg Glu Ile
             100                 105                 110

GAT GAG AGA AAT CGC CCA CTT TCT GAT GAG GAA TTA GAT GCT ATG TTC      384
Asp Glu Arg Asn Arg Pro Leu Ser Asp Glu Glu Leu Asp Ala Met Phe
             115                 120                 125

CCA GAA GGA TAT AAG GTA CTT CCT CCT CCA GCT GGT TAT GTT CCT ATT      432
Pro Glu Gly Tyr Lys Val Leu Pro Pro Pro Ala Gly Tyr Val Pro Ile
     130                 135                 140

CGA ACT CCA GCT CGA AAG CTG ACA GCT ACT CCA ACA CCT TTG GGT GGT      480
Arg Thr Pro Ala Arg Lys Leu Thr Ala Thr Pro Thr Pro Leu Gly Gly
145                 150                 155                 160

ATG ACT GGT TTC CAC ATG CAA ACT GAA GAT CGA ACT ATG AAA AGT GTT      528
Met Thr Gly Phe His Met Gln Thr Glu Asp Arg Thr Met Lys Ser Val
                 165                 170                 175

AAT GAC CAG CCA TCT GGA AAT CTT CCA TTT TTA AAA CCT GAT GAT ATT      576
Asn Asp Gln Pro Ser Gly Asn Leu Pro Phe Leu Lys Pro Asp Asp Ile
             180                 185                 190

CAA TAC TTT GAT AAA CTA TTG GTT GAT GTT GAT GAA TCA ACA CTT AGT      624
Gln Tyr Phe Asp Lys Leu Leu Val Asp Val Asp Glu Ser Thr Leu Ser
             195                 200                 205

CCA GAA GAG CAA AAA AAA                                              642
Pro Glu Glu Gln Lys Lys
    210

(2) INFORMATION FOR SEQ ID NO:4:

(i) SEQUENCE CHARACTERISTICS:
        (A) LENGTH: 214 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Ala Gln Leu Pro Val Leu Val Lys Thr Asp Gly Met Lys Pro
 1               5                  10                  15

Pro Lys Gln Arg Glu Ile Leu Leu Gly Met Glu Val Asp Gly Val Arg
                 20                  25                  30

Leu Leu Glu Gln Ile Glu Ala Glu Ile Ile Leu Val Lys His Arg Leu
             35                  40                  45

Leu Glu Pro Val Lys Glu Thr His Gly Gly Met Lys His Gln Leu Val
     50                  55                  60

Arg Trp Val Glu Ala Leu Pro Val Leu Thr Pro Gly Lys Thr Pro Ile
 65                  70                  75                  80

Gly Thr Pro Ala Met Asn Met Ala Thr Pro Thr Pro Gly His Ile Met
                 85                  90                  95

Ser Met Thr Pro Glu Gln Leu Gln Ala Trp Arg Trp Glu Arg Glu Ile
             100                 105                 110

Asp Glu Arg Asn Arg Pro Leu Ser Asp Glu Glu Leu Asp Ala Met Phe
             115                 120                 125
```

-continued

```
Pro Glu Gly Tyr Lys Val Leu Pro Pro Ala Gly Tyr Val Pro Ile
    130                 135                 140

Arg Thr Pro Ala Arg Lys Leu Thr Ala Thr Pro Thr Pro Leu Gly Gly
145                 150                 155                 160

Met Thr Gly Phe His Met Gln Thr Glu Asp Arg Thr Met Lys Ser Val
                165                 170                 175

Asn Asp Gln Pro Ser Gly Asn Leu Pro Phe Leu Lys Pro Asp Asp Ile
            180                 185                 190

Gln Tyr Phe Asp Lys Leu Leu Val Asp Val Asp Glu Ser Thr Leu Ser
        195                 200                 205

Pro Glu Glu Gln Lys Lys
    210
```

(2) INFORMATION FOR SEQ ID NO:5:

(i) SEQUENCE CHARACTERISTICS:
        (A) LENGTH: 2932 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 266..2683

(xi) SEQUENCE DESCRIPTION: SEQ ID NO:5:

```
GGAATTCCCG GGTCGACCCA CGCGTCCGCG TCGCTGCCGC TGCCGCTGCC ACTGCCACTG      60

CCACCTCGCG GATCAGGAGC CAGCGTTGTT CGCCCGACGC CTCGCTGCCG GTGGGAGGAA     120

GCGAGAGGGA AGCCGCTTGC GGGTTTGTCG CCGCTGCTCG CCCACCGCCT GGAAGAGCCG     180

AGCCCCGGCC CAGTCGGTCG CTTGCCACCG CTCGTAGCCG TTACCCGCGG GCCGCCACAG     240

CCGCCGGCCG GGAGAGGCGC GCGCC ATG GCT TCT GGA GCC GAT TCA AAA GGT      292
                              Met Ala Ser Gly Ala Asp Ser Lys Gly
                                1               5

GAT GAC CTA TCA ACA GCC ATT CTC AAA CAG AAG AAC CGT CCC AAT CGG      340
Asp Asp Leu Ser Thr Ala Ile Leu Lys Gln Lys Asn Arg Pro Asn Arg
 10                  15                  20                  25

TTA ATT GTT GAT GAA GCC ATC AAT GAG GAC AAC AGT GTG GTG TCC TTG      388
Leu Ile Val Asp Glu Ala Ile Asn Glu Asp Asn Ser Val Val Ser Leu
                 30                  35                  40

TCC CAG CCC AAG ATG GAT GAA TTG CAG TTG TTC CGA GGT GAC ACA GTG      436
Ser Gln Pro Lys Met Asp Glu Leu Gln Leu Phe Arg Gly Asp Thr Val
             45                  50                  55

TTG CTG AAA GGA AAG AAG AGA CGA GAA GCT GTT TGC ATC GTC CTT TCT      484
Leu Leu Lys Gly Lys Lys Arg Arg Glu Ala Val Cys Ile Val Leu Ser
         60                  65                  70

GAT GAT ACT TGT TCT GAT GAG AAG ATT CGG ATG AAT AGA GTT GTT CGG      532
Asp Asp Thr Cys Ser Asp Glu Lys Ile Arg Met Asn Arg Val Val Arg
     75                  80                  85

AAT AAC CTT CGT GTA CGC CTA GGG GAT GTC ATC AGC ATC CAG CCA TGC      580
Asn Asn Leu Arg Val Arg Leu Gly Asp Val Ile Ser Ile Gln Pro Cys
 90                  95                 100                 105

CCT GAT GTG AAG TAC GGC AAA CGT ATC CAT GTG CTG CCC ATT GAT GAC      628
Pro Asp Val Lys Tyr Gly Lys Arg Ile His Val Leu Pro Ile Asp Asp
                110                 115                 120

ACA GTG GAA GGC ATT ACT GGT AAT CTC TTC GAG GTA TAC CTT AAG CCG      676
Thr Val Glu Gly Ile Thr Gly Asn Leu Phe Glu Val Tyr Leu Lys Pro
            125                 130                 135
```

```
TAC TTC CTG GAA GCG TAT CGA CCC ATC CGG AAA GGA GAC ATT TTT CTT      724
Tyr Phe Leu Glu Ala Tyr Arg Pro Ile Arg Lys Gly Asp Ile Phe Leu
        140                 145                 150

GTC CGT GGT GGG ATG CGT GCT GTG GAG TTC AAA GTG GTG GAA ACA GAT      772
Val Arg Gly Gly Met Arg Ala Val Glu Phe Lys Val Val Glu Thr Asp
    155                 160                 165

CCT AGC CCT TAT TGC ATT GTT GCT CCA GAC ACA GTG ATC CAC TGC GAA      820
Pro Ser Pro Tyr Cys Ile Val Ala Pro Asp Thr Val Ile His Cys Glu
170                 175                 180                 185

GGG GAG CCT ATC AAA CGA GAG GAT GAG GAA GAG TCC TTG AAT GAA GTA      868
Gly Glu Pro Ile Lys Arg Glu Asp Glu Glu Glu Ser Leu Asn Glu Val
                190                 195                 200

GGG TAT GAT GAC ATT GGT GGC TGC AGG AAG CAG CTA GCT CAG ATA AAG      916
Gly Tyr Asp Asp Ile Gly Gly Cys Arg Lys Gln Leu Ala Gln Ile Lys
            205                 210                 215

GAG ATG GTG GAA CTG CCC CTG AGA CAT CCT GCC CTC TTT AAG GCA ATT      964
Glu Met Val Glu Leu Pro Leu Arg His Pro Ala Leu Phe Lys Ala Ile
        220                 225                 230

GGT GTG AAG CCT CCT AGA GGA ATC CTG CTT TAC GGA CCT CCT GGA ACA     1012
Gly Val Lys Pro Pro Arg Gly Ile Leu Leu Tyr Gly Pro Pro Gly Thr
    235                 240                 245

GGA AAG ACC CTG ATT GCT CGA GCT GTA GCA AAT GAG ACT GGA GCC TTC     1060
Gly Lys Thr Leu Ile Ala Arg Ala Val Ala Asn Glu Thr Gly Ala Phe
250                 255                 260                 265

TTC TTC TTG ATC AAT GGT CCT GAG ATC ATG AGC AAA TTG GCT GGT GAG     1108
Phe Phe Leu Ile Asn Gly Pro Glu Ile Met Ser Lys Leu Ala Gly Glu
                270                 275                 280

TCT GAG AGC AAC CTT CGT AAA GCC TTT GAG GAG GCT GAG AAG AAT GCT     1156
Ser Glu Ser Asn Leu Arg Lys Ala Phe Glu Glu Ala Glu Lys Asn Ala
            285                 290                 295

CCT GCC ATC ATC TTC ATT GAT GAG CTA GAT GCC ATC GCT CCC AAA AGA     1204
Pro Ala Ile Ile Phe Ile Asp Glu Leu Asp Ala Ile Ala Pro Lys Arg
        300                 305                 310

GAG AAA ACT CAT GGC GAG GTG GAG CGG CGC ATT GTA TCA CAG TTG TTG     1252
Glu Lys Thr His Gly Glu Val Glu Arg Arg Ile Val Ser Gln Leu Leu
    315                 320                 325

ACC CTC ATG GAT GGC CTA AAG CAG AGG GCA CAT GTG ATT GTT ATG GCA     1300
Thr Leu Met Asp Gly Leu Lys Gln Arg Ala His Val Ile Val Met Ala
330                 335                 340                 345

GCA ACC AAC AGA CCC AAC AGC ATT GAC CCA GCT CTA CGG CGA TTT GGT     1348
Ala Thr Asn Arg Pro Asn Ser Ile Asp Pro Ala Leu Arg Arg Phe Gly
                350                 355                 360

CGC TTT GAC AGG GAG GTA GAT ATT GGA ATT CCT GAT GCT ACA GGA CGC     1396
Arg Phe Asp Arg Glu Val Asp Ile Gly Ile Pro Asp Ala Thr Gly Arg
            365                 370                 375

TTA GAG ATT CTT CAG ATC CAT ACC AAG AAC ATG AAG CTG GCA GAT GAT     1444
Leu Glu Ile Leu Gln Ile His Thr Lys Asn Met Lys Leu Ala Asp Asp
        380                 385                 390

GTG GAC CTG GAA CAG GTA GCC AAT GAG ACT CAC GGG CAT GTG GGT GCT     1492
Val Asp Leu Glu Gln Val Ala Asn Glu Thr His Gly His Val Gly Ala
    395                 400                 405

GAC TTA GCA GCC CTG TGC TCA GAG GCT GCT CTG CAA GCC ATC CGC AAG     1540
Asp Leu Ala Ala Leu Cys Ser Glu Ala Ala Leu Gln Ala Ile Arg Lys
410                 415                 420                 425

AAG ATG GAT CTC ATT GAC CTA GAG GAT GAG ACC ATT GAT GCC GAG GTC     1588
Lys Met Asp Leu Ile Asp Leu Glu Asp Glu Thr Ile Asp Ala Glu Val
                430                 435                 440

ATG AAC TCT CTA GCA GTT ACT ATG GAT GAC TTC CGG TGG GCC TTG AGC     1636
Met Asn Ser Leu Ala Val Thr Met Asp Asp Phe Arg Trp Ala Leu Ser
            445                 450                 455
```

```
CAG AGT AAC CCA TCA GCA CTG CGG GAA ACC GTG GTA GAG GTG CCA CAG    1684
Gln Ser Asn Pro Ser Ala Leu Arg Glu Thr Val Val Glu Val Pro Gln
            460                 465                 470

GTA ACC TGG GAA GAC ATC GGG GGC CTA GAG GAT GTC AAA CGT GAG CTA    1732
Val Thr Trp Glu Asp Ile Gly Gly Leu Glu Asp Val Lys Arg Glu Leu
        475                 480                 485

CAG GAG CTG GTC CAG TAT CCT GTG GAG CAC CCA GAC AAA TTC CTG AAG    1780
Gln Glu Leu Val Gln Tyr Pro Val Glu His Pro Asp Lys Phe Leu Lys
490                 495                 500                 505

TTT GGC ATG ACA CCT TCC AAG GGA GTT CTG TTC TAT GGA CCT CCT GGC    1828
Phe Gly Met Thr Pro Ser Lys Gly Val Leu Phe Tyr Gly Pro Pro Gly
                510                 515                 520

TGT GGG AAA ACT TTG TTG GCC AAA GCC ATT GCT AAT GAA TGC CAG GCC    1876
Cys Gly Lys Thr Leu Leu Ala Lys Ala Ile Ala Asn Glu Cys Gln Ala
            525                 530                 535

AAC TTC ATC TCC ATC AAG GGT CCT GAG CTG CTC ACC ATG TGG TTT GGG    1924
Asn Phe Ile Ser Ile Lys Gly Pro Glu Leu Leu Thr Met Trp Phe Gly
        540                 545                 550

GAG TCT GAG GCC AAT GTC AGA GAA ATC TTT GAC AAG GCC CGC CAA GCT    1972
Glu Ser Glu Ala Asn Val Arg Glu Ile Phe Asp Lys Ala Arg Gln Ala
    555                 560                 565

GCC CCC TGT GTG CTA TTC TTT GAT GAG CTG GAT TCG ATT GCC AAG GCT    2020
Ala Pro Cys Val Leu Phe Phe Asp Glu Leu Asp Ser Ile Ala Lys Ala
570                 575                 580                 585

CGT GGA GGT AAC ATT GGA GAT GGT GGT GGG GCT GCT GAC CGA GTC ATC    2068
Arg Gly Gly Asn Ile Gly Asp Gly Gly Gly Ala Ala Asp Arg Val Ile
                590                 595                 600

AAC CAG ATC CTG ACA GAA ATG GAT GGC ATG TCC ACA AAA AAA AAT GTG    2116
Asn Gln Ile Leu Thr Glu Met Asp Gly Met Ser Thr Lys Lys Asn Val
            605                 610                 615

TTC ATC ATT GGC GCT ACC AAC CGG CCT GAC ATC ATT GAT CCT GCC ATC    2164
Phe Ile Ile Gly Ala Thr Asn Arg Pro Asp Ile Ile Asp Pro Ala Ile
        620                 625                 630

CTC AGA CCT GGC CGT CTT GAT CAG CTC ATC TAC ATC CCA CTT CCT GAT    2212
Leu Arg Pro Gly Arg Leu Asp Gln Leu Ile Tyr Ile Pro Leu Pro Asp
    635                 640                 645

GAG AAG TCC CGT GTT GCC ATC CTC AAG GCT AAC CTG CGC AAG TCC CCA    2260
Glu Lys Ser Arg Val Ala Ile Leu Lys Ala Asn Leu Arg Lys Ser Pro
650                 655                 660                 665

GTT GCC AAG GAT GTG GAC TTG GAG TTC CTG GCT AAA ATG ACT AAT GGC    2308
Val Ala Lys Asp Val Asp Leu Glu Phe Leu Ala Lys Met Thr Asn Gly
                670                 675                 680

TTC TCT GGA GCT GAC CTG ACA GAG ATT TGC CAG CGT GCT TGC AAG CTG    2356
Phe Ser Gly Ala Asp Leu Thr Glu Ile Cys Gln Arg Ala Cys Lys Leu
            685                 690                 695

GCC ATC CGT GAA TCC ATC GAG AGT GAG ATT AGG CGA GAA CGA GAG AGG    2404
Ala Ile Arg Glu Ser Ile Glu Ser Glu Ile Arg Arg Glu Arg Glu Arg
        700                 705                 710

CAG ACA AAC CCA TCA GCC ATG GAG GTA GAA GAG GAT GAT CCA GTG CCT    2452
Gln Thr Asn Pro Ser Ala Met Glu Val Glu Glu Asp Asp Pro Val Pro
    715                 720                 725

GAG ATC CGT CGA GAT CAC TTT GAA GAA GCC ATG CGC TTT GCG CGC CGT    2500
Glu Ile Arg Arg Asp His Phe Glu Glu Ala Met Arg Phe Ala Arg Arg
730                 735                 740                 745

TCT GTC AGT GAC AAT GAC ATT CGG AAG TAT GAG ATG TTT GCC CAG ACC    2548
Ser Val Ser Asp Asn Asp Ile Arg Lys Tyr Glu Met Phe Ala Gln Thr
                750                 755                 760

CTT CAG CAG AGT CGG GGC TTT GGC AGC TTC AGA TTC CCT TCA GGG AAC    2596
Leu Gln Gln Ser Arg Gly Phe Gly Ser Phe Arg Phe Pro Ser Gly Asn
```

```
                    765              770              775
CAG GGT GGA GCT GGC CCC AGT CAG GGC AGT GGA GGC GGC ACA GGT GGC    2644
Gln Gly Gly Ala Gly Pro Ser Gln Gly Ser Gly Gly Gly Thr Gly Gly
            780              785              790

AGT GTA TAC ACA GAA GAC AAT GAT GAT GAC CTG TAT GGC TAAGTGGTGG    2693
Ser Val Tyr Thr Glu Asp Asn Asp Asp Asp Leu Tyr Gly
    795              800              805

TGGCCAGCGT GCAGTGAGCT GGCCTGCCTG GACCTTGTTC CCTGGGGGTG GGGGCGCTTG    2753

CCCAGGAGAG GGACCAGGGG TGCGCCCACA GCCTGCTCCA TTCTCCAGTC TGAACAGTTC    2813

AGCTACAGTC TGACTCTGGA CAGGGTGTTT CTGTTGCAAA ATACAAAAC AAAAGCGATA     2873

AAATTAAAGC GATTTTCATT TGGAAAAAAA AAAAAAAAA AAAAAAAAG GGCGGCCGC      2932
```

(2) INFORMATION FOR SEQ ID NO:6:

(i) SEQUENCE CHARACTERISTICS:
        (A) LENGTH: 806 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ala Ser Gly Ala Asp Ser Lys Gly Asp Asp Leu Ser Thr Ala Ile
 1               5                  10                  15

Leu Lys Gln Lys Asn Arg Pro Asn Arg Leu Ile Val Asp Glu Ala Ile
            20                  25                  30

Asn Glu Asp Asn Ser Val Val Ser Leu Ser Gln Pro Lys Met Asp Glu
        35                  40                  45

Leu Gln Leu Phe Arg Gly Asp Thr Val Leu Leu Lys Gly Lys Lys Arg
    50                  55                  60

Arg Glu Ala Val Cys Ile Val Leu Ser Asp Asp Thr Cys Ser Asp Glu
65                  70                  75                  80

Lys Ile Arg Met Asn Arg Val Val Arg Asn Asn Leu Arg Val Arg Leu
                85                  90                  95

Gly Asp Val Ile Ser Ile Gln Pro Cys Pro Asp Val Lys Tyr Gly Lys
            100                 105                 110

Arg Ile His Val Leu Pro Ile Asp Asp Thr Val Glu Gly Ile Thr Gly
        115                 120                 125

Asn Leu Phe Glu Val Tyr Leu Lys Pro Tyr Phe Leu Glu Ala Tyr Arg
    130                 135                 140

Pro Ile Arg Lys Gly Asp Ile Phe Leu Val Arg Gly Gly Met Arg Ala
145                 150                 155                 160

Val Glu Phe Lys Val Val Glu Thr Asp Pro Ser Pro Tyr Cys Ile Val
                165                 170                 175

Ala Pro Asp Thr Val Ile His Cys Glu Gly Glu Pro Ile Lys Arg Glu
            180                 185                 190

Asp Glu Glu Glu Ser Leu Asn Glu Val Gly Tyr Asp Asp Ile Gly Gly
        195                 200                 205

Cys Arg Lys Gln Leu Ala Gln Ile Lys Glu Met Val Glu Leu Pro Leu
    210                 215                 220

Arg His Pro Ala Leu Phe Lys Ala Ile Gly Val Lys Pro Pro Arg Gly
225                 230                 235                 240

Ile Leu Leu Tyr Gly Pro Pro Gly Thr Gly Lys Thr Leu Ile Ala Arg
                245                 250                 255

Ala Val Ala Asn Glu Thr Gly Ala Phe Phe Phe Leu Ile Asn Gly Pro
```

-continued

```
                  260               265                270
        Glu Ile Met Ser Lys Leu Ala Gly Glu Ser Glu Ser Asn Leu Arg Lys
                275                 280                285
        Ala Phe Glu Glu Ala Glu Lys Asn Ala Pro Ala Ile Ile Phe Ile Asp
                290                 295                300
        Glu Leu Asp Ala Ile Ala Pro Lys Arg Glu Lys Thr His Gly Glu Val
        305                 310                315                320
        Glu Arg Arg Ile Val Ser Gln Leu Leu Thr Leu Met Asp Gly Leu Lys
                        325                 330                335
        Gln Arg Ala His Val Ile Val Met Ala Ala Thr Asn Arg Pro Asn Ser
                        340                 345                350
        Ile Asp Pro Ala Leu Arg Arg Phe Gly Arg Phe Asp Arg Glu Val Asp
                355                 360                365
        Ile Gly Ile Pro Asp Ala Thr Gly Arg Leu Glu Ile Leu Gln Ile His
                370                 375                380
        Thr Lys Asn Met Lys Leu Ala Asp Asp Val Asp Leu Glu Gln Val Ala
        385                 390                395                400
        Asn Glu Thr His Gly His Val Gly Ala Asp Leu Ala Ala Leu Cys Ser
                        405                 410                415
        Glu Ala Ala Leu Gln Ala Ile Arg Lys Lys Met Asp Leu Ile Asp Leu
                420                 425                430
        Glu Asp Glu Thr Ile Asp Ala Glu Val Met Asn Ser Leu Ala Val Thr
                435                 440                445
        Met Asp Asp Phe Arg Trp Ala Leu Ser Gln Ser Asn Pro Ser Ala Leu
                450                 455                460
        Arg Glu Thr Val Val Glu Val Pro Gln Val Thr Trp Glu Asp Ile Gly
        465                 470                475                480
        Gly Leu Glu Asp Val Lys Arg Glu Leu Gln Glu Leu Val Gln Tyr Pro
                        485                 490                495
        Val Glu His Pro Asp Lys Phe Leu Lys Phe Gly Met Thr Pro Ser Lys
                        500                 505                510
        Gly Val Leu Phe Tyr Gly Pro Pro Gly Cys Gly Lys Thr Leu Leu Ala
                515                 520                525
        Lys Ala Ile Ala Asn Glu Cys Gln Ala Asn Phe Ile Ser Ile Lys Gly
                530                 535                540
        Pro Glu Leu Leu Thr Met Trp Phe Gly Glu Ser Glu Ala Asn Val Arg
        545                 550                555                560
        Glu Ile Phe Asp Lys Ala Arg Gln Ala Ala Pro Cys Val Leu Phe Phe
                        565                 570                575
        Asp Glu Leu Asp Ser Ile Ala Lys Ala Arg Gly Asn Ile Gly Asp
                        580                 585                590
        Gly Gly Gly Ala Ala Asp Arg Val Ile Asn Gln Ile Leu Thr Glu Met
                595                 600                605
        Asp Gly Met Ser Thr Lys Lys Asn Val Phe Ile Ile Gly Ala Thr Asn
                610                 615                620
        Arg Pro Asp Ile Ile Asp Pro Ala Ile Leu Arg Pro Gly Arg Leu Asp
        625                 630                635                640
        Gln Leu Ile Tyr Ile Pro Leu Pro Asp Glu Lys Ser Arg Val Ala Ile
                        645                 650                655
        Leu Lys Ala Asn Leu Arg Lys Ser Pro Val Ala Lys Asp Val Asp Leu
                        660                 665                670
        Glu Phe Leu Ala Lys Met Thr Asn Gly Phe Ser Gly Ala Asp Leu Thr
                675                 680                685
```

```
Glu Ile Cys Gln Arg Ala Cys Lys Leu Ala Ile Arg Glu Ser Ile Glu
    690                 695                 700

Ser Glu Ile Arg Arg Glu Arg Glu Arg Gln Thr Asn Pro Ser Ala Met
705                 710                 715                 720

Glu Val Glu Glu Asp Asp Pro Val Pro Glu Ile Arg Arg Asp His Phe
                725                 730                 735

Glu Glu Ala Met Arg Phe Ala Arg Arg Ser Val Ser Asp Asn Asp Ile
            740                 745                 750

Arg Lys Tyr Glu Met Phe Ala Gln Thr Leu Gln Gln Ser Arg Gly Phe
            755                 760                 765

Gly Ser Phe Arg Phe Pro Ser Gly Asn Gln Gly Ala Gly Pro Ser
770                 775                 780

Gln Gly Ser Gly Gly Gly Thr Gly Gly Ser Val Tyr Thr Glu Asp Asn
785                 790                 795                 800

Asp Asp Asp Leu Tyr Gly
            805
```

(2) INFORMATION FOR SEQ ID NO:7:

(i) SEQUENCE CHARACTERISTICS:
        (A) LENGTH: 1491 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 82..792

(xi) SEQUENCE DESCRIPTION: SEQ ID NO:7:

```
GGACGCGTGG GGGACGGTCT GGGGCAGCCC AGCAGCGGCT GACCCTCTGC CTGCGGGGAA        60

GGGAGTCGCC AGGCGGCCGT C ATG GCG GTG TCG GAG AGC CAG CTC AAG AAA        111
                       Met Ala Val Ser Glu Ser Gln Leu Lys Lys
                        1               5                  10

ATG GTG TCC AAG TAC AAA TAC AGA GAC CTA ACT GTA CGT GAA ACT GTC        159
Met Val Ser Lys Tyr Lys Tyr Arg Asp Leu Thr Val Arg Glu Thr Val
             15                  20                  25

AAT GTT ATT ACT CTA TAC AAA GAT CTC AAA CCT GTG TTG GAT TCA TAT        207
Asn Val Ile Thr Leu Tyr Lys Asp Leu Lys Pro Val Leu Asp Ser Tyr
         30                  35                  40

GTT TTT AAC GAT GGC AGT TCC AGG GAA CTA ATG AAC CTC ACT GGA ACA        255
Val Phe Asn Asp Gly Ser Ser Arg Glu Leu Met Asn Leu Thr Gly Thr
     45                  50                  55

ATC CCT GTG CCT TAT AGA GGT AAT ACA TAC AAT ATT CCA ATA TGC CTA        303
Ile Pro Val Pro Tyr Arg Gly Asn Thr Tyr Asn Ile Pro Ile Cys Leu
 60                  65                  70

TGG CTA CTG GAC ACA TAC CCA TAT AAT CCC CCT ATC TGT TTT GTT AAG        351
Trp Leu Leu Asp Thr Tyr Pro Tyr Asn Pro Pro Ile Cys Phe Val Lys
 75                  80                  85                  90

CCT ACT AGT TCA ATG ACT ATT AAA ACA GGA AAG CAT GTT GAT GCA AAT        399
Pro Thr Ser Ser Met Thr Ile Lys Thr Gly Lys His Val Asp Ala Asn
                 95                 100                 105

GGG AAG ATA TAT CTT CCT TAT CTA CAT GAA TGG AAA CAC CCA CAG TCA        447
Gly Lys Ile Tyr Leu Pro Tyr Leu His Glu Trp Lys His Pro Gln Ser
             110                 115                 120

GAC TTG TTG GGG CTT ATT CAG GTC ATG ATT GTG TA TTT GGA GAT GAA        495
Asp Leu Leu Gly Leu Ile Gln Val Met Ile Val Val Phe Gly Asp Glu
         125                 130                 135
```

```
CCT CCA GTC TTC TCT CGT CCT ATT TCG GCA TCC TAT CCG CCA TAC CAG      543
Pro Pro Val Phe Ser Arg Pro Ile Ser Ala Ser Tyr Pro Pro Tyr Gln
        140                 145                 150

GCA ACG GGG CCA CCA AAT ACT TCC TAC ATG CCA GGC ATG CCA GGT GGA      591
Ala Thr Gly Pro Pro Asn Thr Ser Tyr Met Pro Gly Met Pro Gly Gly
155                 160                 165                 170

ATC TCT CCA TAC CCA TCC GGA TAC CCT CCC AAT CCC AGT GGT TAC CCA      639
Ile Ser Pro Tyr Pro Ser Gly Tyr Pro Pro Asn Pro Ser Gly Tyr Pro
            175                 180                 185

GGC TGT CCT TAC CCA CCT GGT GGT CCA TAT CCT GCC ACA ACA AGT TCT      687
Gly Cys Pro Tyr Pro Pro Gly Gly Pro Tyr Pro Ala Thr Thr Ser Ser
        190                 195                 200

CAG TAC CCT TCT CAG CCT CCT GTA CCA CTG TTG GTC CCA GTA GGG ATG      735
Gln Tyr Pro Ser Gln Pro Pro Val Pro Leu Leu Val Pro Val Gly Met
    205                 210                 215

GCA CAA TCA GCG AGG ACA CCA TCC GAG CCT CTC TCA TCT CTG CGG TCA      783
Ala Gln Ser Ala Arg Thr Pro Ser Glu Pro Leu Ser Ser Leu Arg Ser
220                 225                 230

GTG ACA AAC TGAGATGGCG GATGAAGGAG GAAATGGATC GTGCCCAGGC              832
Val Thr Asn
235

AGAGCTCAAT GCCTTGAAAC GAACAGAAGA AGACCTGAAA AAGGGTCACC AGAAACTGGA    892

AGAGATGGTT ACCCGTTTAG ATCAAGAAGT AGCCGAGGTT GATAAAAACA TAGAACTTTT    952

GAAAAAGAAG GATGAAGAAC TCAGTTCTGC TCTGGAAAAA ATGGAAAATC AGTCTGAAAA    1012

CAATGATATC GATGAAGTTA TCATTCCCAC AGCTCCCTTA TACAAACAGA TCCTGAATCT    1072

GTATGCAGAA GAAACGCTA TTGAAGCACA TATCTTTTAC TTGGGAGAAG CCTTGAGAAG     1132

GGGCGTGATA GACCTGGATG TCTTCCTGAA GCATGTATCT TCTGTCCCGT AAACAGTTCC    1192

AGCTGAGGGC ACTAATGCAA AAAGCAAAAG ACTGCCGGTC TCGTGACCTC TACTGACTTC    1252

TCTGATACCA GCTGGAGGTT GAGCTCTTCT TAAAGTAGTC TCTCTTCCTT TTATCAGTAG    1312

GTGCCCAGAA TAAGTTATTG CAGTTTATCA TTCAAGTGTA AAATATTTTG AATCAATAAT    1372

ATATTTTCTG TTTTCTTTTG GTAAAAGACT GGCTTTTTAA TGCACTTTCT ATCCTCTGTA    1432

AACTTTTGTG CTGAATGTTG GGACTGCTAA ATAAAATTTG TTGCATAAAA AAAAAAAA     1491

(2) INFORMATION FOR SEQ ID NO:8:

(i) SEQUENCE CHARACTERISTICS:
        (A) LENGTH: 237 amino acids
        (B) TYPE: amino acid
        (D) TOPOLOGY: linear (ii) MOLECULE TYPE: protein (xi) SEQUENCE DESCRIPTION: SEQ ID NO:8:

Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
                20                  25                  30

Lys Asp Leu Lys Pro Val Leu Asp Ser Tyr Val Phe Asn Asp Gly Ser
            35                  40                  45

Ser Arg Glu Leu Met Asn Leu Thr Gly Thr Ile Pro Val Pro Tyr Arg
        50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
```

```
                   85                  90                  95
Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
            115                 120                 125

Gln Val Met Ile Val Phe Gly Asp Glu Pro Pro Val Phe Ser Arg
130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
            195                 200                 205

Pro Val Pro Leu Leu Val Pro Val Gly Met Ala Gln Ser Ala Arg Thr
210                 215                 220

Pro Ser Glu Pro Leu Ser Ser Leu Arg Ser Val Thr Asn
225                 230                 235

(2) INFORMATION FOR SEQ ID NO:9:

(i) SEQUENCE CHARACTERISTICS:
        (A) LENGTH: 1908 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 334..1842

(ix) FEATURE:
        (A) NAME/KEY: misc_feature
        (B) LOCATION: 799
        (D) OTHER INFORMATION: /note= "nucleotides 799 and 821
            designated C, may be A, C, G, or T"

(ix) FEATURE:
        (A) NAME/KEY: misc_feature
        (B) LOCATION: 1128
        (D) OTHER INFORMATION: /note= "nucleotide 1128 designated
            C, may be A or C"

(xi) SEQUENCE DESCRIPTION: SEQ ID NO:9:

TTTCCCGGGA GCCTGACCCG CCCCTGACGT CGCCTTTCCC GTCTCCGCAG GGTCCGGCCT      60

GCGCCTTCCC GCCAGGCCTG GACACTGGTT CAACACCTGT GACTTCATGT GTGCGCGCCG    120

GCCACACCTG CAGTCACACC TGTAGCCCCC TCTGCCAAGA GATCCATACC GAGGCAGCGT    180

CGGTGGCTAC AAGCCCTCAG TCCACACCTG TGGACACCTG TGACACCTGG CCACACGACC    240

TGTGGCCGCG GCCTGGCGTC TGCTGCGACA GGAGCCCTTA CCTCCCCTGT TATAACACCT    300

GACCGCCACC TAACTGCCCC TGCAGAAGGA GCA ATG GCC TTG GCT CCT GAG AGG     354
                                   Met Ala Leu Ala Pro Glu Arg
                                    1               5

GCA GCC CCA CGC GTG CTG TTC GGA GAG TGG CTC CTT GGA GAG ATC AGC      402
Ala Ala Pro Arg Val Leu Phe Gly Glu Trp Leu Leu Gly Glu Ile Ser
         10                  15                  20

AGC GGC TGC TAT GAG GGG CTG CAG TGG CTG GAC GAG GCC CGC ACC TGT      450
Ser Gly Cys Tyr Glu Gly Leu Gln Trp Leu Asp Glu Ala Arg Thr Cys
 25                  30                  35
```

```
TTC CGC GTG CCC TGG AAG CAC TTC GCG CGC AAG GAC CTG AGC GAG GCC    498
Phe Arg Val Pro Trp Lys His Phe Ala Arg Lys Asp Leu Ser Glu Ala
 40              45                  50                  55

GAC GCG CGC ATC TTC AAG GCC TGG GCT GTG GCC CGC GGC AGG TGG CCG    546
Asp Ala Arg Ile Phe Lys Ala Trp Ala Val Ala Arg Gly Arg Trp Pro
                 60                  65                  70

CCT AGC AGC AGG GGA GGT GGC CCG CCC CCC GAG GCT GAG ACT GCG GAG    594
Pro Ser Ser Arg Gly Gly Gly Pro Pro Pro Glu Ala Glu Thr Ala Glu
             75                  80                  85

CGC GCC GGC TGG AAA ACC AAC TTC CGC TGC GCA CTG CGC AGC ACG CGT    642
Arg Ala Gly Trp Lys Thr Asn Phe Arg Cys Ala Leu Arg Ser Thr Arg
         90                  95                 100

CGC TTC GTG ATG CTG CGG GAT AAC TCG GGG GAC CCG GCC GAC CCG CAC    690
Arg Phe Val Met Leu Arg Asp Asn Ser Gly Asp Pro Ala Asp Pro His
    105                 110                 115

AAG GTG TAC GCG CTC AGC CGG GAG CTG TGC TGG CGA GAA GGC CCA GGC    738
Lys Val Tyr Ala Leu Ser Arg Glu Leu Cys Trp Arg Glu Gly Pro Gly
120                 125                 130                 135

ACG GAC CAG ACT GAG GCA GAG GCC CCC GCA GCT GTC CCA CCA CCA CAG    786
Thr Asp Gln Thr Glu Ala Glu Ala Pro Ala Ala Val Pro Pro Pro Gln
                140                 145                 150

GGT GGG CCC CCA CGG CCA TTC CTG GCA CAC ACA CCT GCT GGA CTC CAA    834
Gly Gly Pro Pro Arg Pro Phe Leu Ala His Thr Pro Ala Gly Leu Gln
            155                 160                 165

GCC CCA GGC CCC CTC CCT GCC CCA GCT GGT GAC AAG GGG GAC CTC CTG    882
Ala Pro Gly Pro Leu Pro Ala Pro Ala Gly Asp Lys Gly Asp Leu Leu
        170                 175                 180

CTC CAG GCA GTG CAA CAG AGC TGC CTG GCA GAC CAT CTG CTG ACA GCG    930
Leu Gln Ala Val Gln Gln Ser Cys Leu Ala Asp His Leu Leu Thr Ala
    185                 190                 195

TCA TGG GGG GCA GAT CCA GTC CCA ACC AAG GCT CCT GGA GAG GGA CAA    978
Ser Trp Gly Ala Asp Pro Val Pro Thr Lys Ala Pro Gly Glu Gly Gln
200                 205                 210                 215

GAA GGG CTT CCC CTG ACT GGG GCC TGT GCT GGA GGC CCA GGG CTC CCT   1026
Glu Gly Leu Pro Leu Thr Gly Ala Cys Ala Gly Gly Pro Gly Leu Pro
                220                 225                 230

GCT GGG GAG CTG TAC GGG TGG GCA GTA GAG AAG ACC CCC AGC CCC GGG   1074
Ala Gly Glu Leu Tyr Gly Trp Ala Val Glu Lys Thr Pro Ser Pro Gly
            235                 240                 245

CCC CAG CCC GCG GCA CTA ACG ACA GGC GAG GCC GCG GCC CCA GAG TCC   1122
Pro Gln Pro Ala Ala Leu Thr Thr Gly Glu Ala Ala Ala Pro Glu Ser
        250                 255                 260

CCG CAC CAG GCA GAG CCG TAC CTG TCA CCC TCC CCA AGC GCC TGC ACC   1170
Pro His Gln Ala Glu Pro Tyr Leu Ser Pro Ser Pro Ser Ala Cys Thr
    265                 270                 275

GCG GTG CAA GAG CCC AGC CCA GGG GCG CTG GAC GTG ACC ATC ATG TAC   1218
Ala Val Gln Glu Pro Ser Pro Gly Ala Leu Asp Val Thr Ile Met Tyr
280                 285                 290                 295

AAG GGC CGC ACG GTG CTG CAG AAG GTG GTG GGA CAC CCG AGC TGC ACG   1266
Lys Gly Arg Thr Val Leu Gln Lys Val Val Gly His Pro Ser Cys Thr
                300                 305                 310

TTC CTA TAC GGC CCC CCA GAC CCA GCT GTC CGG GCC ACA GAC CCC CAG   1314
Phe Leu Tyr Gly Pro Pro Asp Pro Ala Val Arg Ala Thr Asp Pro Gln
            315                 320                 325

CAG GTA GCA TTC CCC AGC CCT GCC GAG CTC CCG GAC CAG AAG CAG CTG   1362
Gln Val Ala Phe Pro Ser Pro Ala Glu Leu Pro Asp Gln Lys Gln Leu
        330                 335                 340

CGC TAC ACG GAG GAA CTG CTG CGG CAC GTG GCC CCT GGG TTG CAC CTG   1410
Arg Tyr Thr Glu Glu Leu Leu Arg His Val Ala Pro Gly Leu His Leu
```

-continued

```
                345                 350                355
GAG CTT CGG GGG CCA CAG CTG TGG GCC CGG CGC ATG GGC AAG TGC AAG    1458
Glu Leu Arg Gly Pro Gln Leu Trp Ala Arg Arg Met Gly Lys Cys Lys
360                 365                 370                 375

GTG TAC TGG GAG GTG GGC GGA CCC CCA GGC TCC GCC AGC CCC TCC ACC    1506
Val Tyr Trp Glu Val Gly Gly Pro Pro Gly Ser Ala Ser Pro Ser Thr
                380                 385                 390

CCA GCC TGC CTG CTG CCT CGG AAC TGT GAC ACC CCC ATC TTC GAC TTC    1554
Pro Ala Cys Leu Leu Pro Arg Asn Cys Asp Thr Pro Ile Phe Asp Phe
            395                 400                 405

AGA GTC TTC TTC CAA GAG CTG GTG GAA TTC CGG GCA CGG CAG CGC CGT    1602
Arg Val Phe Phe Gln Glu Leu Val Glu Phe Arg Ala Arg Gln Arg Arg
        410                 415                 420

GGC TCC CCA CGC TAT ACC ATC TAC CTG GGC TTC GGG CAG GAC CTG TCA    1650
Gly Ser Pro Arg Tyr Thr Ile Tyr Leu Gly Phe Gly Gln Asp Leu Ser
    425                 430                 435

GCT GGG AGG CCC AAG GAG AAG AGC CTG GTC CTG GTG AAG CTG GAA CCC    1698
Ala Gly Arg Pro Lys Glu Lys Ser Leu Val Leu Val Lys Leu Glu Pro
440                 445                 450                 455

TGG CTG TGC CGA GTG CAC CTA GAG GGC ACG CAG CGT GAG GGT GTG TCT    1746
Trp Leu Cys Arg Val His Leu Glu Gly Thr Gln Arg Glu Gly Val Ser
                460                 465                 470

TCC CTG GAT AGC AGC AGC CTC AGC CTC TGC CTG TCC AGC GCC AAC AGC    1794
Ser Leu Asp Ser Ser Ser Leu Ser Leu Cys Leu Ser Ser Ala Asn Ser
            475                 480                 485

CTC TAT GAC GAC ATC GAG TGC TTC CTT ATG GAG CTG GAG CAG CCC GCC    1842
Leu Tyr Asp Asp Ile Glu Cys Phe Leu Met Glu Leu Glu Gln Pro Ala
        490                 495                 500

TAGAACCCAG TCTAATGAGA ACTCCAGAAA GCTGGAGCAG CCCACCTAGA GCTGGCCGCG    1902

GCCGCT                                                              1908
```

(2) INFORMATION FOR SEQ ID NO:10:

(i) SEQUENCE CHARACTERISTICS:
        (A) LENGTH: 503 amino acids
        (B) TYPE: amino acid
        (D) TOPOLOGY: linear (ii) MOLECULE TYPE: protein (xi) SEQUENCE DESCRIPTION: SEQ ID NO:10:

```
Met Ala Leu Ala Pro Glu Arg Ala Ala Pro Arg Val Leu Phe Gly Glu
 1               5                  10                  15

Trp Leu Leu Gly Glu Ile Ser Ser Gly Cys Tyr Glu Gly Leu Gln Trp
                20                  25                  30

Leu Asp Glu Ala Arg Thr Cys Phe Arg Val Pro Trp Lys His Phe Ala
            35                  40                  45

Arg Lys Asp Leu Ser Glu Ala Asp Ala Arg Ile Phe Lys Ala Trp Ala
        50                  55                  60

Val Ala Arg Gly Arg Trp Pro Pro Ser Arg Gly Gly Pro Pro
65                  70                  75                  80

Pro Glu Ala Glu Thr Ala Glu Arg Ala Gly Trp Lys Thr Asn Phe Arg
                85                  90                  95

Cys Ala Leu Arg Ser Thr Arg Arg Phe Val Met Leu Arg Asp Asn Ser
                100                 105                 110

Gly Asp Pro Ala Asp Pro His Lys Val Tyr Ala Leu Ser Arg Glu Leu
            115                 120                 125

Cys Trp Arg Glu Gly Pro Gly Thr Asp Gln Thr Glu Ala Glu Ala Pro
```

```
            130                 135                 140
Ala Ala Val Pro Pro Pro Gln Gly Gly Pro Pro Arg Pro Phe Leu Ala
145                 150                 155                 160

His Thr Pro Ala Gly Leu Gln Ala Pro Gly Pro Leu Pro Ala Pro Ala
                165                 170                 175

Gly Asp Lys Gly Asp Leu Leu Leu Gln Ala Val Gln Gln Ser Cys Leu
            180                 185                 190

Ala Asp His Leu Leu Thr Ala Ser Trp Gly Ala Asp Pro Val Pro Thr
        195                 200                 205

Lys Ala Pro Gly Glu Gly Gln Glu Gly Leu Pro Leu Thr Gly Ala Cys
    210                 215                 220

Ala Gly Gly Pro Gly Leu Pro Ala Gly Glu Leu Tyr Gly Trp Ala Val
225                 230                 235                 240

Glu Lys Thr Pro Ser Pro Gly Pro Gln Pro Ala Ala Leu Thr Thr Gly
                245                 250                 255

Glu Ala Ala Ala Pro Glu Ser Pro His Gln Ala Glu Pro Tyr Leu Ser
            260                 265                 270

Pro Ser Pro Ser Ala Cys Thr Ala Val Gln Glu Pro Ser Pro Gly Ala
        275                 280                 285

Leu Asp Val Thr Ile Met Tyr Lys Gly Arg Thr Val Leu Gln Lys Val
    290                 295                 300

Val Gly His Pro Ser Cys Thr Phe Leu Tyr Gly Pro Pro Asp Pro Ala
305                 310                 315                 320

Val Arg Ala Thr Asp Pro Gln Gln Val Ala Phe Pro Ser Pro Ala Glu
                325                 330                 335

Leu Pro Asp Gln Lys Gln Leu Arg Tyr Thr Glu Glu Leu Leu Arg His
            340                 345                 350

Val Ala Pro Gly Leu His Leu Glu Leu Arg Gly Pro Gln Leu Trp Ala
        355                 360                 365

Arg Arg Met Gly Lys Cys Lys Val Tyr Trp Glu Val Gly Gly Pro Pro
    370                 375                 380

Gly Ser Ala Ser Pro Ser Thr Pro Ala Cys Leu Leu Pro Arg Asn Cys
385                 390                 395                 400

Asp Thr Pro Ile Phe Asp Phe Arg Val Phe Phe Gln Glu Leu Val Glu
                405                 410                 415

Phe Arg Ala Arg Gln Arg Arg Gly Ser Pro Arg Tyr Thr Ile Tyr Leu
            420                 425                 430

Gly Phe Gly Gln Asp Leu Ser Ala Gly Arg Pro Lys Glu Lys Ser Leu
        435                 440                 445

Val Leu Val Lys Leu Glu Pro Trp Leu Cys Arg Val His Leu Glu Gly
    450                 455                 460

Thr Gln Arg Glu Gly Val Ser Ser Leu Asp Ser Ser Leu Ser Leu
465                 470                 475                 480

Cys Leu Ser Ser Ala Asn Ser Leu Tyr Asp Asp Ile Glu Cys Phe Leu
                485                 490                 495

Met Glu Leu Glu Gln Pro Ala
            500

(2) INFORMATION FOR SEQ ID NO:11:

(i) SEQUENCE CHARACTERISTICS:
        (A) LENGTH: 1503 base pairs
        (B) TYPE: nucleic acid
        (C) STRANDEDNESS: single
        (D) TOPOLOGY: linear
```

(ii) MOLECULE TYPE: cDNA (ix) FEATURE:
    (A) NAME/KEY: CDS
    (B) LOCATION: 25..1503

(xi) SEQUENCE DESCRIPTION: SEQ ID NO:11:

```
GTCGACCCAC GCGTCCGGGA CAAA ATG GCG AAG ATC GCC AAG ACT CAC GAA          51
                           Met Ala Lys Ile Ala Lys Thr His Glu
                            1               5

GAT ATT GAA GCA CAG ATT CGA GAA ATT CAA GGC AAG AAG GCA GCT CTT         99
Asp Ile Glu Ala Gln Ile Arg Glu Ile Gln Gly Lys Lys Ala Ala Leu
 10              15                  20                  25

GAT GAA GCT CAA GGA GTG GGC CTC GAT TCT ACA GGT TAT TAT GAC CAG         147
Asp Glu Ala Gln Gly Val Gly Leu Asp Ser Thr Gly Tyr Tyr Asp Gln
                 30                  35                  40

GAA ATT TAT GGT GGA AGT GAC AGC AGA TTT GCT GGA TAC GTG ACA TCA         195
Glu Ile Tyr Gly Gly Ser Asp Ser Arg Phe Ala Gly Tyr Val Thr Ser
             45                  50                  55

ATT GCT GCA ACT GAA CTT GAA GAT GAT GAC GAT GAC TAT TCA TCA TCT         243
Ile Ala Ala Thr Glu Leu Glu Asp Asp Asp Asp Asp Tyr Ser Ser Ser
         60                  65                  70

ACG AGT TTG CTT GGT CAG AAG AAG CCA GGA TAT CAT GCC CCT GTG GCA         291
Thr Ser Leu Leu Gly Gln Lys Lys Pro Gly Tyr His Ala Pro Val Ala
     75                  80                  85

TTG CTT AAT GAT ATA CCA CAG TCA ACA GAA CAG TAT GAT CCA TTT GCT         339
Leu Leu Asn Asp Ile Pro Gln Ser Thr Glu Gln Tyr Asp Pro Phe Ala
 90                  95                 100                 105

GAG CAC AGA CCT CCA AAG ATT GCA GAC CGG GAA GAT GAA TAC AAA AAG         387
Glu His Arg Pro Pro Lys Ile Ala Asp Arg Glu Asp Glu Tyr Lys Lys
                110                 115                 120

CAT AGG CGG ACC ATG ATA ATT TCC CCA GAG CGT CTT GAT CCT TTT GCA         435
His Arg Arg Thr Met Ile Ile Ser Pro Glu Arg Leu Asp Pro Phe Ala
            125                 130                 135

GAT GGA GGG AAG ACC CCT GAT CCT AAA ATG AAT GCT AGG ACT TAC ATG         483
Asp Gly Gly Lys Thr Pro Asp Pro Lys Met Asn Ala Arg Thr Tyr Met
        140                 145                 150

GAT GTT ATG CGA GAA CAA CAC TTG ACT AAA GAA GAA CGA GAA ATT AGG         531
Asp Val Met Arg Glu Gln His Leu Thr Lys Glu Glu Arg Glu Ile Arg
    155                 160                 165

CAA CAG CTA GCA GAA AAA GCT AAA GCT GGA GAA CTA AAA GTC GTC AAT         579
Gln Gln Leu Ala Glu Lys Ala Lys Ala Gly Glu Leu Lys Val Val Asn
170                 175                 180                 185

GGA GCA GCA GCG TCC CAG CCT CCA TCA AAA CGA AAA CGG CGT TGG GAT         627
Gly Ala Ala Ala Ser Gln Pro Pro Ser Lys Arg Lys Arg Arg Trp Asp
                190                 195                 200

CAA ACA GCT GAT CAG ACT CCT GGT GCC ACT CCC AAA AAA CTA TCA AGT         675
Gln Thr Ala Asp Gln Thr Pro Gly Ala Thr Pro Lys Lys Leu Ser Ser
            205                 210                 215

TGG GAT CAG GCA GAG ACC CCT GGG CAT ACT CCT TCC TTA AGA TGG GAT         723
Trp Asp Gln Ala Glu Thr Pro Gly His Thr Pro Ser Leu Arg Trp Asp
        220                 225                 230

GAG ACA CCA GGT CGT GCA AAG GGA AGC GAG ACT CCT GGA GCA ACC CCA         771
Glu Thr Pro Gly Arg Ala Lys Gly Ser Glu Thr Pro Gly Ala Thr Pro
    235                 240                 245

GGC TCA AAA ATA TGG GAT CCT ACA CCT AGC CAC ACA CCA GCG GGA GCT         819
Gly Ser Lys Ile Trp Asp Pro Thr Pro Ser His Thr Pro Ala Gly Ala
250                 255                 260                 265

GCT ACT CCT GGA CGA GGT GAT ACA CCA GGC CAT GCG ACA CCC GGC CAT         867
Ala Thr Pro Gly Arg Gly Asp Thr Pro Gly His Ala Thr Pro Gly His
```

|  |  |  |  |  |  |  |  |  |  |  |  |  |  |  |  |
|---|---|---|---|---|---|---|---|---|---|---|---|---|---|---|---|
|  |  |  | 270 |  |  |  | 275 |  |  |  |  | 280 |  |  |  |
| GGA | GGC | GCA | ACT | TCC | AGT | GCT | CGT | AAA | AAC | AGA | TGG | GAT | GAA | ACC | CCC | 915 |
| Gly | Gly | Ala | Thr | Ser | Ser | Ala | Arg | Lys | Asn | Arg | Trp | Asp | Glu | Thr | Pro |  |
|  |  |  | 285 |  |  |  | 290 |  |  |  |  | 295 |  |  |  |  |
| AAA | ACA | GAG | AGA | GAT | ACT | CTT | GGG | CAT | GGA | AGT | GGA | TGG | GGT | GAG | ACT | 963 |
| Lys | Thr | Glu | Arg | Asp | Thr | Leu | Gly | His | Gly | Ser | Gly | Trp | Gly | Glu | Thr |  |
|  |  |  | 300 |  |  |  | 305 |  |  |  |  | 310 |  |  |  |  |
| CCT | CGA | ACA | GAT | CGA | GGC | GGA | GAT | TAT | ATT | GGT | GAA | ACA | CCG | ACT | CCT | 1011 |
| Pro | Arg | Thr | Asp | Arg | Gly | Gly | Asp | Tyr | Ile | Gly | Glu | Thr | Pro | Thr | Pro |  |
|  |  | 315 |  |  |  |  | 320 |  |  |  |  | 325 |  |  |  |  |
| GGA | GCC | AGT | AAA | AGA | AAC | TCA | CGG | TGG | GAT | GAA | ACA | CCA | GCT | AGT | CAG | 1059 |
| Gly | Ala | Ser | Lys | Arg | Asn | Ser | Arg | Trp | Asp | Glu | Thr | Pro | Ala | Ser | Gln |  |
| 330 |  |  |  |  | 335 |  |  |  |  | 340 |  |  |  |  | 345 |  |
| ATG | GGT | GGA | AGC | ACT | CCA | GTT | CTG | ACC | CCT | GGA | AAG | ACA | CCA | ATT | GGC | 1107 |
| Met | Gly | Gly | Ser | Thr | Pro | Val | Leu | Thr | Pro | Gly | Lys | Thr | Pro | Ile | Gly |  |
|  |  |  | 350 |  |  |  | 355 |  |  |  |  | 360 |  |  |  |  |
| ACA | CCA | GCC | ATG | AAC | ATG | GCT | ACC | CCT | ACT | CCA | GGT | CAC | ATA | ATG | AGT | 1155 |
| Thr | Pro | Ala | Met | Asn | Met | Ala | Thr | Pro | Thr | Pro | Gly | His | Ile | Met | Ser |  |
|  |  |  | 365 |  |  |  | 370 |  |  |  |  | 375 |  |  |  |  |
| ATG | ACT | CCT | GAA | CAG | CTT | CAG | GCT | TGG | CGG | TGG | GAA | AGA | GAA | ATT | GAT | 1203 |
| Met | Thr | Pro | Glu | Gln | Leu | Gln | Ala | Trp | Arg | Trp | Glu | Arg | Glu | Ile | Asp |  |
|  |  | 380 |  |  |  |  | 385 |  |  |  |  | 390 |  |  |  |  |
| GAG | AGA | AAT | CGC | CCA | CTT | TCT | GAT | GAG | GAA | TTA | GAT | GCT | ATG | TTC | CCA | 1251 |
| Glu | Arg | Asn | Arg | Pro | Leu | Ser | Asp | Glu | Glu | Leu | Asp | Ala | Met | Phe | Pro |  |
|  | 395 |  |  |  |  | 400 |  |  |  |  | 405 |  |  |  |  |  |
| GAA | GGA | TAT | AAG | GTA | CTT | CCT | CCT | CCA | GCT | GGT | TAT | GTT | CCT | ATT | CGA | 1299 |
| Glu | Gly | Tyr | Lys | Val | Leu | Pro | Pro | Pro | Ala | Gly | Tyr | Val | Pro | Ile | Arg |  |
| 410 |  |  |  |  | 415 |  |  |  |  | 420 |  |  |  |  | 425 |  |
| ACT | CCA | GCT | CGA | AAG | CTG | ACA | GCT | ACT | CCA | ACA | CCT | TTG | GGT | GGT | ATG | 1347 |
| Thr | Pro | Ala | Arg | Lys | Leu | Thr | Ala | Thr | Pro | Thr | Pro | Leu | Gly | Gly | Met |  |
|  |  |  | 430 |  |  |  | 435 |  |  |  |  | 440 |  |  |  |  |
| ACT | GGT | TTC | CAC | ATG | CAA | ACT | GAA | GAT | CGA | ACT | ATG | AAA | AGT | GTT | AAT | 1395 |
| Thr | Gly | Phe | His | Met | Gln | Thr | Glu | Asp | Arg | Thr | Met | Lys | Ser | Val | Asn |  |
|  |  |  | 445 |  |  |  | 450 |  |  |  |  | 455 |  |  |  |  |
| GAC | CAG | CCA | TCT | GGA | AAT | CTT | CCA | TTT | TTA | AAA | CCT | GAT | GAT | ATT | CAA | 1443 |
| Asp | Gln | Pro | Ser | Gly | Asn | Leu | Pro | Phe | Leu | Lys | Pro | Asp | Asp | Ile | Gln |  |
|  |  |  | 460 |  |  |  | 465 |  |  |  |  | 470 |  |  |  |  |
| TAC | TTT | GAT | AAA | CTA | TTG | GTT | GAT | GTT | GAT | GAA | TCA | ACA | CTT | AGT | CCA | 1491 |
| Tyr | Phe | Asp | Lys | Leu | Leu | Val | Asp | Val | Asp | Glu | Ser | Thr | Leu | Ser | Pro |  |
|  | 475 |  |  |  |  | 480 |  |  |  |  | 485 |  |  |  |  |  |
| GAA | GAG | CAA | AAA |  |  |  |  |  |  |  |  |  |  |  |  | 1503 |
| Glu | Glu | Gln | Lys |  |  |  |  |  |  |  |  |  |  |  |  |  |
| 490 |  |  |  |  |  |  |  |  |  |  |  |  |  |  |  |  |

(2) INFORMATION FOR SEQ ID NO:12:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO:12:

| Met | Ala | Lys | Ile | Ala | Lys | Thr | His | Glu | Asp | Ile | Glu | Ala | Gln | Ile | Arg |
|---|---|---|---|---|---|---|---|---|---|---|---|---|---|---|---|
| 1 |  |  |  | 5 |  |  |  |  | 10 |  |  |  |  | 15 |  |

| Glu | Ile | Gln | Gly | Lys | Lys | Ala | Ala | Leu | Asp | Glu | Ala | Gln | Gly | Val | Gly |
|---|---|---|---|---|---|---|---|---|---|---|---|---|---|---|---|
|  |  |  | 20 |  |  |  |  | 25 |  |  |  |  | 30 |  |  |

| Leu | Asp | Ser | Thr | Gly | Tyr | Tyr | Asp | Gln | Glu | Ile | Tyr | Gly | Gly | Ser | Asp |
|---|---|---|---|---|---|---|---|---|---|---|---|---|---|---|---|
|  |  | 35 |  |  |  |  | 40 |  |  |  |  | 45 |  |  |  |

-continued

```
Ser Arg Phe Ala Gly Tyr Val Thr Ser Ile Ala Ala Thr Glu Leu Glu
         50                  55                  60

Asp Asp Asp Asp Tyr Ser Ser Thr Ser Leu Leu Gly Gln Lys
 65              70                  75                  80

Lys Pro Gly Tyr His Ala Pro Val Ala Leu Leu Asn Asp Ile Pro Gln
                 85                  90                  95

Ser Thr Glu Gln Tyr Asp Pro Phe Ala Glu His Arg Pro Pro Lys Ile
            100                 105                 110

Ala Asp Arg Glu Asp Glu Tyr Lys Lys His Arg Arg Thr Met Ile Ile
            115                 120                 125

Ser Pro Glu Arg Leu Asp Pro Phe Ala Asp Gly Gly Lys Thr Pro Asp
        130                 135                 140

Pro Lys Met Asn Ala Arg Thr Tyr Met Asp Val Met Arg Glu Gln His
145                 150                 155                 160

Leu Thr Lys Glu Glu Arg Glu Ile Arg Gln Gln Leu Ala Glu Lys Ala
                165                 170                 175

Lys Ala Gly Glu Leu Lys Val Val Asn Gly Ala Ala Ser Gln Pro
                180                 185                 190

Pro Ser Lys Arg Lys Arg Arg Trp Asp Gln Thr Ala Asp Gln Thr Pro
        195                 200                 205

Gly Ala Thr Pro Lys Lys Leu Ser Ser Trp Asp Gln Ala Glu Thr Pro
    210                 215                 220

Gly His Thr Pro Ser Leu Arg Trp Asp Glu Thr Pro Gly Arg Ala Lys
225                 230                 235                 240

Gly Ser Glu Thr Pro Gly Ala Thr Pro Gly Ser Lys Ile Trp Asp Pro
                245                 250                 255

Thr Pro Ser His Thr Pro Ala Gly Ala Ala Thr Pro Gly Arg Gly Asp
                260                 265                 270

Thr Pro Gly His Ala Thr Pro Gly His Gly Gly Ala Thr Ser Ser Ala
            275                 280                 285

Arg Lys Asn Arg Trp Asp Glu Thr Pro Lys Thr Glu Arg Asp Thr Leu
        290                 295                 300

Gly His Gly Ser Gly Trp Gly Glu Thr Pro Arg Thr Asp Arg Gly Gly
305                 310                 315                 320

Asp Tyr Ile Gly Glu Thr Pro Thr Pro Gly Ala Ser Lys Arg Asn Ser
                325                 330                 335

Arg Trp Asp Glu Thr Pro Ala Ser Gln Met Gly Gly Ser Thr Pro Val
            340                 345                 350

Leu Thr Pro Gly Lys Thr Pro Ile Gly Thr Pro Ala Met Asn Met Ala
        355                 360                 365

Thr Pro Thr Pro Gly His Ile Met Ser Met Thr Pro Glu Gln Leu Gln
    370                 375                 380

Ala Trp Arg Trp Glu Arg Glu Ile Asp Glu Arg Asn Arg Pro Leu Ser
385                 390                 395                 400

Asp Glu Glu Leu Asp Ala Met Phe Pro Glu Gly Tyr Lys Val Leu Pro
                405                 410                 415

Pro Pro Ala Gly Tyr Val Pro Ile Arg Thr Pro Ala Arg Lys Leu Thr
            420                 425                 430

Ala Thr Pro Thr Pro Leu Gly Gly Met Thr Gly Phe His Met Gln Thr
        435                 440                 445

Glu Asp Arg Thr Met Lys Ser Val Asn Asp Gln Pro Ser Gly Asn Leu
450                 455                 460

Pro Phe Leu Lys Pro Asp Asp Ile Gln Tyr Phe Asp Lys Leu Leu Val
```

```
                465                 470                 475                 480
Asp Val Asp Glu Ser Thr Leu Ser Pro Glu Glu Gln Lys
                    485                 490

(2) INFORMATION FOR SEQ ID NO:13:

(i) SEQUENCE CHARACTERISTICS:
        (A) LENGTH: 1306 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:13:

Met Ala Lys Ile Ala Lys Thr His Glu Asp Ile Glu Ala Gln Ile Arg
 1               5                  10                  15

Glu Ile Gln Gly Lys Lys Ala Ala Leu Asp Glu Ala Gln Gly Val Gly
                20                  25                  30

Leu Asp Ser Thr Gly Tyr Tyr Asp Gln Glu Ile Tyr Gly Gly Ser Asp
            35                  40                  45

Ser Arg Phe Ala Gly Tyr Val Thr Ser Ile Ala Ala Thr Glu Leu Glu
50                  55                  60

Asp Asp Asp Asp Tyr Ser Ser Thr Ser Leu Leu Gly Gln Lys
65                  70                  75                  80

Lys Pro Gly Tyr His Ala Pro Val Ala Leu Leu Asn Asp Ile Pro Gln
                85                  90                  95

Ser Thr Glu Gln Tyr Asp Pro Phe Ala Glu His Arg Pro Pro Lys Ile
            100                 105                 110

Ala Asp Arg Glu Asp Glu Tyr Lys Lys His Arg Arg Thr Met Ile Ile
        115                 120                 125

Ser Pro Glu Arg Leu Asp Pro Phe Ala Asp Gly Gly Lys Thr Pro Asp
    130                 135                 140

Pro Lys Met Asn Val Arg Thr Tyr Met Asp Val Met Arg Glu Gln His
145                 150                 155                 160

Leu Thr Lys Glu Glu Arg Glu Ile Arg Gln Gln Leu Ala Glu Lys Ala
                165                 170                 175

Lys Ala Gly Glu Leu Lys Val Val Asn Gly Ala Ala Ser Gln Pro
            180                 185                 190

Pro Ser Lys Arg Lys Arg Arg Trp Asp Gln Thr Ala Asp Gln Thr Pro
        195                 200                 205

Gly Ala Thr Pro Lys Lys Leu Ser Ser Trp Asp Gln Ala Glu Thr Pro
    210                 215                 220

Gly His Thr Pro Ser Leu Arg Trp Asp Glu Thr Pro Gly Arg Ala Lys
225                 230                 235                 240

Gly Ser Glu Thr Pro Gly Ala Thr Pro Gly Ser Lys Ile Trp Asp Pro
                245                 250                 255

Thr Pro Ser His Thr Pro Ala Gly Ala Ala Thr Pro Gly Arg Gly Asp
            260                 265                 270

Thr Pro Gly His Ala Thr Pro Gly His Gly Gly Ala Thr Ser Ser Ala
        275                 280                 285

Arg Lys Asn Arg Trp Asp Glu Thr Pro Lys Thr Glu Arg Asp Thr Pro
    290                 295                 300

Gly His Gly Ser Gly Trp Ala Glu Thr Pro Arg Thr Asp Arg Gly Gly
305                 310                 315                 320

Asp Ser Ile Gly Glu Thr Pro Thr Pro Gly Ala Ser Lys Arg Lys Ser
```

-continued

```
                325                 330                 335
Arg Trp Asp Glu Thr Pro Ala Ser Gln Met Gly Ser Thr Pro Val
                340                 345                 350
Leu Thr Pro Gly Lys Thr Pro Ile Gly Thr Pro Ala Met Asn Met Ala
                355                 360                 365
Thr Pro Thr Pro Gly His Ile Met Ser Met Thr Pro Glu Gln Leu Gln
    370                 375                 380
Ala Trp Arg Trp Glu Arg Glu Ile Asp Glu Arg Asn Arg Pro Leu Ser
385                 390                 395                 400
Asp Glu Glu Leu Asp Ala Met Phe Pro Glu Gly Tyr Lys Val Leu Pro
                405                 410                 415
Pro Pro Ala Gly Tyr Val Pro Ile Arg Thr Pro Ala Arg Lys Leu Thr
                420                 425                 430
Ala Thr Pro Thr Pro Leu Gly Gly Met Thr Gly Phe His Met Gln Thr
                435                 440                 445
Glu Asp Arg Thr Met Lys Ser Val Asn Asp Gln Pro Ser Gly Asn Leu
    450                 455                 460
Pro Phe Leu Lys Pro Asp Asp Ile Gln Tyr Phe Asp Lys Leu Leu Val
465                 470                 475                 480
Asp Val Asp Glu Ser Thr Leu Ser Pro Glu Glu Gln Lys Glu Arg Lys
                485                 490                 495
Ile Met Lys Leu Leu Lys Ile Lys Asn Gly Thr Pro Pro Met Arg
                500                 505                 510
Lys Ala Ala Leu Arg Gln Ile Thr Asp Lys Ala Arg Glu Phe Gly Ala
                515                 520                 525
Gly Pro Leu Phe Asn Gln Ile Leu Pro Leu Leu Met Ser Pro Thr Leu
                530                 535                 540
Glu Asp Gln Glu Arg His Leu Leu Val Lys Val Ile Asp Arg Ile Leu
545                 550                 555                 560
Tyr Lys Leu Asp Asp Leu Val Arg Pro Tyr Val His Lys Ile Leu Val
                565                 570                 575
Val Ile Glu Pro Leu Leu Ile Asp Glu Asp Tyr Tyr Ala Arg Val Glu
                580                 585                 590
Gly Leu Glu Ile Ile Ser Asn Leu Ala Lys Ala Ala Gly Leu Ala Thr
                595                 600                 605
Met Ile Ser Thr Met Arg Pro Asp Ile Asp Asn Met Asp Glu Tyr Val
    610                 615                 620
Arg Asn Thr Thr Ala Arg Ala Phe Ala Val Val Ala Ser Ala Leu Gly
625                 630                 635                 640
Ile Pro Ser Leu Leu Pro Phe Leu Lys Ala Val Cys Lys Ser Lys Lys
                645                 650                 655
Ser Trp Gln Ala Arg His Thr Gly Ile Lys Ile Val Gln Gln Ile Ala
                660                 665                 670
Ile Leu Met Gly Cys Ala Ile Leu Pro His Leu Arg Ser Leu Val Glu
                675                 680                 685
Ile Ile Glu His Gly Leu Val Asp Glu Gln Gln Lys Val Arg Thr Ile
    690                 695                 700
Ser Ala Leu Ala Ile Ala Ala Leu Ala Glu Ala Ala Thr Pro Tyr Gly
705                 710                 715                 720
Ile Glu Ser Phe Asp Ser Val Leu Lys Pro Leu Trp Lys Gly Ile Arg
                725                 730                 735
Gln His Arg Gly Lys Gly Leu Ala Ala Phe Leu Lys Ala Ile Gly Tyr
                740                 745                 750
```

-continued

Leu Ile Pro Leu Met Asp Ala Glu Tyr Ala Asn Tyr Tyr Thr Arg Glu
             755                 760                 765

Val Met Leu Ile Leu Ile Arg Glu Phe Gln Ser Pro Asp Glu Glu Met
770                 775                 780

Lys Lys Ile Val Leu Lys Val Lys Gln Cys Cys Gly Thr Asp Gly
785                 790                 795                 800

Val Glu Ala Asn Tyr Ile Lys Thr Glu Ile Leu Pro Pro Phe Phe Lys
                805                 810                 815

His Phe Trp Gln His Arg Met Ala Ile Leu Asp Arg Arg Asn Tyr Arg
             820                 825                 830

Gln Leu Val Asp Thr Thr Val Glu Leu Ala Ser Asn Lys Val Gly Ala
             835                 840                 845

Ala Glu Ile Ile Ser Arg Ile Val Asp Asp Leu Lys Asp Glu Ala Glu
850                 855                 860

Gln Tyr Arg Lys Met Val Met Glu Thr Ile Glu Lys Ile Met Gly Asn
865                 870                 875                 880

Leu Gly Ala Ala Asp Ile Asp His Lys Leu Glu Glu Gln Leu Ile Asp
                885                 890                 895

Gly Ile Leu Tyr Ala Phe Gln Glu Gln Thr Thr Glu Asp Ser Val Met
             900                 905                 910

Leu Asn Gly Phe Gly Thr Val Val Asn Ala Leu Gly Lys Arg Val Lys
             915                 920                 925

Pro Tyr Leu Pro Gln Ile Cys Gly Thr Val Leu Trp Arg Leu Asn Asn
             930                 935                 940

Lys Ser Ala Lys Val Arg Gln Gln Ala Ala Asp Leu Ile Ser Arg Thr
945                 950                 955                 960

Ala Val Val Met Lys Thr Cys Gln Glu Glu Lys Leu Met Gly His Leu
                965                 970                 975

Gly Val Val Leu Tyr Glu Tyr Leu Gly Glu Glu Tyr Pro Glu Val Leu
                980                 985                 990

Gly Ser Ile Leu Gly Ala Leu Lys Ala Ile Val Asn Val Ile Gly Met
             995                 1000                1005

His Lys Met Thr Pro Pro Ile Lys Asp Leu Leu Pro Arg Leu Thr Pro
     1010                1015                1020

Ile Leu Lys Asn Arg His Glu Lys Val Gln Glu Asn Cys Ile Asp Leu
1025                1030                1035                1040

Val Gly Arg Ile Ala Asp Arg Gly Ala Glu Tyr Val Ser Ala Arg Glu
                1045                1050                1055

Trp Met Arg Ile Cys Phe Glu Leu Leu Glu Leu Leu Lys Ala His Lys
             1060                1065                1070

Lys Ala Ile Arg Arg Ala Thr Val Asn Thr Phe Gly Tyr Ile Ala Lys
     1075                1080                1085

Ala Ile Gly Pro His Asp Val Leu Ala Thr Leu Leu Asn Asn Leu Lys
     1090                1095                1100

Val Gln Glu Arg Gln Asn Arg Val Cys Thr Thr Val Ala Ile Ala Ile
1105                1110                1115                1120

Val Ala Glu Thr Cys Ser Pro Phe Thr Val Leu Pro Ala Leu Met Asn
                1125                1130                1135

Glu Tyr Arg Val Pro Glu Leu Asn Val Gln Asn Gly Val Leu Lys Ser
             1140                1145                1150

Leu Ser Phe Leu Phe Glu Tyr Ile Gly Glu Met Gly Lys Asp Tyr Ile
     1155                1160                1165

-continued

```
Tyr Ala Val Thr Pro Leu Leu Glu Asp Ala Leu Met Asp Arg Asp Leu
        1170            1175            1180

Val His Arg Gln Thr Ala Ser Ala Val Val Gln His Met Ser Leu Gly
1185                1190            1195            1200

Val Tyr Gly Phe Gly Cys Glu Asp Ser Leu Asn His Leu Leu Asn Tyr
                1205            1210            1215

Val Trp Pro Asn Val Phe Glu Thr Ser Pro His Val Ile Gln Ala Val
            1220            1225            1230

Met Gly Ala Leu Glu Gly Leu Arg Val Ala Ile Gly Pro Cys Arg Met
        1235            1240            1245

Leu Gln Tyr Cys Leu Gln Gly Leu Phe His Pro Ala Arg Lys Val Arg
        1250            1255            1260

Asp Val Tyr Trp Lys Ile Tyr Asn Ser Ile Tyr Ile Gly Ser Gln Asp
1265            1270            1275            1280

Ala Leu Ile Ala His Tyr Pro Arg Ile Tyr Asn Asp Asp Lys Asn Thr
                1285            1290            1295

Tyr Ile Arg Tyr Glu Leu Asp Tyr Ile Leu
            1300            1305
```

INTRACELLULAR REGULATORY MOLECULES; RELATED REAGENTS

This application claims priority to a provisional U.S. Patent Application, U.S. Ser. No. 60/032,818, filed Dec. 11, 1996, which is incorporated herein by reference, to a utility U.S. Patent Application.

FIELD OF THE INVENTION

The present invention pertains to compositions related to proteins which function, e.g., in controlling the cell cycle and transcription. In particular, it provides purified genes, proteins, antibodies, and related reagents useful, e.g., to regulate cell division and proliferation of various cell types, including tumor cells.

BACKGROUND OF THE INVENTION

Cancer can occur in any tissue of the body. It results from a change in certain cells that causes them to evade the normal growth limiting mechanisms, i.e., to no longer be under the feedback controls that normally stop cellular growth and reproduction after a given number of such cells have developed. Cell division and transcription are highly coordinated processes that play important roles in this feedback control. See, e.g., Beeson, et al. (eds.) (1979) *Textbook of Medicine*, 15th ed., W. B. Saunders Co., Philadelphia, Pa.; and DeVita, et al. (eds.) (1993) *Cancer: Principles and Practice of Oncology*, 4th ed., Lippincott, Philadelphia, Pa.

Molecules which function to regulate transcription and cell division play important roles in the controlled growth of various types of cells. Aberrations in these controls can lead to various disease states, e.g., oncogenesis, inappropriate immune responses to infections, improper wound healing, developmental abnormalities, and metabolic problems.

The cell cycle can be divided into four phases: the presynthetic phases ($G_0$ and $G_1$); the phase of DNA synthesis (S); and the postsynthetic phase ($G_2$). See, e.g., Guyton (ed.) (1976) *Textbook of Medical Physiology*, 5th ed., W.B. Saunders Co., Philadelphia, Pa.; Alberts, et al. (eds.) (1994) *Molecular Biology of the Cell*, 3rd ed., Garland Publishing, New York, N.Y.; and Darnell, et al. (eds.) (1990) *Molecular Cell Biology*, 2nd ed., W. H. Freeman, New York, N.Y. Effective chemot herapeutic agents are often those which target diseased cells in the S phase, e.g., choriocarcinoma, acute lymphocytic leukemia, lyphocytic lymphosarcoma, Burkitt's lymphoma, Hodgkin's disease, testicular neoplasms, Wilm's tumor, and Ewing's sarcoma. Unfortunately, oncogenic cells not actively dividing are less sensitive to these agents.

In the immune system, many of the effects of known cytokines on gene transcription are known to be mediated by cytokine inducible DNA binding proteins. See, e.g., Paul (ed.) (1994) *Fundamental Immunology*, 3rd ed., Raven Press, New York, N.Y. In particular, the family of Interferon Regulatory Factors (IFN), which are present in the promoters of interferon (IFN) genes, includes both activators and repressors of transcription. IFN mediated gene regulation is a complex cascade of events that leads, e.g., to acquisition of an antiviral state.

The lack of knowledge regarding the control of the cell cycle or transcriptional elements has hampered the ability of medical science to specifically regulate cell division or immune responses. The present invention provides compositions which will be important in the control of cell division and transcription.

SUMMARY OF THE INVENTION

The present invention is based in part upon the discovery of intracellular regulatory molecules which are hereby designated p150, p130, VCP, tsg101, and KWC02. p150, p130, and VCP are Cyclin E-Cdk associated proteins. Tsg101 and KWC02 are transcription factors.

The present invention provides substantially pure or recombinant p150, p130, VCP, tsg101, or KWC02 antigenic or peptide fragments. The peptide may be a full length natural protein or peptide from a human; comprise at least one polypeptide segment of SEQ ID NO: 2, 4, 6, 8, or 10; or exhibit a post-translational modification pattern distinct from a natural p150, p130, VCP, tsg101, or KWC02 protein. Also encompassed is a fusion protein and peptidomimetic. Various compositions of matter are further provided, e.g., selected from: a substantially pure or recombinant p150 protein or peptide exhibiting at least about 85% sequence identity over a length of at least about 12 amino acids to SEQ ID NO: 2; a natural sequence p150 of SEQ ID NO: 2; a fusion protein comprising p150 sequence; a substantially pure or recombinant p130 protein or peptide exhibiting at least about 85% sequence identity over a length of at least about 12 amino acids to SEQ ID NO: 4; a natural sequence p130 of SEQ ID NO: 4; a fusion protein comprising p130 sequence; a substantially pure or recombinant VCP protein or peptide exhibiting at least about 85% sequence identity over a length of at least about 12 amino acids to SEQ ID NO: 6; a natural sequence VCP of SEQ ID NO: 6; a fusion protein comprising VCP sequence; a substantially pure or recombinant tsg101 protein or peptide exhibiting at least about 85% sequence identity over a length of at least about 12 amino acids to SEQ ID NO: 8; a natural sequence tsg101 of SEQ ID NO: 8; a fusion protein comprising tsg101 sequence; a substantially pure or recombinant KWC02 protein or peptide exhibiting at least about 85% sequence identity over a length of at least about 12 amino acids to SEQ ID NO: 10; a natural sequence KWC02 of SEQ ID NO: 10; or a fusion protein comprising KWC02 sequence. In other preferred embodiments, the substantially pure or isolated protein comprises a segment exhibiting sequence identity to a corresponding portion of: a p150, wherein: said homology is at least about 90% identity and said portion is at least about 9 amino acids; said homology is at least about 80% identity and said portion is at least about 17 amino acids; or said homology is at least about 70% identity and said portion is at least about 25 amino acids; a p130, wherein: said homology is at least about 90% identity and said portion is at least about 9 amino acids; said homology is at least about 80% identity and said portion is at least about 17 amino acids; or said homology is at least about 70% identity and said portion is at least about 25 amino acids; a VCP, wherein: said homology is at least about 90% identity and said portion is at least about 9 amino acids; said homology is at least about 80% identity and said portion is at least about 17 amino acids; or said homology is at least about 70% identity and said portion is at least about 25 amino acids; a tsg101, wherein: said homology is at least about 90% identity and said portion is at least about 9 amino acids; said homology is at least about 80% identity and said portion is at least about 17 amino acids; or said homology is at least about 70% identity and said portion is at least about 25 amino acids; or a KWC02, wherein: said homology is at least about 90% identity and said portion is at least about 9 amino acids; said homology is at least about 80% identity and said portion is at least about 17 amino acids; or said homology is at least about 70% identity and said portion is at least about 25 amino acids. In other embodiments, the: p150: comprises a mature sequence of Table 1; or protein or peptide: is from a warm blooded animal selected from a mammal, including a primate; comprises at least one polypeptide segment of SEQ ID NO: 2; exhibits a plurality of portions exhibiting said identity; is a natural allelic variant of p150; has a length at least about 30 amino acids; exhibits at least two non-overlapping epitopes which are specific for a mammalian p150; exhibits a sequence identity at least about 90% over a length of at least about 20 amino acids to a primate p150; exhibits at least two non-overlapping epitopes which are specific for a primate p150; exhibits a sequence identity at least about 90% over a length of at least about 20 amino acids to a primate p150; is glycosylated; is a synthetic polypeptide; is attached to a solid substrate; is conjugated to another chemical moiety; is a 5-fold or less substitution from natural sequence; or is a deletion or insertion variant from a natural sequence; p130: comprises a mature sequence of Table 2; or protein or peptide: is from a warm blooded animal selected from a mammal$_1$, including a primate; ii) comprises at least one polypeptide segment of SEQ ID NO: 4; exhibits a plurality of portions exhibiting said identity; is a natural allelic variant of p130; has a length at least about 30 amino acids; exhibits at least two non-overlapping epitopes which are specific for a mammalian p130; exhibits a sequence identity at least about 90% over a length of at least about 20 amino acids to a primate p130; exhibits at least two non-overlapping epitopes which are specific for a primate p130; exhibits a sequence identity at least about 90% over a length of at least about 20 amino acids to a primate p130; is glycosylated; is a synthetic polypeptide; is attached to a solid substrate; is conjugated to another chemical moiety; is a 5-fold or less substitution from natural sequence; or is a deletion or insertion variant from a natural sequence; VCP: comprises a mature sequence of Table 3; or protein or peptide: is from a warm blooded animal selected from a mammal, including a primate; comprises at least one polypeptide segment of SEQ ID NO: 6; exhibits a plurality of portions exhibiting said identity; is a natural allelic variant of VCP; has a length at least about 30 amino acids; exhibits at least two non-overlapping epitopes which are specific for a mammalian VCP; exhibits a sequence identity at least about 90% over a length of at least about 20 amino acids to a primate VCP; exhibits at least two non-overlapping epitopes which are specific for a primate VCP; exhibits a sequence identity at least about 90% over a length of at least about 20 amino acids to a primate VCP; is glycosylated; is a synthetic polypeptide; is attached to a solid substrate; is conjugated to another chemical moiety; is a 5-fold or less substitution from natural sequence; or is a deletion or insertion variant from a natural sequence; tsg101: comprises a mature sequence of Table 4; or protein or peptide: is from a warm blooded animal selected from a mammal, including a primate; comprises at least one polypeptide segment of SEQ ID NO: 8; exhibits a plurality of portions exhibiting said identity; is a natural allelic variant of tsg101; has a length at least about 30 amino acids; exhibits at least two non-overlapping epitopes which are specific for a mammalian tsg101; exhibits a sequence identity at least about 90% over a length of at least about 20 amino acids to a primate tsg101; exhibits at least two non-overlapping epitopes which are specific for a primate tsg101; exhibits a sequence identity at least about 90% over a length of at least about 20 amino acids to a primate tsg101; is glycosylated; is a synthetic polypeptide; is attached to a solid substrate; is conjugated to another chemical moiety; is a 5-fold or less substitution from natural sequence; or is a deletion or insertion variant from a natural sequence; or KWC02: comprises a mature sequence of Table 5; or protein or peptide: is from a warm blooded animal selected from a mammal, including a primate; comprises at least one polypeptide segment of SEQ ID NO: 10; exhibits a plurality of portions exhibiting said identity; is a natural allelic variant of KWC02; has a length at least about 30 amino acids; exhibits at least two non-overlapping epitopes which are specific for a mammalian KWC02; exhibits a sequence identity at least about 90% over a length of at least about 20 amino acids to a primate KWC02; exhibits at least two non-overlapping epitopes which are specific for a primate KWC02; exhibits a sequence identity at least about 90% over a length of at least about 20 amino acids to a primate KWC02; is glycosylated; is a synthetic polypeptide; is attached to a solid substrate; is conjugated to another chemical moiety; is a 5-fold or less substitution from natural sequence; or is a deletion or insertion variant from a natural sequence. Other preferred compositions include those which comprise: a sterile p150 protein or peptide; said p150 protein or peptide and a carrier, wherein said carrier is: an aqueous compound, including water, saline, and/or buffer; and/or formulated for oral, rectal, nasal, topical, or parenteral administration; a sterile p130 protein or peptide; said p130 protein or peptide and a carrier, wherein said carrier is: an aqueous compound, including water, saline, and/or buffer; and/or formulated for oral, rectal, nasal, topical, or parenteral administration; a sterile VCP protein or peptide; said VCP protein or peptide and a carrier, wherein said carrier is: an aqueous compound, including water, saline, and/or buffer; and/or formulated for oral, rectal, nasal, topical, or parenteral administration; a sterile tsg101 protein or peptide; said tsg101 protein or peptide and a carrier, wherein said carrier is: an aqueous compound, including water, saline, and/or buffer; and/or formulated for oral, rectal, nasal, topical, or parenteral administration; a sterile KWC02 protein or peptide; or said KWC02 protein or peptide and a carrier, wherein said carrier is: an aqueous compound, including water, saline, and/or buffer; and/or formulated for oral, rectal, nasal, topical, or parenteral administration. Certain fusion proteins are provided, e.g., comprising: mature protein comprising sequence of Table 1; mature protein comprising sequence of Table 2; mature protein comprising sequence of Table 3; mature protein comprising sequence of Table 4; mature protein comprising sequence of Table 5; a detection or purification tag, including a FLAG, His6, or Ig sequence; or sequence of another intracellular protein. Various kits are also provided, e.g., comprising such a protein or polypeptide, and: a compartment comprising said protein or polypeptide; and/or instructions for use or disposal of reagents in said kit.

The invention further provides an antibody which specifically binds a p150, p130, VCP, tsg101, or KWC02 protein or polypeptide. The p150, p130, VCP, tsg101, or KWC02 protein may be from a human; the antibody is raised against a purified peptide sequence of SEQ ID NO: 2, 4, 6, 8, or 10; the antibody is a monoclonal antibody; or the antibody is labeled. Further embodiments include a binding compound comprising an antigen binding portion from an antibody, which specifically binds to a natural: p150 protein, wherein: said protein is a primate protein; said binding compound is an Fv, Fab, or Fab2 fragment; said binding compound is conjugated to another chemical moiety; or said antibody: is raised against a peptide sequence of a mature polypeptide comprising sequence of Table 1; is raised against a mature p150; is raised to a purified p150; is immunoselected; is a polyclonal antibody; binds to a denatured p150; exhibits a Kd to antigen of at least 30 $\mu$M; is attached to a solid substrate, including a bead or plastic membrane; is in a sterile composition; or is detectably labeled, including a radioactive or fluorescent label; p130 protein, wherein: said protein is a primate protein; said binding compound is an Fv, Fab, or Fab2 fragment; said binding compound is conjugated to another chemical moiety; or said antibody: is raised against a peptide sequence of a mature polypeptide comprising sequence of Table 2; is raised against a mature p130; is raised to a purified p130; is immunoselected; is a polyclonal antibody; binds to a denatured p130; exhibits a Kd to antigen of at least 30 μM; is attached to a solid substrate, including a bead or plastic membrane; is in a sterile composition; or is detectably labeled, including a radioactive or fluorescent label; VCP protein, wherein: said protein is a primate protein; said binding compound is an Fv, Fab, or Fab2 fragment; said binding compound is conjugated to another chemical moiety; or said antibody: is raised against a peptide sequence of a mature polypeptide comprising sequence of Table 3; is raised against a mature VCP; is raised to a purified VCP; is immunoselected; is a polyclonal antibody; binds to a denatured VCP; exhibits a Kd to antigen of at least 30 μM; is attached to a solid substrate, including a bead or plastic membrane; is in a sterile composition; or is detectably labeled, including a radioactive or fluorescent label; tsg101 protein, wherein: said protein is a primate protein; said binding compound is an Fv, Fab, or Fab2 fragment; said binding compound is conjugated to another chemical moiety; or said antibody: is raised against a peptide sequence of a mature polypeptide comprising sequence of Table 4; is raised against a mature tsg101; is raised to a purified tsg101; is immunoselected; is a polyclonal antibody; binds to a denatured tsg101; exhibits a Kd to antigen of at least 30 μM; is attached to a solid substrate, including a bead or plastic membrane; is in a sterile composition; or is detectably labeled, including a radioactive or fluorescent label; KWC02 protein, wherein: said protein is a primate protein; said binding compound is an Fv, Fab, or Fab2 fragment; said binding compound is conjugated to another chemical moiety; or said antibody: is raised against a peptide sequence of a mature polypeptide comprising sequence of Table 5; is raised against a mature KWC02;is raised to a purified KWC02; is immunoselected; is a polyclonal antibody; binds to a denatured KWC02; exhibits a Kd to antigen of at least 30 μM; is attached to a solid substrate, including a bead or plastic membrane; is in a sterile composition; or is detectably labeled, including a radioactive or fluorescent label. In other embodiments, the composition may: comprise a sterile binding compound, or said binding compound and a carrier, wherein said carrier is: an aqueous compound, including water, saline, and/or buffer; and/or formulated for oral, rectal, nasal, topical, or parenteral administration. The invention also provides kits, e.g., comprising said binding compound, and: a compartment comprising said binding compound; and/or instructions for use or disposal of reagents in said kit.

Also provided is a method of purifying: a p150 protein or peptide from other materials in a mixture comprising contacting said mixture to an antibody, and separating bound p150 from other materials; a p130 protein or peptide from other materials in a mixture comprising contacting said mixture to an antibody, and separating bound p130 from other materials; a VCP protein or peptide from other materials in a mixture comprising contacting said mixture to an antibody, and separating bound VCP from other materials; a tsg101 protein or peptide from other materials in a mixture comprising contacting said mixture to an antibody, and separating bound tsg101 from other materials; or a KWC02 protein or peptide from other materials in a mixture comprising contacting said mixture to an antibody, and separating bound KWC02 from other materials.

The present invention encompasses an isolated or recombinant expression vector capable of encoding a p150, p130, VCP, tsg101, or KWC02 protein or polypeptide. The vector may encode a sequence of SEQ ID NO: 2, 4, 6, 8, or 10; or comprise a protein coding sequence of SEQ ID NO: 1, 3, 5, 7, or 9. Preferred nucleic acids include, e.g., an isolated or recombinant nucleic acid encoding a: p150 protein or peptide or fusion protein, wherein: said protein is from a mammal, including a primate; or said nucleic acid: encodes an antigenic peptide sequence of Table 1; encodes a plurality of antigenic peptide sequences of Table 1; exhibits at least about 80% identity to a natural cDNA encoding said segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding said p150 protein; or is a PCR primer, PCR product, or mutagenesis primer; p130 protein or peptide or fusion protein, wherein: said protein is from a mammal, including a primate; or said nucleic acid: encodes an antigenic peptide sequence of Table 2; encodes a plurality of antigenic peptide sequences of Table 2; exhibits at least about 80% identity to a natural cDNA encoding said segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding said p130 protein; or is a PCR primer, PCR product, or mutagenesis primer; VCP protein or peptide or fusion protein, wherein: said protein is from a mammal, including a primate; or said nucleic acid: encodes an antigenic peptide sequence of Table 3; encodes a plurality of antigenic peptide sequences of Table 3; exhibits at least about 80% identity to a natural cDNA encoding said segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding said VCP protein; or is a PCR primer, PCR product, or mutagenesis primer; tsg101 protein or peptide or fusion protein, wherein: said protein is from a mammal, including a primate; or said nucleic acid: encodes an antigenic peptide sequence of Table 4; encodes a plurality of antigenic peptide sequences of Table 4; exhibits at least about 80% identity to a natural cDNA encoding said segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding said tsg101 protein; or is a PCR primer, PCR product, or mutagenesis primer; or KWC02 protein or peptide or fusion protein, wherein: said protein is from a mammal, including a primate; or said nucleic acid: encodes an antigenic peptide sequence of Table 5; encodes a plurality of antigenic peptide sequences of Table 5; exhibits at least about 80% identity to a natural cDNA encoding said segment; is an expression vector; further comprises an origin of replication; is from a natural source; comprises a detectable label; comprises synthetic nucleotide sequence; is less than 6 kb, preferably less than 3 kb; is from a mammal, including a primate; comprises a natural full length coding sequence; is a hybridization probe for a gene encoding said KWC02 protein; or is a PCR primer, PCR product, or mutagenesis primer. A cell or tissue comprising such a recombinant nucleic acid is provided, e.g., wherein said cell is: a prokaryotic cell; a eukaryotic cell; a bacterial cell; a yeast cell; an insect cell; a mammalian cell; a mouse cell; a primate cell; or a human cell.

Preferred kits include those comprising, e.g., said nucleic acid, and: a compartment comprising said nucleic acid; a compartment further comprising said intracellular protein or polypeptide; and/or instructions for use or disposal of reagents in said kit. Typically, the kit is capable of making a qualitative or quantitative analysis.

Various methods of making a p150, p130, VCP, tsg101, and KWC02 protein or peptide by expressing such a vector are also provided. In various embodiments, a cell, tissue, or organ will comprise such a vector.

A kit for detecting is provided comprising: a substantially pure p150, p130, VCP, tsg101, or KWC02 protein or fragment; an antibody or binding partner which specifically binds a p150, p130, VCP, tsg101, or KWC02 protein; or a nucleic acid encoding a p150, p130, VCP, tsg101, or KWC02 protein or polypeptide. A method for detecting in a sample the presence of a p150, p130, VCP, tsg101, or KWC02 nucleic acid, protein, or antibody is provided, the method comprising testing said sample with this kit is also encompassed.

The present invention also embraces a method of modulating the physiology of a cell comprising contacting the cell with a substantially pure p101, p130, VCP, tsg101, or KWC02 protein or fragment; an antibody or binding partner which specifically binds a p150, p130, VCP, tsg101, or KWC02; a nucleic acid encoding a p150, p130, VCP, tsg101, or KWC02 protein or peptide; a small molecule which inhibits the binding of p150, p130, VCP, tsg101, or KWC02 to its binding partner; or a small molecule which inhibits the activity of p150, p130, VCP, tsg101, or KWC02. This method further encompasses where the cell is a cancer cell and/or the modulating is blocking cell cycle progression. The cell may be in a tissue.

Alternatively, the invention provides methods of modulating physiology or development of a cell comprising introducing into said cell with an effective amount of: an antibody or binding partner which binds specifically to a p150; a substantially pure p150 protein, or peptide thereof; or a nucleic acid encoding a p150 peptide, or a complementary nucleic acid; an antibody or binding partner which binds specifically to a p130; a substantially pure p130 protein, or peptide thereof; a nucleic acid encoding a p130 peptide, or a complementary nucleic acid; an antibody or binding partner which binds specifically to a VCP; a substantially pure VCP protein, or peptide thereof; a nucleic acid encoding a VCP peptide, or a complementary nucleic acid; an antibody or binding partner which binds specifically to a tsg101; a substantially pure tsg101 protein, or peptide thereof; a nucleic acid encoding a tsg101 peptide, or a complementary nucleic acid; an antibody or binding partner which binds specifically to a KWC02; a substantially pure KWC02 protein, or peptide thereof; or a nucleic acid encoding a KWC02 peptide, or a complementary nucleic acid. In preferred methods, the cell is a cancer cell and said modulating of physiology is the blocking of cell cycle progression.

Also encompassed is a recombinant nucleic acid encoding a polypeptide comprising at least about 70% identity over a stretch of at lease 20 amino acids to a p130 of SEQ ID NO: 2 or a KWC02 of SEQ ID NO: 10. In another embodiment a recombinant nucleic acid is provided which encodes a polypeptide comprising at least 96% identity over a stretch of 100 amino acids to a p150, VCP, or tsg101, preferably of SEQ ID NO: 2, 6, or 8, respectively. Other preferred nucleic acids include, e.g., ones which: hybridize under wash conditions of 30° C. and less than 2M salt to SEQ ID NO: 1; exhibit at least about 85% identity over a stretch of at least about 30 nucleotides to a primate p150; hybridize under wash conditions of 30° C. and less than 2M salt to SEQ ID NO: 3; exhibit at least about 85% identity over a stretch of at least about 30 nucleotides to a primate p130; hybridize under wash conditions of 30° C. and less than 2M salt to SEQ ID NO: 5; exhibit at least about 85% identity over a stretch of at least about 30 nucleotides to a primate VCP; hybridize under wash conditions of 30° C. and less than 2M salt to SEQ ID NO: 7; exhibit at least about 85% identity over a stretch of at least about 30 nucleotides to a primate tsg101; hybridize under wash conditions of 30° C. and less than 2M salt to SEQ ID NO: 9; or exhibit at least about 85% identity over a stretch of at least about 30 nucleotides to a primate KWC02. In other forms, the nucleic acid will be those wherein: said wash conditions are: at 45° C. and/or 500 mM salt, or at 55° C. and/or 150 mM salt; or said identity is: at least 90% and/or said stretch is at least 55 nucleotides; or at least 95% and/or said stretch is at least 75 nucleotides.

The present invention also embraces a method for screening for an antagonist of p150, p130, VCP, tsg101, or KWC02 comprising contacting a cell with said antagonist and measuring cell proliferation.

DETAILED DESCRIPTION OF THE PREFERRED EMBODIMENTS

OUTLINE

I. General
II. Definitions
III. Nucleic Acids
   A. natural isolates; methods
   B. synthetic genes
   C. methods to isolate
IV. Purified p130, p150, VCP, tsg101, or KWC02
   A. physical properties
   B. biological properties
V. Antibodies
   A. polyclonal
   B. monoclonal
   C. fragments, binding compositions
VI. Making p130, p150, VCP, tsg101, or KWC02; Mimetics
   A. recombinant methods
   B. synthetic methods
   C. natural purification
VII. Physical Variants
   A. sequence variants, fragments
   B. post-translational variants
VIII. Functional Variants
   A. analogs; fragments
   B. mimetics
   C. species variants
IX. Binding Agent:p130, p150, tsg101, or KWC02 complexes X. Uses
  A. diagnostic
  B. therapeutic
XI. Kits I. General Cyclins and their partner catalytic subunits, the cyclin-dependent kinases (Cdks), play key roles in the regulation of eukaryotic cell cycle events. See, e.g., Draetta (1994) *Curr. Opin. Cell Biol.* 6:842–846; Sherr (1994) *Cell* 79:551–555; and Ohtsubo, et al. (1995) *Mol. Cell. Biol.* 15:2612–2624. Cyclins were first identified in marine invertebrates on the basis of their dramatic cell cycle periodic expression during meiotic and mitotic divisions.

A large family of cyclins, designated cyclins A-H, bind and activate different Cdks which are serine/threonine kinases essential for cell cycle progression. The timing of the expression of the various cyclins is key in determining at which phase of the cell cycle (S, $G_0$, $G_1$, or $G_2$) their associated Cdk is active. D-type cyclins are synthesized early in $G_1$ and bind and activate CDK4 and CDK6. Cyclin E-Cdk2 and Cyclin A-Cdk2 complexes form later in $G_1$ as cells prepare to begin DNA synthesis. Cyclin B-cdc2 is active during $G_2$ and mitosis. See, e.g., Lees (1995) *Curr. Opin. Cell Biol.* 7:773–780.

Other Cyclin-Cdk complex associated proteins are critical for modulation of cyclin activity. Three such novel human proteins are p150, p130 and VCP. These proteins were isolated by the immunoprecipitation of myeloid leukemia (ML) cell proteins using monoclonal antibodies specific for human cyclin E. Proteins that co-immunoprecipitated with cyclin E were visualized by SDS-PAGE. P150, p130, and VCP were purified in large quantities by Cyclin E affinity chromatography and subsequently sequenced, see, e.g., P. Matsudaira (ed.) (1993) *A Practical Guide to Protein and Peptide Purification for Microsequencing*, Academic Press, San Diego, Calif.

Peptide sequences from p150 were used to design degenerate primers in order to screen an activated (LPS, IFNγ) human monocyte (U937, K. Bacon and T. McClanahan, DNAX, Palo Alto, Calif.) cDNA library. A 4.4 kb clone was isolated and sequenced. See, e.g., Table 1 or SEQ ID NO: 1 and 2. p150 has striking amino acid sequence identity (95%) to a recently identified human protein belonging to the SWI/SNF complex which was originally described in yeast. See, e.g., Wang, et al. (1996) *Genes & Devel.* 10:2177–2130; and Peterson, et al. (1992) *Cell* 68:573–583. The yeast protein is apparently involved in chromatin remodeling, and binds to cyclin E and to BRG and BRM, which are the human homologs of SWI2. The p150 is phosphorylated by the cyclin E/cdk2 complex. Overexpression of p150 is toxic to cells.

Peptide sequence from p130 was screened against available public data bases, e.g., Merck-WashU public database and GenBank. Expressed Sequence Tags (ESTs) encoding a 16 amino acid peptide were identified (gb|dbest|T79440, gb|dbest|R89324, gb|dbest|N90895, gb|dbest|N25983, and gb|dbest|R96476) and used to isolate a longer 642 bp cDNA clone from the U937 activated monocyte library. See Table 2 and SEQ ID NO: 3 and 4. This protein exhibits significant identity to a SAP155, a splicesomal associated protein involved in the catalytic step of mRNA splicing. This protein associates with other SAPs, e.g., SAP155 and SAP145. It is also a potential substrate for the cyclin E complex. Immunofluorescence localization suggests a nuclear localization, e.g., localized to nuclear speckles.

Peptide microsequencing of the third protein revealed this to be a Valosin Containing Protein (VCP), the human homolog to porcine VCP and the *S. cerevisiae* cell cycle protein, CDC48. See, Koller, et al. (1987) *Nature* 325:542–545; and Frohlich, et al. (1991) *J. Cell Biol.* 114:443–453. The public database was carefully searched and a partial clone was used to screen the activated U937 monocyte library. A 3.0 kb clone was isolated. See, Table 3 and SEQ ID NO: 5 and 6. This clone encodes an 807 amino acid protein having 99% identity to mouse VCP. Previous data indicates that mouse VCP is phosphorylated immediately upon activation of T and B cells. See, e.g., Egerton, et al. (1992) *EMBO J.* 11:3533–3540; and Schulte, et al. (1994) *J. Immunol.* 153:5465–72.

Cdks can also exert control on cell division and proliferation by phosphorylating specific intracellular target proteins. This phosphorylation event can induce the cellular transition from the $G_1$ to the S phase of the cell cycle. See, e.g., Strahler, et al. (1992) *Biochem. Biophys. Res. Comm.* 185:197–203; Brattsand, et al. (1994) *Eur. J. Biochem.* 220:359–368; and Li, et al. (1996) *Cell* 85:319–329.

Two other genes apparently encoding other intracellular proteins have been isolated. Tsg101 was isolated using low-stringency PCR on a peripheral blood monocyte cDNA library. This gene appears to be the human homolog of previously identified mouse tsg101. See, e.g., Li, et al. (1996) *Cell* 85:319–329. A 1.5 kb clone was isolated which encodes a 391 amino acid protein. See Table 4 and SEQ ID NO: 7 and 8. The mouse and human proteins share about 93% identity. A domain of this protein has been reported to interact with stathmin, a putative in vivo target of cdk2 containing cyclin/cdk complexes. See, e.g., Maucuer, et al. (1996) *Proc. Natl. Acad. Sci.* 92:3100–3104. Tsg101 may constitute a link between the phosphorylation of stathmin and cell cycle progression. Mouse tsg101 knockouts in NIH3T3 fibroblasts lead to growth in soft agar. Based on protein pattern and motif searches, tsg101 is suggested to act as a transcription factor with the overall structure being analogous to nuclear oncoproteins such as fos and jun. See, Li, et al. (1996) *Cell* 85:319–329.

Transcription factors also play a role in cellular growth, differentiation, proliferation, etc. These factors are generally DNA binding proteins that bind gene promoters at specific consensus sequences. One such family of binding proteins are Interferon Response Factors (IRF). Promoters of genes responsive to IFNα, IFNβ, and IFNγ have Interferon Consensus Sequences (ICS) or IFNγ activation sequences to which the IRFs bind and lead to a response to IFNs. See, e.g., Weisz, et al (1992) *J. Biol. Chem.* 267:25589–25596; Grant, et al. (1995) *Nucl. Acids. Res.* 23:2137–2146; and Au, et al. (1995) *Proc. Natl. Acad. Sci.* 92:11657–11661. KWC02, a homolog of the IRFs, was isolated from a subtraction of cDNA from a resting human monocyte cell line (U937) from elutriated human monocytes stimulated with LPS, IFNγ, and IL-10.

Two full length clones of 1.9 kb and 1.7 kb were identified and have significant identity to other known IRFs. The sequence of the 1.9 kb clone is shown in Table 5 and SEQ ID NO: 9 and 10. In particular, KWC02 possesses the conserved Interferon Consensus Sequence Binding Protein (ICSBP) motif of other known IRFs. Preliminary distribution data reveals expression at high levels in activated monocytes. KWC02 is also present in resting T cells, but is down regulated upon activation. NK cells also express KWC02. Low level expression is also evident in spleen tissue.

TABLE 1

Human p150 nucleic acid and predicted amino acid sequence. SEQ ID NO: 1 and 2. The SWI3 conserved domain runs from about Asp440 through Pro563. The MYB-like domain runs from about Thr610 through Glu720. The coiled-coiled region runs from about Glu860 through Gln940.

```
GGAATTCCCG GGTCGACCCA CGCGTCCGCT ACGCGCGCGG GGGTGCGCGC GGGAACGACC   60

GGGAAACACC GCGAGGGCCG GGGTGGGCCA GGCTGTGGGG ACGACGGGCT GCGACG      116

ATG GCC GCA GCG GCG GGC GGC GGC GGG CCG GGG ACA GCG GTA GGC GCC   164
Met Ala Ala Ala Ala Gly Gly Gly Gly Pro Gly Thr Ala Val Gly Ala
 1           5                   10                  15

ACG GGC TCG GGG ATT GCG GCG GCA GCC GCA GGC CTA GCT GTT TAT CGA   212
Thr Gly Ser Gly Ile Ala Ala Ala Ala Ala Gly Leu Ala Val Tyr Arg
             20                  25                  30

CGG AAG GAT GGG GGC CCG GCC ACC AAG TTT TGG GAG AGC CCG GAG ACG   260
Arg Lys Asp Gly Gly Pro Ala Thr Lys Phe Trp Glu Ser Pro Glu Thr
         35                  40                  45

GTG TCC CAG CTG GAT TCG GTG CGG GTC TGG CTG GGC AAG CAC TAC AAG   308
Val Ser Gln Leu Asp Ser Val Arg Val Trp Leu Gly Lys His Tyr Lys
     50                  55                  60

AAG TAT GTT CAT GCG GAT GCT CCT ACC AAT AAA ACA CTG GCT GGG CTG   356
Lys Tyr Val His Ala Asp Ala Pro Thr Asn Lys Thr Leu Ala Gly Leu
 65                  70                  75                  80

GTG GTG CAG CTT CTT CAG TTC CAG GAA GAT GCC TTT GGG AAG CAT GTC   404
Val Val Gln Leu Leu Gln Phe Gln Glu Asp Ala Phe Gly Lys His Val
                 85                  90                  95

ACC AAC CCG GCC TTC ACC AAA CTC CCT GCA AAG TGT TTC ATG GAT TTC   452
Thr Asn Pro Ala Phe Thr Lys Leu Pro Ala Lys Cys Phe Met Asp Phe
             100                 105                 110

AAA GCT GGA GGC GCC TTA TGT CAC ATT CTT GGG GCT GCT TAC AAG TAT   500
Lys Ala Gly Gly Ala Leu Cys His Ile Leu Gly Ala Ala Tyr Lys Tyr
         115                 120                 125

AAA AAT GAA CAG GGA TGG CGG AGG TTT GAC CTA CAG AAC CCA TCT CGA   548
Lys Asn Glu Gln Gly Trp Arg Arg Phe Asp Leu Gln Asn Pro Ser Arg
     130                 135                 140

ATG GAT CGT AAT GTG GAA ATG TTT ATG AAC ATT GAA AAA ACA TTG GTG   596
Met Asp Arg Asn Val Glu Met Phe Met Asn Ile Glu Lys Thr Leu Val
145                 150                 155                 160

CAG AAC AAT TGT TTG ACC AGA CCC AAC ATC TAC CTC ATT CCA GAC ATT   644
Gln Asn Asn Cys Leu Thr Arg Pro Asn Ile Tyr Leu Ile Pro Asp Ile
                 165                 170                 175

GAT CTG AAG TTG GCT AAC AAA TTG AAA GAT ATC ATC AAA CGA CAT CAG   692
Asp Leu Lys Leu Ala Asn Lys Leu Lys Asp Ile Ile Lys Arg His Gln
             180                 185                 190

GGA ACA TTT ACG GAT GAG AAG TCA AAA GCT TCC CAC CAC ATT TAC CCA   740
Gly Thr Phe Thr Asp Glu Lys Ser Lys Ala Ser His His Ile Tyr Pro
         195                 200                 205

TAT TCT TCC TCA CAA GAC GAT GAA GAA TGG TTG AGA CCG GTG ATG AGA   788
Tyr Ser Ser Ser Gln Asp Asp Glu Glu Trp Leu Arg Pro Val Met Arg
     210                 215                 220

AAA GAG AAG CAA GTG TTA GTG CAT TGG GGC TTT TAC CCA GAC AGC TAT   836
Lys Glu Lys Gln Val Leu Val His Trp Gly Phe Tyr Pro Asp Ser Tyr
225                 230                 235                 240

GAT ACT TGG GTC CAT AGT AAT GAT GTT GAT GCT GAA ATT GAA GAT CCA   884
Asp Thr Trp Val His Ser Asn Asp Val Asp Ala Glu Ile Glu Asp Pro
                 245                 250                 255

CCA ATT CCA GAA AAA CCA TGG AAG GTT CAT GTG AAA TGG ATT TTG GAC   932
Pro Ile Pro Glu Lys Pro Trp Lys Val His Val Lys Trp Ile Leu Asp
             260                 265                 270

ACT GAT ATT TTC AAT GAA TGG ATG AAT GAG GAG GAT TAT GAG GTG GAT   980
```

TABLE 1-continued

Human p150 nucleic acid and predicted amino acid sequence.
SEQ ID NO: 1 and 2. The SWI3 conserved domain runs from about
Asp440 through Pro563. The MYB-like domain runs from about Thr610
through Glu720. The coiled-coiled region runs from about Glu860
through Gln940.

```
            Thr Asp Ile Phe Asn Glu Trp Met Asn Glu Glu Asp Tyr Glu Val Asp
                    275             280             285

GAA AAT AGG AAG CCT GTG AGT TTT CGT CAG CGG ATT TCA ACC AAG AAT    1028
Glu Asn Arg Lys Pro Val Ser Phe Arg Gln Arg Ile Ser Thr Lys Asn
        290             295             300

GAA GAG CCA GTC AGA AGT CCA GAA AGA AGA GAT AGA AAA GCA TCA GCT    1076
Glu Glu Pro Val Arg Ser Pro Glu Arg Arg Asp Arg Lys Ala Ser Ala
305             310             315             320

AAT GCT CGA AAG AGG AAA CAT TCG CCT TCG CCT CCC CCT CCG ACA CCA    1124
Asn Ala Arg Lys Arg Lys His Ser Pro Ser Pro Pro Pro Pro Thr Pro
                325             330             335

ACA GAA TCA CGG AAG AAG AGT GGG AAG AAA GGC CAA GCT AGC CTT TAT    1172
Thr Glu Ser Arg Lys Lys Ser Gly Lys Lys Gly Gln Ala Ser Leu Tyr
            340             345             350

GGG AAG CGC AGA AGT CAG AAA GAG GAA GAT GAG CAA GAA GAT CTA ACC    1220
Gly Lys Arg Arg Ser Gln Lys Glu Glu Asp Glu Gln Glu Asp Leu Thr
                355             360             365

AAG GAT ATG GAA GAC CCA ACA CCT GTA CCC AAT ATA GAA GAA GTA GTA    1268
Lys Asp Met Glu Asp Pro Thr Pro Val Pro Asn Ile Glu Glu Val Val
    370             375             380

CTT CCC AAA AAT GTG AAC CTA AAG AAA GAT AGT GAA AAT ACA CCT GTT    1316
Leu Pro Lys Asn Val Asn Leu Lys Lys Asp Ser Glu Asn Thr Pro Val
385             390             395             400

AAA GGA GGA ACT GTA GCG GAT CTA GAT GAG CAG GAT GAA GAA ACA GTC    1364
Lys Gly Gly Thr Val Ala Asp Leu Asp Glu Gln Asp Glu Glu Thr Val
                405             410             415

ACA GCA GGA GGA AAG GAA GAT GAA GAT CCT GCC AAA GGT GAT CAG AGT    1412
Thr Ala Gly Gly Lys Glu Asp Glu Asp Pro Ala Lys Gly Asp Gln Ser
            420             425             430

CGA TCA GTT GAC CTT GGG GAA GAT AAT GTG ACA GAG CAG ACC AAT CAC    1460
Arg Ser Val Asp Leu Gly Glu Asp Asn Val Thr Glu Gln Thr Asn His
                435             440             445

ATT ATT ATT CCT AGT TAT GCA TCA TGG TTT GAT TAT AAC TGT ATT CAT    1508
Ile Ile Ile Pro Ser Tyr Ala Ser Trp Phe Asp Tyr Asn Cys Ile His
    450             455             460

GTG ATT GAA CGG CGT GCT CTT CCT GAG TTC TTC AAT GGA AAA AAC AAA    1556
Val Ile Glu Arg Arg Ala Leu Pro Glu Phe Phe Asn Gly Lys Asn Lys
465             470             475             480

TCC AAG ACT CCA GAA ATA TAC TTG GCA TAT CGA AAT TTT ATG ATT GAC    1604
Ser Lys Thr Pro Glu Ile Tyr Leu Ala Tyr Arg Asn Phe Met Ile Asp
                485             490             495

ACG TAT CGT CTA AAC CCC CAA GAG TAT TTA ACT AGC ACT GCT TGT CGG    1652
Thr Tyr Arg Leu Asn Pro Gln Glu Tyr Leu Thr Ser Thr Ala Cys Arg
            500             505             510

AGG AAC TTG ACT GGA GAT GTG TGT GCT GTG ATG AGG GTC CAT GCC TTT    1700
Arg Asn Leu Thr Gly Asp Val Cys Ala Val Met Arg Val His Ala Phe
                515             520             525

TTA GAG CAG TGG GGA CTC GTT AAT TAC CAA GTT GAC CCG GAA AGT AGA    1748
Leu Glu Gln Trp Gly Leu Val Asn Tyr Gln Val Asp Pro Glu Ser Arg
    530             535             540

CCC ATG GCA ATG GGA CCT CCT CCT ACT CCT CAT TTT AAT GTA TTA GCT    1796
Pro Met Ala Met Gly Pro Pro Pro Thr Pro His Phe Asn Val Leu Ala
545             550             555             560

GAT ACC CCC TCT GGG CTT GTG CCT CTG CAT CTT CGA TCA CCT CAG GTT    1844
Asp Thr Pro Ser Gly Leu Val Pro Leu His Leu Arg Ser Pro Gln Val
```

TABLE 1-continued

Human p150 nucleic acid and predicted amino acid sequence.
SEQ ID NO: 1 and 2. The SWI3 conserved domain runs from about
Asp440 through Pro563. The MYB-like domain runs from about Thr610
through Glu720. The coiled-coiled region runs from about Glu860
through Gln940.

```
                565                    570                    575
CCT GCT GCT CAA CAG ATG CTA AAT TTT CCT GAG AAA AAC AAG GAA AAA   1892
Pro Ala Ala Gln Gln Met Leu Asn Phe Pro Glu Lys Asn Lys Glu Lys
            580                    585                    590

CCA GTT GAT TTG CAG AAC TTT GGT CTC CGT ACT GAC ATT TAC TCC AAG   1940
Pro Val Asp Leu Gln Asn Phe Gly Leu Arg Thr Asp Ile Tyr Ser Lys
            595                    600                    605

AAA ACA TTA GCA AAG AGT AAA GGT GCT AGT GCT GGA AGA GAA TGG ACT   1988
Lys Thr Leu Ala Lys Ser Lys Gly Ala Ser Ala Gly Arg Glu Trp Thr
610                    615                    620

GAA CAG GAG ACC CTT CTA CTC CTG GAG GCC CTG GAG ATC TAC AAG GAT   2036
Glu Gln Glu Thr Leu Leu Leu Glu Ala Leu Glu Met Tyr Lys Asp
625                    630                    635                    640

GAT TGG AAC AAA GTG TCG GAA CAT GTT GGA AGT CGT ACT CAG GAT GAA   2084
Asp Trp Asn Lys Val Ser Glu His Val Gly Ser Arg Thr Gln Asp Glu
            645                    650                    655

TGC ATC CTC CAC TTT TTG AGA CTT CCC ATT GAG GAC CCA TAC CTT GAG   2132
Cys Ile Leu His Phe Leu Arg Leu Pro Ile Glu Asp Pro Tyr Leu Glu
            660                    665                    670

AAT TCA GAT GCT TCC CTT GGG CCT TTG GCC TAC CAG CCT GTC CCC TTC   2180
Asn Ser Asp Ala Ser Leu Gly Pro Leu Ala Tyr Gln Pro Val Pro Phe
            675                    680                    685

AGT CAG TCA GGA AAT CCA GTT ATG AGT ACT GTT GCT TTT TTG GCA TCT   2228
Ser Gln Ser Gly Asn Pro Val Met Ser Thr Val Ala Phe Leu Ala Ser
            690                    695                    700

GTG GTG GAC CCT CGC GTG GCA TCT GCT GCA GCA AAA GCG GCT TTG GAG   2276
Val Val Asp Pro Arg Val Ala Ser Ala Ala Ala Lys Ala Ala Leu Glu
705                    710                    715                    720

GAG TTT TCT CGG GTC CGG GAG GAG GTA CCA CTG GAA TTG GTT GAA GCT   2324
Glu Phe Ser Arg Val Arg Glu Glu Val Pro Leu Glu Leu Val Glu Ala
            725                    730                    735

CAT GTC AAG AAA GTA CAA GAA GCA GCA CGA GCC TCT GGG AAA GTG GAT   2372
His Val Lys Lys Val Gln Glu Ala Ala Arg Ala Ser Gly Lys Val Asp
            740                    745                    750

CCC ACC TAC GGT CTG GAG AGC AGC TGC ATT GCA GGC ACA GGG CCC GAT   2420
Pro Thr Tyr Gly Leu Glu Ser Ser Cys Ile Ala Gly Thr Gly Pro Asp
            755                    760                    765

GAG CCA GAG AAG CTT GAA GGA GCT GAA GAG GAA AAA ATG GAA GCC GAC   2468
Glu Pro Glu Lys Leu Glu Gly Ala Glu Glu Glu Lys Met Glu Ala Asp
            770                    775                    780

CCT GAT GGT CAG CAG CCT GAA AAG GCA GAA AAT AAA GTG GAA AAT GAA   2516
Pro Asp Gly Gln Gln Pro Glu Lys Ala Glu Asn Lys Val Glu Asn Glu
785                    790                    795                    800

ACG GAT GAA GGT GAT AAA GCA CAA GAT GGA GAA AAT GAA AAA AAT AGT   2564
Thr Asp Glu Gly Asp Lys Ala Gln Asp Gly Glu Asn Glu Lys Asn Ser
            805                    810                    815

GAA AAG GAA CAG GAT AGT GAA GTG AGT GAG GAT ACC AAA TCA GAA GAA   2612
Glu Lys Glu Gln Asp Ser Glu Val Ser Glu Asp Thr Lys Ser Glu Glu
            820                    825                    830

AAG GAG ACT GAA GAG AAC AAA GAA CTC ACT GAT ACA TGT AAA GAA AGA   2660
Lys Glu Thr Glu Glu Asn Lys Glu Leu Thr Asp Thr Cys Lys Glu Arg
            835                    840                    845

GAA AGT GAT ACT GGG AAG AAG AAA GTA GAA CAT GAA ATT TCC GAA GGA   2708
Glu Ser Asp Thr Gly Lys Lys Lys Val Glu His Glu Ile Ser Glu Gly
            850                    855                    860
```

TABLE 1-continued

Human p150 nucleic acid and predicted amino acid sequence.
SEQ ID NO: 1 and 2. The SWI3 conserved domain runs from about
Asp440 through Pro563. The MYB-like domain runs from about Thr610
through Glu720. The coiled-coiled region runs from about Glu860
through Gln940.

```
AAT GTT GCC ACA GCC GCA GCA GCT GCT CTT GCC TCA GCG GCT ACC AAA  2756
Asn Val Ala Thr Ala Ala Ala Ala Ala Leu Ala Ser Ala Ala Thr Lys
865                 870                 875                 880

GCC AAG CAC CTG GCT GCA GTG GAA GAA AGA AAG ATC AAG TCC CTG GTA  2804
Ala Lys His Leu Ala Ala Val Glu Glu Arg Lys Ile Lys Ser Leu Val
                    885                 890                 895

GCT CTC TTG GTT GAG ACA CAA ATG AAG AAA CTA GAG ATC AAA CTT CGA  2852
Ala Leu Leu Val Glu Thr Gln Met Lys Lys Leu Glu Ile Lys Leu Arg
                900                 905                 910

CAT TTT GAA GAG CTG GAA ACT ATC ATG GAC AGA GAG AAA GAA GCT CTA  2900
His Phe Glu Glu Leu Glu Thr Ile Met Asp Arg Glu Lys Glu Ala Leu
            915                 920                 925

GAA CAA CAG AGG CAG CAG TTG CTT ACT GAA CGC CAA AAC TTC CAC ATG  2948
Glu Gln Gln Arg Gln Gln Leu Leu Thr Glu Arg Gln Asn Phe His Met
        930                 935                 940

GAA CAG CTG AAG TAT GCT GAA TTA CGA GCA CGA CAG CAA ATG GAA CAG  2996
Glu Gln Leu Lys Tyr Ala Glu Leu Arg Ala Arg Gln Gln Met Glu Gln
945                 950                 955                 960

CAG CAG CAT GGC CAG AAC CCT CAA CAG GCA CAC CAG CAC TCA GGA GGA  3044
Gln Gln His Gly Gln Asn Pro Gln Gln Ala His Gln His Ser Gly Gly
                    965                 970                 975

CCT GGC CTG GCC CCA CTT GGA GCA GCA GGG CAC CCT GGC ATG ATG CCT  3092
Pro Gly Leu Ala Pro Leu Gly Ala Ala Gly His Pro Gly Met Met Pro
                980                 985                 990

CAT CAA CAG CCC CCT CCC TAC CCT CTG ATG CAC CAC CAG ATG CCA CCA  3140
His Gln Gln Pro Pro Pro Tyr Pro Leu Met His His Gln Met Pro Pro
            995                 1000                1005

CCT CAT CCA CCC CAG CCA GGT CAG ATA CCA GGC CCA GGT TCC ATG ATG  3188
Pro His Pro Pro Gln Pro Gly Gln Ile Pro Gly Pro Gly Ser Met Met
        1010                1015                1020

CCC GGG CAG CAC ATG CCA GGC CGC ATG ATT CCC ACT GTT GCA GCC AAC  3236
Pro Gly Gln Hls Met Pro Gly Arg Met Ile Pro Thr Val Ala Ala Asn
1025                1030                1035                1040

ATC CAC CCC TCT GGG AGT GGC CCT ACC CCT CCT GGC ATG CCA CCA ATG  3284
Ile His Pro Ser Gly Ser Gly Pro Thr Pro Pro Gly Met Pro Pro Met
                    1045                1050                1055

CCA GGA AAC ATC TTA GGA CCC CGG GTA CCC CTG ACA GCA CCT AAC GGC  3332
Pro Gly Asn Ile Leu Gly Pro Arg Val Pro Leu Thr Ala Pro Asn Gly
                1060                1065                1070

ATG TAT CCC CCT CCA CCA CAG CAG CAG CCA CCG CCA CCA CCA CCT GCA  3380
Met Tyr Pro Pro Pro Pro Gln Gln Gln Pro Pro Pro Pro Pro Pro Ala
            1075                1080                1085

GAT GGG GTC CCT CCG CCT CCT GCT CCT GGC CCG CCA GCC TCA GCT GCT  3428
Asp Gly Val Pro Pro Pro Pro Ala Pro Gly Pro Pro Ala Ser Ala Ala
        1090                1095                1100

CCT TAGCCTGGAA GATGCAGGGA ACCTCCACGC CCACCACCAT GAGCTGGAGT        3481
Pro
1105

GGGGATGACA AGACTTGTGT TCCTCAACTT TCTTGGTTTC TTTCAGGATT TTTCTTCTCA 3541

CAGCTCCAAG CACGTGTCCC GTGCCTCCCC ACTCCTCTTA CCACCCCTCT CTCTGACACT 3601

TTTTGTGTTG GGTCCTCAGC CAACACTCAA GGGGAAACCT GTAGTGACAG TGTGCCCTGG 3661

TCATCCTTAA AATAACCTGC ATCTCCCCTG TCCTGGTGTG GGAGTAAGCT GACAGTTTCT 3721
```

TABLE 1-continued

Human p150 nucleic acid and predicted amino acid sequence.
SEQ ID NO: 1 and 2. The SWI3 conserved domain runs from about
Asp440 through Pro563. The MYB-like domain runs from about Thr610
through Glu720. The coiled-coiled region runs from about Glu860
through Gln940.

```
CTGCAGGTCC TGTCAACTTT AGCATGCTAT GTCTTTACCA TTTTTGCTCT CTTGCAGTTT 3781

TTTGCTTTGT CTTATGCTTC TATGGATAAT GCTATATAAT CATTATCTTT TTATCTTTCT 3841

GTTATTATTG TTTTAAAGGA GAGCATCCTA AGTTAATAGG AACCAAAAAA TAATGATGGG 3901

CAGAAGGGGG GGAATAGCCA CAGGGGACAA ACCTTAAGGC ATTATAAGTG ACCTTATTTC 3961

TGCTTTTCTG AGCTAAGAAT GGTGCTGATG GTAAAGTTTG AGACTTTTGC CACACACAAA 4021

TTTGTGAAAA TTAAACGAGA TGTTGGAAGG AGAAAAAAAA AAAAAAAAAA GGGCGGCCGC 4081
```

TABLE 2

Partial human p130 nucleic acid and predicted amino acid
sequence. SEQ ID NO: 3 and 4. See SEQ ID NO: 11, 12, AND 13.

```
ATG GAG GCG CAA CTT CCA GTG CTC GTA AAA ACA GAT GGG ATG AAA CCC    48
Met Glu Ala Gln Leu Pro Val Leu Val Lys Thr Asp Gly Met Lys Pro
 1               5                  10                  15

CCA AAA CAG AGA GAG ATA CTC TTG GGC ATG GAA GTG GAT GGG GTG AGA    96
Pro Lys Gln Arg Glu Ile Leu Leu Gly Met Glu Val Asp Gly Val Arg
            20                  25                  30

CTC CTC GAA CAG ATC GAG GCG GAG ATT ATA TTG GTG AAA CAC CGA CTC   144
Leu Leu Glu Gln Ile Glu Ala Glu Ile Ile Leu Val Lys His Arg Leu
        35                  40                  45

CTG GAG CCA GTA AAA GAA ACT CAC GGT GGG ATG AAA CAC CAG CTA GTC   192
Leu Glu Pro Val Lys Glu Thr His Gly Gly Met Lys His Gln Leu Val
    50                  55                  60

AGA TGG GTG GAA GCA CTC CCA GTT CTG ACC CCT GGA AAG ACA CCA ATT   240
Arg Trp Val Glu Ala Leu Pro Val Leu Thr Pro Gly Lys Thr Pro Ile
65                  70                  75                  80

GGC ACA CCA GCC ATG AAC ATG GCT ACC CCT ACT CCA GGT CAC ATA ATG   288
Gly Thr Pro Ala Met Asn Met Ala Thr Pro Thr Pro Gly His Ile Met
                85                  90                  95

AGT ATG ACT CCT GAA CAG CTT CAG GCT TCG GCG TGC GAA AGA GAA ATT   336
Ser Met Thr Pro Glu Gln Leu Gln Ala Trp Arg Trp Glu Arg Glu Ile
            100                 105                 110

GAT GAG AGA AAT CGC CCA CTT TCT GAT GAG GAA TTA GAT GCT ATG TTC   384
Asp Glu Arg Asn Arg Pro Leu Ser Asp Glu Glu Leu Asp Ala Met Phe
        115                 120                 125

CCA GAA GGA TAT AAG GTA CTT CCT CCT CCA GCT GGT TAT GTT CCT ATT   432
Pro Glu Gly Tyr Lys Val Leu Pro Pro Pro Ala Gly Tyr Val Pro Ile
    130                 135                 140

CGA ACT CCA GCT CGA AAG CTG ACA GCT ACT CCA ACA CCT TTG GGT GGT   480
Arg Thr Pro Ala Arg Lys Leu Thr Ala Thr Pro Thr Pro Leu Gly Gly
145                 150                 155                 160

ATG ACT GGT TTC CAC ATG CAA ACT GAA GAT CGA ACT ATG AAA AGT GTT   528
Met Thr Gly Phe His Met Gln Thr Glu Asp Arg Thr Met Lys Ser Val
                165                 170                 175

AAT GAC CAG CCA TCT GGA AAT CTT CCA TTT TTA AAA CCT CAT GAT ATT   576
Asn Asp Gln Pro Ser Gly Asn Leu Pro Phe Leu Lys Pro His Asp Ile
            180                 185                 190

CAA TAC TTT GAT AAA CTA TTG GTT GAT GTT GAT GAA TCA ACA CTT AGT   624
Gln Tyr Phe Asp Lys Leu Leu Val Asp Val Asp Glu Ser Thr Leu Ser
        195                 200                 205

CCA GAA GAG CAA AAA AAA ...                                        642
```

TABLE 2-continued

Partial human p130 nucleic acid and predicted amino acid sequence. SEQ ID NO: 3 and 4. See SEQ ID NO: 11, 12, AND 13.

Pro Glu Glu Gln Lys Lys ...
210

TABLE 3

Human VCP nucleic acid and predicated amino sequence.
SEQ ID NO: 5 and 6.

| | |
|---|---|
| GGAATTCCCG GGTCGACCCA CGCGTCCGCG TCGCTGCCGC TGCCGCTGCC ACTGCCACTG | 60 |
| CCACCTCGCG GATCAGGAGC CAGCGTTGTT CGCCCGACGC CTCGCTGCCG GTGGGAGGAA | 120 |
| GCGAGAGGGA AGCCGCTTGC GGGTTTGTCG CCGCTGCTCG CCCACCGCCT GGAAGAGCCG | 180 |
| AGCCCCGGCC CAGTCGGTCG CTTGCCACCG CTCGTAGCCG TTACCCGCGG GCCGCCACAG | 240 |
| CCGCCGGCCG GGAGAGGCGC GCGCC ATG GCT TCT GGA GCC GAT TCA AAA GGT | 292 |

```
                         Met Ala Ser Gly Ala Asp Ser Lys Gly
                          1               5
GAT GAC CTA TCA ACA GCC ATT CTC AAA CAG AAG AAC CGT CCC AAT CGG     340
Asp Asp Leu Ser Thr Ala Ile Leu Lys Gln Lys Asn Arg Pro Asn Arg
 10              15                  20                  25
TTA ATT GTT GAT GAA GCC ATC AAT GAG GAC AAC AGT GTG GTG TCC TTG     388
Leu Ile Val Asp Glu Ala Ile Asn Glu Asp Asn Ser Val Val Ser Leu
                 30                  35                  40
TCC CAG CCC AAG ATG GAT GAA TTG CAG TTG TTC CGA GGT GAC ACA GTG     436
Ser Gln Pro Lys Met Asp Glu Leu Gln Leu Phe Arg Gly Asp Thr Val
                 45                  50                  55
TTG CTG AAA GGA AAG AAG AGA CGA GAA GCT GTT TGC ATC GTC CTT TCT     484
Leu Leu Lys Gly Lys Lys Arg Arg Glu Ala Val Cys Ile Val Leu Ser
                 60                  70
GAT GAT ACT TGT TCT GAT GAG AAG ATT CGG ATG AAT AGA GTT GTT CGG     532
Asp Asp Thr Cys Ser Asp Glu Lys Ile Arg Met Asn Arg Val Val Arg
         75                  80                  85
AAT AAC CTT CGT GTA CGC CTA GGG GAT GTC ATC AGC ATC CAG CCA TGC     580
Asn Asn Leu Arg Val Arg Leu Gly Asp Val Ile Ser Ile Gln Pro Cys
 90                  95                 100                 105
CCT GAT GTG AAG TAC GGC AAA CGT ATC CAT GTG CTG CCC ATT GAT GAC     628
Pro Asp Val Lys Tyr Gly Lys Arg Ile His Val Leu Pro Ile Asp Asp
                110                 115                 120
ACA GTG GAA GGC ATT ACT GGT AAT CTC TTC GAG GTA TAC CTT AAG CCG     676
Thr Val Glu Gly Ile Thr Gly Asn Leu Phe Glu Val Tyr Leu Lys Pro
                125                 130                 135
TAC TTC CTG GAA GCG TAT CGA CCC ATC CGG AAA GGA GAC ATT TTT CTT     724
```

TABLE 3-continued

Human VCP nucleic acid and predicated amino sequence.
SEQ ID NO: 5 and 6.

```
Tyr Phe Leu Glu Ala Tyr Arg Pro Ile Arg Lys Gly Asp Ile Phe Leu
        140                 145                 150
GTC CGT GGT GGG ATG CGT GCT GTG GAG TTC AAA GTG GTG GAA ACA GAT    772
Val Arg Gly Gly Met Arg Ala Val Glu Phe Lys Val Val Glu Thr Asp
        155                 160                 165
CCT AGC CCT TAT TGC ATT GTT GCT CCA GAC ACA GTG ATC CAC TGC GAA    820
Pro Ser Pro Tyr Cys Ile Val Ala Pro Asp Thr Val Ile His Cys Glu
170                 175                 180                 185
GGG GAG CCT ATC AAA CGA GAG GAT GAG GAA GAG TCC TTG AAT GAA GTA    868
Gly Glu Pro Ile Lys Arg Glu Asp Glu Glu Glu Ser Leu Asn Glu Val
                190                 195                 200
GGG TAT GAT GAC ATT GGT GGC TGC AGG AAG CAG CTA GCT CAG ATA AAG    916
Gly Tyr Asp Asp Ile Gly Gly Cys Arg Lys Gln Leu Ala Gln Ile Lys
                205                 210                 215
GAG ATG GTG GAA CTG CCC CTG AGA CAT CCT GCC CTC TTT AAG GCA ATT    964
Glu Met Val Glu Leu Pro Leu Arg His Pro Ala Leu Phe Lys Ala Ile
            220                 225                 230
GGT GTG AAG CCT CCT AGA GGA ATC CTG CTT TAC GGA CCT CCT GGA ACA    1012
gly val lys pro pro arg gly ile leu leu tyr gly pro pro gly thr
            235                 240                 245
GGA AAG ACC CTG ATT GCT CGA GCT GTA GCA AAT GAG ACT GGA GCC TTC    1060
Gly Lys Thr Leu Ile Ala Arg Ala Val Ala Asn Glu Thr Gly Ala Phe
250                 255                 260                 265
TTC TTC TTG ATC AAT GGT CCT GAG ATC ATG AGC AAA TTG GCT GGT GAG    1108
phe phe leu ile asn gly pro glu ile met ser lys leu ala gly glu
                270                 275                 280
TCT GAG AGC AAC CTT CGT AAA GCC TTT GAG GAG GCT GAG AAG AAT GCT    1156
Ser Glu Ser Asn Leu Arg Lys Ala Phe Glu Glu Ala Glu Lys Asn Ala
                300                 305                 310
GAG AAA ACT CAT GGC GAG GTG GAG CGG CGC ATT GTA TCA CAG TTG TTG    1252
Glu Lys Thr His Gly Glu Val Glu Arg Arg Ile Val Ser Gln Leu Leu
            315                 320                 325
ACC CTC ATG GAT GGC CTA AAG CAG AGG GCA CAT GTG ATT GTT ATG GCA    1300
Thr Leu Met Asp Gly Leu Lys Gln Arg Ala His Val Ile Val Met Ala
330                 335                 340                 345
GCA ACC AAC AGA CCC AAC AGC ATT GAC CCA GCT CTA CGG CGA TTT GTT    1348
ala thr asn arg pro asn ser ile asp pro ala leu arg arg phe gly
                350                 355                 360
```

TABLE 3-continued

Human VCP nucleic acid and predicated amino sequence.
SEQ ID NO: 5 and 6.

```
CGC TTT GAC AGG GAG GTA GTA ATT GGA ATT CCT GAT GCT ACA GGA CGC     1396
Arg Phe Asp Arg Glu Val Val Ile Gly Ile Pro Asp Ala Thr Gly Arg
            365                 370                 375
TTA GAG ATT CTT CAG ATC CAT ACC AAG AAC ATG AAG CTG GCA GAT GAT     1444
Leu Glu Ile Leu Gln Ile His Thr Lys Asn Met Lys Leu Ala Asp Asp
            180                 385                 390
GTG GAC CTG GAA CAG GTA GCC AAT GAG ACT CAC GGG CAT GTG GGT GCT     1492
Val Asp Leu Glu Gln Val Ala Asn Glu Thr His Gly His Val Gly Ala
            395                 400                 405
GAC TTA GCA GCC CTG TGC TCA GAG GCT GCT CTG CAA GCC ATC CGC AAG     1540
Asp Leu Ala Ala Leu Cys Ser Glu Ala Ala Leu Gln Ala Ile Arg Lys
410                 415                 420                 425
AAG ATG GAT CTC ATT GAC CTA GAG GAT GAG ACC ATT GAT GCC GAG GTC     1588
Lys Met Asp Leu Ile Asp Leu Glu Asp Glu Thr Ile Asp Ala Glu Val
                    430                 435                 440
ATG AAC TCT CTA GCA GTT ACT ATG GAT GAC TTC CGG TGG GCC TTG AGC     1636
Met Asn Ser Leu Ala Val Thr Met Asp Asp Phe Arg Trp Ala Leu Ser
            445                 450                 455
CAG AGT AAC CCA TCA GCA CTG CGG GAA ACC GTG GTA GAG GTG CCA CAG     1684
Gln Ser Asn Pro Ser Ala Leu Arg Glu Thr Val Val Glu Val Pro Gln
            460                 465                 470
GTA ACC TGG GAA GAC ATC GGG GGC CTA GAG GAT GTC AAA CGT GAG CTA     1732
Val Thr Trp Glu Asp Ile Gly Gly Leu Glu Asp Val Lys Arg Glu Leu
    475                 480                 485
CAG GAG CTG GTC CAG TAT CCT GTG GAG CAC CCA GAC AAA TTC CTG AAG     1780
Gln Glu Leu Val Gln Tyr Pro Val Glu His Pro Asp Lys Phe Leu Lys
490                 495                 500                 505
TTT GGC ATG ACA CCT TCC AAG GGA GTT CTG TTC TAT GGA CCT CCT GGC     1828
Phe Gly Met Thr Pro Ser Lys Gly Val Leu Phe Tyr Gly Pro Pro Gly
                510                 515                 520
GTG GGG AAA ACT TTG TTG GCC AAA GCC ATT GCT AAT GAA TGC CAG GCC     1876
Cys Gly Lys Thr Leu Leu Ala Lys Ala Ile Ala Asn Glu Cys Gln Ala
            525                 530                 535
AAC TTC ATC TCC ATC AAG GGT CCT GAG CTG CTC ACC ATG TGG TTT GGG     1924
Asn Phe Ile Ser Ile Lys Gly Pro Glu Leu Leu Thr Met Trp Phe Gly
            540                 545                 550
GAG TCT GAG GCC AAT GTC AGA GAA ATC TTT GAC AAG GCC CGC CAA GCT     1972
```

TABLE 3-continued

Human VCP nucleic acid and predicated amino sequence.
SEQ ID NO: 5 and 6.

| | | | | | | | | | | | | |
|---|---|---|---|---|---|---|---|---|---|---|---|---|
| Glu | Ser | Glu | Ala | Asn | Val | Arg | Glu | Ile | Phe | Asp | Lys | Ala | Arg | Gln | Ala |
| | | 555 | | | | 560 | | | | 565 | | | | | |

GCC CCC TGT GTG CTA TTC TTT GAT GAG CTG GAT TCG ATT GCC AAG GCT     2020
Ala Pro Cys Val Leu Phe Phe Asp Glu Leu Asp Ser Ile Ala Lys Ala
570                 575               580             585

CGT GGA GGT AAC ATT GGA GAT GGT GGT GGG GCT GCT GAC CGA GTC ATC     2068
Arg Gly Gly Asn Ile Gly Asp Gly Gly Gly Ala Ala Asp Arg Val Ile
             590               595             600

AAC CAG ATC CTG ACA GAA ATG GAT GGC ATG TCC ACA AAA AAA AAT GTG     2116
Asn Gln Ile Leu Thr Glu Met Asp Gly Met Ser Thr Lys Lys Asn Val
             605               610             615

TTC ATC ATT GGC GCT ACC AAC CGG CCT GAC ATC ATT GAT CCT GCC ATC     2164
Phe Ile Ile Gly Ala Thr Asn Arg Pro Asp Ile Ile Asp Pro Ala Ile
             620               625             630

CTC AGA CCT GGC CGT CTT GAT CAG CTC ATC TAC ATC CCA CTT CCT GAT     2212
Leu Arg Pro Gly Arg Leu Asp Gln Leu Ile Tyr Ile Pro Leu Pro Asp
   635               640               645

GAG AAG TCC CGT GTT GCC ATC CTC AAG GCT AAC CTG CGC AAG TCC CCA     2260
Glu Lys Ser Arg Val Ala Ile Leu Lys Ala Asn Leu Arg Lys Ser Pro
650                 655               660             665

GTT GCC AAG GAT GTG GAC TTG GAG TTC CTG GCT AAA ATG ACT AAT GGC     2308
Val Ala Lys Asp Val Asp Leu Glu Phe Leu Ala Lys Met Thr Asn Gly
             670               675             680

TTC TCT GGA GCT GAC CTG ACA GAG ATT TGC CAG CGT GCT TGC AAG CTG     2356
Phe Ser Gly Ala Asp Leu Thr Glu Ile Cys Gln Arg Ala Cys Lys Leu
             685               690             695

GCC ATC CGT GAA TCC ATC GAG AGT GAG ATT AGG CGA GAA CGA GAG AGG     2404
ala ile arg glu ser ile glu ser glu ile arg arg glu arg glu arg
             700               705             710

CAG ACA AAC CCA TCA GAA ATG GAG GTA GAA GAG GAT GAT CCA GTG CCT     2452
Gln Thr Asn Pro Ser Ala Met Glu Val Glu Glu Asp Asp Pro Val Pro
   715               720               725

GAG ATC CGT CGA GAT CAC TTT GAA GAA GCC ATG CGC TTT GCG CGC CGT     2500
Glu Ile Arg Arg Asp His Phe Glu Glu Ala Met Arg Phe Ala Arg Arg
730                 735               740             745

TCT GTC AGT GAC AAT GAC ATT CGG AAG TAT GAG ATG TTT GCC CAG ACC     2548
Ser Val Ser Asp Asn Asp Ile Arg Lys Tyr Glu Met Phe Ala Gln Thr
             750               755             760

TABLE 3-continued

Human VCP nucleic acid and predicated amino sequence.
SEQ ID NO: 5 and 6.

| | | | | | | | | | | | | | | | |
|---|---|---|---|---|---|---|---|---|---|---|---|---|---|---|---|
| CTT | CAG | CAG | AGT | CGG | GGC | TTT | GGC | AGC | TTC | AGA | TTC | CCT | TCA | GGG AAC | 2596 |
| Leu | Gln | Gln | Ser | Arg | Gly | Phe | Gly | Ser | Phe | Arg | Phe | Pro | Ser | Gly Asn | |
| | | | 765 | | | | 770 | | | | 775 | | | | |
| CAG | GGT | GGA | GCT | GGC | CCC | AGT | CAG | GGC | AGT | GGA | GGC | GGC | ACA | GGT GGC | 2644 |
| Gln | Gly | Gly | Ala | Gly | Pro | Ser | Gln | Gly | Ser | Gly | Gly | Gly | Thr | Gly Gly | |
| | | | 780 | | | | 785 | | | | 790 | | | | |
| AGT | GTA | TAC | ACA | GAA | GAC | AAT | GAT | GAT | GAC | CTG | TAT | GGC | TAAGTGGTGG | | 2693 |
| ser | val | tyr | thr | glu | asp | asn | asp | asp | asp | leu | tyr | gly | | | |
| | | | 795 | | | | 800 | | | | 805 | | | | |

TGGCCAGCGT GCAGTGAGCT GGCCTGCCTG GACCTTGTTC CCTGGGGGTG GGGGCGCTTG 2753
CCCAGGAGAG GGACCAGGGG TGCGCCCACA GCCTGCTCCA TTCTCCAGTC TGAACAGTTC 2813
AGCTACAGTC TGACTCTGGA CAGGGTGTTT CTGTTGCAAA ATACAAAAC AAAAGCGATA 2873
AAATTAAAGC GATTTTCATT TGGAAAAAAA AAAAAAAAA AAAAAAAAG GCGGCCGC 2932

TABLE 4

Human tsg101 nucleic acid and predicted amino acid
sequence. SEQ ID NO: 7 and 8.

| | | | | | | | | | | | | | | | |
|---|---|---|---|---|---|---|---|---|---|---|---|---|---|---|---|
| GGACGCGTGG | GGGACGGTCT | GGGGCAGCCC | AGCAGCGCT | GACCCTCTGC | CTGCGGGGAA | | | | | | | | | | 60 |
| GGGAGTCGCC | AGGCGGCCGT | C ATG | GCG | GTG | TCG | GAG | AGC | CAG | CTC | AAG | AAA | | | | 111 |
| | | Met | Ala | Val | Ser | Glu | Ser | Gln | Leu | Lys | Lys | | | | |
| | | 1 | | | 5 | | | | | 10 | | | | | |
| ATG | GTG | TCC | AAG | TAC | AAA | TAC | AGA | GAC | CTA | ACT | GTA | CGT | GAA | ACT GTC | 159 |
| Met | Val | Ser | Lys | Tyr | Lys | Tyr | Arg | Asp | Leu | Thr | Val | Arg | Glu | Thr Val | |
| | | | 15 | | | | 20 | | | | 25 | | | | |
| AAT | GTT | ATT | ACT | GTA | TAC | AAA | GAT | CTC | AAA | CCT | GTG | TTG | GAT | TCA TAT | 207 |
| Asn | Val | Ile | Thr | Leu | Tyr | Lys | Asp | Leu | Lys | Pro | Val | Leu | Asp | Ser Tyr | |
| | | | 30 | | | | 35 | | | | 40 | | | | |
| GTT | TTT | AAC | GAT | GGC | AGT | TCC | AGG | GAA | CTA | ATG | AAC | CTC | ACT | GGA ACA | 255 |
| Val | Phe | Asn | Asp | Gly | Ser | Ser | Arg | Glu | Leu | Met | Asn | Leu | Thr | Gly Thr | |
| | | | 45 | | | | 50 | | | | 55 | | | | |
| ATC | CCT | GTG | CCT | TAT | AGA | GGT | AAT | ACA | TAC | AAT | ATT | CCA | ATA | TGC CTA | 303 |
| Ile | Pro | Val | Pro | Tyr | Arg | Gly | Asn | Thr | Tyr | Asn | Ile | Pro | Ile | Cys Leu | |
| | | | 60 | | | | 65 | | | | 70 | | | | |
| TGG | CTA | CTG | GAC | ACA | TAC | CCA | TAT | AAT | CCC | CCT | ATC | TGT | TTT | GTT AAG | 351 |
| Trp | Leu | Leu | Asp | Thr | Tyr | Pro | Tyr | Asn | Pro | Pro | Ile | Cys | Phe | Val Lys | |
| 75 | | | | 80 | | | | 85 | | | | 90 | | | |
| CCT | ACT | AGT | TCA | ATG | ACT | ATT | AAA | ACA | GGA | AAG | CAT | GTT | GAT | GCA AAT | 399 |

TABLE 4-continued

Human tsg101 nucleic acid and predicted amino acid
sequence. SEQ ID NO: 7 and 8.

```
            Pro Thr Ser Ser Met Thr Ile Lys Thr Gly Lys His Val Asp Ala Asn
                         95                 100                105
GGG AAG ATA TAT CTT CCT TAT CTA CAT GAA TGG AAA CAC CCA CAG TCA              447
Gly Lys Ile Tyr Leu Pro Tyr Leu His Glu Trp Lys His Pro Gln Ser
             110                 115                 120
GAC TTG TTG GGG CTT ATT CAG GTA ATG ATT GTG GTA TTT GGA GAT GAA              495
Asp Leu Leu Gly Leu Ile Gln Val Met Ile Val Val Phe Gly Asp Glu
         125                 130                 135
CCT CCA GTC TTC TCT CGT CCT ATT TCG GCA TCC TAT CCG CCA TAC CAG              543
Pro Pro Val Phe Ser Arg Pro Ile Ser Ala Ser Tyr Pro Pro Tyr Gln
         140                 145                 150
GCA ACG GGG CCA CCA AAT ACT TCC TAC ATG CCA GGC ATG CCA GGT GGA              591
Ala Thr Gly Pro Pro Asn Thr Ser Tyr Met Pro Gly Met Pro Gly Gly
155                 160                 165                 170
ATC TCT CAA TAC CCA TCC GGA TAC CCT CCC AAT CCC AGT GGT TAC CCA              639
Ile Ser Pro Tyr Pro Ser Gly Tyr Pro Pro Asn Pro Ser Gly Tyr Pro
                 175                         180                 185
GGC TGT CCT TAC CCA CCT GGT GGT CCA TAT CCT GCC ACA ACA AGT CT              687
Gly Cys Pro Tyr Pro Pro Gly Gly Pro Tyr Pro Ala Thr Thr Ser Ser
             190                 195                 200
CAG TAC CCT TCT CAG CCT CCT GTA CCA CTG TTG GTC CCA GTA GGG ATG              735
Gln Tyr Pro Ser Gln Pro Pro Val Pro Leu Leu Val Pro Val Gly Met
         205                 210                 215
GCA CAA TCA GCG AGG ACA CCA TCC GAG CTT CTC TCA TCT CTG CGG TCA              783
Ala Gln Ser Ala Arg Thr Pro Ser Glu Pro Leu Ser Ser Leu Arg Ser
GTG ACA AAC TGAGTGGCG GATGAAGGAG GAAATGGATC GTGCCCAGGC                       832
val thr asn
235
AGAGCTCAAT GCCTTGAAAC GAACAGAAGA AGACCTGAAA AAGGGTCACC AGAAACTGGA            892
AGAGATGGTT ACCCGTTTAG ATCAAGAAGT AGCCGAGGTT GATAAAAACA TAGAACTTTT            952
GAAAAAGAAG GATGAAGAAC TCAGTTCTGC TCTGGAAAAA ATGGAAAATC AGTCTGAAAA           1012
CAATGATATC GATGAAGTTA TCATTCCCAC AGCTCCCTTA TACAAACAGA TCCTGAATCT           1072
GTATGCAGAA GAAACGCTA TTGAAGACAC TATCTTTTAC TTGGGAGAAG CCTTGAGAAG            1132
GGGCGTGATA GACCTGGATG TCTTCCTGAA GCATGTATCT TCTGTCCCGT AAACAGTTCC           1192
AGCTGAGGGC ACTAATGCAA AAAGCAAAAG ACTGCCGGTC TCGTGACCTC TACTGACTTC           1252
TCTGATACCA GCTGGAGGTT GAGCTCTTCT TAAAGTAGTC TCTCTTCCTT TTATCAGTAG           1312
```

TABLE 4-continued

Human tsg101 nucleic acid and predicted amino acid sequence. SEQ ID NO: 7 and 8.

| | |
|---|---|
| GTGCCCAGAA TAAGTTATTG CAGTTTATCA TTCAAGTGTA AAATATTTTG AATCAATAAT | 1372 |
| ATATTTTCTG TTTTCTTTTG GTAAAAGACT GGCTTTTTAA TGCACTTTCT ATCCTCTGTA | 1432 |
| AACTTTTGTG CTGAATGTTG GGACTGCTAA ATAAAATTTG TTGCATAAAA AAAAAAAAAA | 1491 |

TABLE 5

Human KWC02 nucleic acid and amino acid sequences (SEQ ID NO: 9 and 10). Nucleotides 799 and 821 may be A, C, G, or T. Nucleotide 1128 may be A or C.

| | |
|---|---|
| TTTCCCGGGA GCCTGACCCG CCCCTGACGT CGCCTTTCCC GTCTCCGCAG GGTCCGGCCT | 60 |
| GCGCCTTCCC GCCAGGCCTG GACACTGGTT CAACACCTGT GACTTCATGT GTGCGCGCCG | 120 |
| GCCACACCTG CAGTCACACC TGTAGCCCCC TCTGCCAAGA GATCCATACC GAGGCAGCGT | 180 |
| CGGTGGCTAC AAGCCCTCAG TCCACACCTG TGGACACCTG TGACACCTGG CCACACGACC | 240 |
| TGTGGCCGCG GCCTGGCGTC TGCTGCGACA GGAGCCCTTA CCTCCCCTGT TATAACACCT | 300 |
| GACCGCCACC TAACTGCCCC TGCAGAAGGA GCA ATG GCC TTG GCT CCT GAG AGG | 354 |

Met Ala Leu Ala Pro Glu Arg
                                 1            5

| | |
|---|---|
| GCA GCC CCA CGC GTG CTG TTC GGA GAG TGG CTC CTT GGA GAG ATC AGC | 402 |
| Ala Ala Pro Arg Val Leu Phe Gly Glu Trp Leu Leu Gly Glu Ile Ser | |
|           10                 15                20 | |
| AGC GGC TGC TAT GAG GGG CTG CAG TGG CTG GAC GAG GCC CGC ACC TGT | 450 |
| Ser Gly Cys Tyr Glu Gly Leu Gln Trp Leu Asp Glu Ala Arg Thr Cys | |
|     25                 30                35 | |
| TTC CGC GTG CCC TGG AAG CAC TTC GCG CGC AAG GAC CTG AGC GAG GCC | 498 |
| Phe Arg Val Pro Trp Lys His Phe Ala Arg Lys Asp Leu Ser Glu Ala | |
|   40                 45                50                55 | |
| GAC GCG CGC ATC TTC AAG GCC TGG GCT GTG GCC CGC CGC AGG TGG CCG | 546 |
| Asp Ala Arg Ile Phe Lys Ala Trp Ala Val Ala Arg Arg Arg Trp Pro | |
|                60                65                70 | |
| CCT AGC AGC AGG GGA GGT GGC CCG CCC CCC GAG GCT GAG ACT GCG GAG | 594 |
| Pro Ser Ser Arg Gly Gly Gly Pro Pro Pro Glu Ala Glu Thr Ala Glu | |
|           75                 80                85 | |
| CGC GCC GGC TGG AAA ACC AAC TTC CGC TGC GCA CTG CGC AGC ACG CGT | 642 |
| Arg Ala Gly Trp Lys Thr Asn Phe Arg Cys Ala Leu Arg Ser Thr Arg | |
|                90                95               100 | |
| CGC TTC GTG ATG CTG CGG GAT AAC TCG GGG GAC CCG GCC GAC CCG CAC | 690 |
| Arg Phe Val Met Leu Arg Asp Asn Ser Gly Asp Pro Ala Asp Pro His | |
|      105               110               115 | |
| AAG GTG TAC GCG CTC AGC CGG GAG CTG TGC TGG CGA GAA GGC CCA GGC | 738 |
| Lys Val Tyr Ala Leu Ser Arg Glu Leu Cys Trp Arg Glu Gly Pro Gly | |

TABLE 5-continued

Human KWC02 nucleic acid and amino acid sequences (SEQ ID
NO: 9 and 10). Nucleotides 799 and 821 may be A, C, G, or T.
Nucleotide 1128 may be A or C.

```
        120                 125                 130                 135
ACG GAC CAG ACT GAG GCA GAG GCC CCC GCA GCT GCT CCA CCA CCA CAG          786
Thr Asp Gln Thr Glu Ala Glu Ala Pro Ala Ala Val Pro Pro Pro Gln
                    140                 145                 150
GGT GGG CCC CCA CGG CCA TTC CTG GCA CAC ACA CCT GCT GGA CTC CAA          834
Gly Gly Pro Pro Arg Pro Phe Leu Ala His Thr Pro Ala Gly Leu Gln
                    155                 160                 165
GCC CCA GGC CCC CTC CCT GCC CCA GCT GGT GAC AAG GGG GAC CTC CTG          882
Ala Pro Gly Pro Leu Pro Ala Pro Ala Gly Asp Lys Gly Asp Leu Leu
                    170                 175                 180
CTC CAG GCA GTG CAA CAG AGC TGC CTG GCA GAC CAT CTG CTG ACA GCG          930
Leu Gln Ala Val Gln Gln Ser Cys Leu Ala Asp His Leu Leu Thr Ala
                    185                 190                 195
TCA TGG GGG GCA GAT CCA GTC CCA ACC AAG GCT CCT GGA GAG GGA CAA          978
Ser Trp Gly Ala Asp Pro Val Pro Thr Lys Ala Pro Gly Glu Gly Gln
200                 205                 210                 215
GAA GGG CTT CCC CTG ACT GGG GCC TGT GCT GGA GGC CCA GGG CTC CCT         1026
Glu Gly Leu Pro Leu Thr Gly Ala Cys Ala Gly Gly Pro Gly Leu Pro
                    220                 225                 230
GCT GGG GAG CTG TAC GGG TGG GCA GTA GAG AAG ACC CCC AGC CCC GGG         1074
Ala Gly Glu Leu Tyr Gly Trp Ala Val Glu Lys Thr Pro Ser Pro Gly
                    235                 240                 245
CCC CAG CCC GCG GCA CTA ACG ACA GGC GAG GCC GCG GCC CCA GAG TCC         1122
Pro Gln Pro Ala Ala Leu Thr Thr Gly Glu Ala Ala Ala Pro Glu Ser
                    250                 255                 260
CCG CAC CAG GCA GAG CCG TAC CTG TCA CCC TCC CCA AGC GCC TGC ACC         1170
Pro His Gln Ala Glu Pro Tyr Leu Ser Pro Ser Pro Ser Ala Cys Thr
            265                 270                 275
GCG GTG CAA GAG CCC AGC CCA GGG GCG CTG GAC GTG ACC ATC ATG TAC         1218
Ala Val Gln Glu Pro Ser Pro Gly Ala Leu Asp Val Thr Ile Met Tyr
280                 285                 290                 295
AAG GGC CGC ACG GTG CTG CAG AAG GTG GTG GGA CAC CCG AGC TGC ACG         1266
Lys Gly Arg Thr Val Leu Gln Lys Val Val Gly His Pro Ser Cys Thr
                    300                 305                 310
TTC CTA TAC GGC CCC CCA GAC CCA GCT GTC CGG GCC ACA GAC CCC CAG         1314
Phe Leu Tyr Gly Pro Pro Asp Pro Ala Val aAg aAa tTr aAp Pro Gln
                    315                 320                 325
```

TABLE 5-continued

Human KWC02 nucleic acid and amino acid sequences (SEQ ID
NO: 9 and 10). Nucleotides 799 and 821 may be A, C, G, or T.
Nucleotide 1128 may be A or C.

```
CAG GTA GCA TTC CCC AGC CCT GCC GAG CTC CCG GAC CAG AAG CAG CTG      1362
Gln Val Ala Phe Pro Ser Pro Ala Glu Leu Pro Asp Gln Lys Gln Leu
        330                 335                 340
CGC TAC ACG GAG GAA CTG CTG CGG CAC GTG GCC CCT GGG TTG CAC CTG      1410
Arg Tyr Thr Glu Glu Leu Leu Arg His Val Ala Pro Gly Leu His Leu
        345                 350                 355
GAG CTT CGG GGG CCA CAG CTG TGG GCC CGG CGC ATG GGC AAG TGC AAG      1458
Glu Leu Arg Gly Pro Gln Leu Trp Ala Arg Arg Met Gly Lys Cys Lys
360                 365                 370                 375
GTG TAC TGG GAG GTG GGC GGA CCC CCA GGC TCC GCC AGC CCC TCC ACC      1506
Val Tyr Trp Glu Val Gly Gly Pro Pro Gly Ser Ala Ser Pro Ser Thr
                    380                 385                 390
CCA GCC TGC CTG CTG CCT CGG AAC TGT GAC ACC CCC ATC TTC GAC TTC      1554
Pro Ala Cys Leu Leu Pro Arg Asn Cys Asp Thr Pro Ile Phe Asp Phe
            395                 400                 405
AGA GTC TTC TTC CAA GAG CTG GTG GAA TTC CGG GCA CGG CAG CGC CGT      1602
Arg Val Phe Phe Gln Glu Leu Val Glu Phe Arg Ala Arg Gln Arg Arg
        410                 415                 420
GGC TCC CCA CGC TAT ACC ATC TAC CTG GGC TTC GGG CAG GAC CTG TCA      1650
Gly Ser Pro Arg Tyr Thr Ile Tyr Leu Gly Phe Gly Gln Asp Leu Ser
        425                 430                 435
GCT GGG AGG CCC AAG GAG AAG AGC CTG GTC CTG GTG AAG CTG GAA CCC      1698
Ala Gly Arg Pro Lys Glu Lys Ser Leu Val Leu Val Lys Leu Glu Pro
440                 445                 450                 455
TGG CTG TGC CGA GTG CAC CTA GAG GGC ACG CAG CGT GAG GGT GTG TCT      1746
Trp Leu Cys Arg Val His Leu Glu Gly Thr Gln Arg Glu Gly Val Ser
                    460                 465                 470
TCC CTG GAT AGC AGC AGC CTC AGC CTC TGC CTG TCC AGC GCC AAC AGC      1794
Ser Leu Asp Ser Ser Ser Leu Ser Leu Cys Leu Ser Ser Ala Asn Ser
            475                 480                 485
CTC TAT GAC GAC ATC GAG TGC TTC CTT ATG GAG CTG GAG CAG CCC GCC      1842
Leu Tyr Asp Asp Ile Glu Cys Phe Leu Met Glu Leu Glu Gln Pro Ala
        490                 495                 500
TAGAACCCAG TCTAATGAGA ACTCCAGAAA GCTGGAGCAG CCCACCTAGA GCTGGCCGCG   1902
GCCGCT                                                              1908
```

II. Definitions

The term "binding composition" refers to molecules that bind with specificity to a p150, p130, VCP, tsg101, or KWC02 protein, e.g., in an antibody-antigen interaction. However, other compounds, e.g., binding proteins, may also specifically associate with p150, p130, VCP, tsg101, or KWC02 proteins to the substantial exclusion of other molecules. Typically, the association will be in a natural physiologically relevant protein-protein interaction, either covalent or non-covalent, and may include members of a multiprotein complex, including carrier compounds or dimerization partners. The molecule may be a polymer, or chemical reagent. A functional analog may be a protein with structural modifications, or may be a wholly unrelated molecule, e.g., which has a molecular shape which interacts with the appropriate protein binding determinants. The proteins may serve as agonists or antagonists of the binding partner, see, e.g., Goodman, et al. (eds.) (1990) *Goodman & Gilman's: The Pharmacological Bases of Therapeutics* (8th ed.) Pergamon Press, Tarrytown, N.Y.

The term "binding agent:p150, p130, VCP, tsg101, or KWC02 protein complex", as used herein, refers to a complex of a binding agent and a p150, p130, VCP, tsg101, or KWC02 protein that is formed by specific binding of the binding agent to the respective p150, p130, VCP, tsg101, or KWC02 protein. Specific binding of the binding agent means that the binding agent has a specific binding site that recognizes a site on the p150, p130, VCP, tsg101, or KWC02 protein. For example, antibodies raised to a p150, p130, VCP, tsg101, or KWC02 protein and recognizing an epitope on the p150, p130, VCP, tsg101, or KWC02 protein are capable of forming a binding agent:p150, p130, VCP, tsg101, or KWC02 protein complex by specific binding. Typically, the formation of a binding agent:p150, p130, VCP, tsg101, or KWC02 protein complex allows the measurement of p150, p130, VCP, tsg101, or KWC02 protein in a mixture of other proteins and biologics. The term "antibody:p150, p130, VCP, tsg101, or KWC02 protein complex" refers to an embodiment in which the binding agent, e.g., is an antibody. The antibody may be monoclonal, polyclonal, or a binding fragment of an antibody, e.g., an Fv, Fab, or F(ab)2 fragment. The antibody will preferably be a polyclonal antibody for cross-reactivity purposes.

"Homologous" nucleic acid sequences, when compared, exhibit significant similarity, or identity. The standards for homology in nucleic acids are either measures for homology generally used in the art by sequence comparison and/or phylogenetic relationship, or based upon hybridization conditions. Hybridization conditions are described in greater detail below.

An "isolated" nucleic acid is a nucleic acid, e.g., an RNA, DNA, or a mixed polymer, which is substantially separated from other biologic components which naturally accompany a native sequence, e.g., proteins and flanking genomic sequences from the originating species. The term embraces a nucleic acid sequence which has been removed from its naturally occurring environment, and includes recombinant or cloned DNA isolates and chemically synthesized analogs, or analogs biologically synthesized by heterologous systems. A substantially pure molecule includes isolated forms of the molecule. An isolated nucleic acid will usually contain homogeneous nucleic acid molecules, but will, in some embodiments, contain nucleic acids with minor sequence heterogeneity. This heterogeneity is typically found at the polymer ends or portions not critical to a desired biological function or activity.

As used herein, the terms "p150", "p130", "VCP", "tsg101", or "KWC02" protein shall encompass, when used in a protein context, a protein having amino acid sequences shown in SEQ ID NO: 2, 4, 6, 8, or 10 or a significant fragment of such a protein, preferably a natural embodiment. The invention also embraces a polypeptide which exhibits similar structure to human p150, p130, VCP, tsg101, or KWC02 protein, e.g., which interacts with p150, p130, VCP, tsg101 $_1$, or KWC02 protein specific binding components. These binding components, e.g., antibodies, typically bind to a p150, p130, VCP, tsg101, or KWC02 protein, respectively, with high affinity, e.g., at least about 100 nM, usually better than about 30 nM, preferably better than about 10 nM, and more preferably at better than about 3 nM.

The term "polypeptide" or "protein" as used herein includes a significant fragment or segment of a p150, p130, VCP, tsg101, or KWC02 protein, and encompasses a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids, e.g., 35, 40, 45, 50, 60, 70, 80, etc. The invention encompasses proteins comprising a plurality of said segments. Features of one of the different genes should not be taken to limit those of another of the genes.

A "recombinant" nucleic acid is defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any non-naturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants. "Solubility" is reflected by sedimentation measured in Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.) W.H. Freeman & Co., San Francisco, Calif.; and Cantor and Schimmel (1980) *Biophysical Chemistry* parts 1–3, W.H. Freeman & Co., San Francisco, Calif. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30S, more typically less than about 15S, usually less than about 10S, more usually less than about 6S, and, in particular embodiments, preferably less than about 4S, and more preferably less than about 3S. Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS (cholesteryl hemisuccinate) or CHAPS (3-[3-cholamidopropyl)dimethylammonio]-1-propane sulfonate), or a low enough concentration as to avoid significant disruption of structural or physiological properties of the protein.

"Substantially pure" in a protein context typically means that the protein is isolated from other contaminating proteins, nucleic acids, and other biologicals derived from the original source organism. Purity, or "isolation" may be assayed by standard methods, and will ordinarily be at least about 50% pure, more ordinarily at least about 60% pure, generally at least about 70% pure, more generally at least about 80% pure, often at least about 85% pure, more often at least about 90% pure, preferably at least about 95% pure, more preferably at least about 98% pure, and in most preferred embodiments, at least 99% pure. Similar concepts apply, e.g., to antibodies or nucleic acids.

"Substantial similarity" in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high at about 99% or more of the nucleotides. Alternatively, substantial similarity exists when the segments will hybridize under selective hybridization conditions, to a strand, or its complement, typically using a sequence derived from SEQ ID NO: 1, 3, 5, 7, or 9. Typically, selective hybridization will occur when there is at least about 55% similarity over a stretch of at least about 30 nucleotides, preferably at least about 65% over a stretch of at least about 25 nucleotides, more preferably at least about 75%, and most preferably at least about 90% over about 20 nucleotides. See Kanehisa (1984) *Nuc. Acids Res.* 12:203–213. The length of similarity comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides, e.g., 150, 200, etc.

"Stringent conditions", in referring to homology or substantial similarity in the hybridization context, will be stringent combined conditions of salt, temperature, organic solvents, and other parameters, typically those controlled in hybridization reactions. The combination of parameters is more important than the measure of any single parameter. See, e.g., Wetmur and Davidson (1968) *J. Mol. Biol.* 31:349–370. A nucleic acid probe which binds to a target nucleic acid under stringent conditions is specific for said target nucleic acid. Such a probe is typically more than 11 nucleotides in length, and is sufficiently identical or complementary to a target nucleic acid over the region specified by the sequence of the probe to bind the target under stringent hybridization conditions.

p150, p130, VCP, tsg101, or KWC02 protein from other mammalian species can be cloned and isolated by cross-species hybridization-of closely related species. See, e.g., below. Similarity may be relatively low between distantly related species, and thus hybridization of relatively closely related species is advisable. Alternatively, preparation of an antibody preparation which exhibits less species specificity may be useful in expression cloning approaches.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified antibodies bind to a particular protein and do not significantly bind other proteins present in the sample. Specific binding to an antibody under such conditions may require an antibody that is selected for its specificity for a particular protein. For example, antibodies raised to the human protein immunogen with the amino acid sequence depicted in SEQ ID NO: 2, 4, 6, 8, or 10 can be selected to obtain antibodies specifically immunoreactive with p150, p130, VCP, tsg101, or KWC02 proteins and not with other proteins. These antibodies recognize proteins highly similar to the homologous p150, p130, VCP, tsg101, or KWC02 protein.

III. Nucleic Acids

Human p150, p130, VCP, tsg101, or KWC02 protein is each exemplary of a larger class of structurally and functionally related proteins. These soluble proteins will serve to transmit signals between different cell types. The preferred embodiments, as disclosed, will be useful in standard procedures to isolate genes from different individuals or other species, e.g., warm blooded animals, such as birds and mammals. Cross hybridization will allow isolation of related genes encoding proteins from individuals, strains, or species. A number of different approaches are available to successfully isolate a suitable nucleic acid clone based upon the information provided herein. Southern blot hybridization studies can qualitatively determine the presence of homologous genes in human, monkey, rat, mouse, dog, cow, and rabbit genomes under specific hybridization conditions.

Complementary sequences will also be used as probes or primers. Based upon identification of the likely amino terminus, other peptides should be particularly useful, e.g., coupled with anchored vector or poly-A complementary PCR techniques or with complementary DNA of other peptides.

Techniques for nucleic acid manipulation of genes encoding p150, p130, VCP, tsg101, or KWC02 proteins, such as subcloning nucleic acid sequences encoding polypeptides into expression vectors, labeling probes, DNA hybridization, and the like are described generally in Sambrook, et al. (1989) *Molecular Cloning: A Laboratory Manual* (2nd ed.) Vol. 1–3, Cold Spring Harbor Laboratory, Cold Spring Harbor Press, NY, which is incorporated herein by reference. This manual is hereinafter referred to as "Sambrook, et al."

There are various methods of isolating DNA sequences encoding p150, p130, VCP, tsg101, or KWC02 proteins. For example, DNA is isolated from a genomic or cDNA library using labeled oligonucleotide probes having sequences identical or complementary to the sequences disclosed herein. Full-length probes may be used, or oligonucleotide probes may be generated by comparison of the sequences disclosed. Such probes can be used directly in hybridization assays to isolate DNA encoding p150, p130, VCP, tsg101, or KWC02 proteins, or probes can be designed for use in amplification techniques such as PCR, for the isolation of DNA encoding p150, p130, VCP, tsg101, or KWC02 proteins.

To prepare a cDNA library, mRNA is isolated from cells which expresses a p150, p130, VCP, tsg101, or KWC02 protein. cDNA is prepared from the mRNA and ligated into a recombinant vector. The vector is transfected into a recombinant host for propagation, screening, and cloning. Methods for making and screening cDNA libraries are well known. See Gubler and Hoffman (1983) *Gene* 25:263–269 and Sambrook, et al.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described in Sambrook, et al. Recombinant phage are analyzed by plaque hybridization as described in Benton and Davis (1977) *Science* 196:180–182. Colony hybridization is carried out as generally described in e.g., Grunstein, et al. (1975) *Proc. Natl. Acad. Sci. USA*. 72:3961–3965.

DNA encoding a p150, p130, VCP, tsg101, or KWC02 protein can be identified in either cDNA or genomic libraries by its ability to hybridize with the nucleic acid probes described herein, e.g., in colony or plaque hybridization assays. The corresponding DNA regions are isolated by standard methods familiar to those of skill in the art. See, e.g., Sambrook, et al.

Various methods of amplifying target sequences, such as the polymerase chain reaction, can also be used to prepare DNA encoding p150, p130, VCP, tsg101, or KWC02 proteins. Polymerase chain reaction (PCR) technology is used to amplify such nucleic acid sequences directly from MRNA, from cDNA, and from genomic libraries or cDNA libraries. The isolated sequences encoding p150, p130, VCP, tsg101, or KWC02 proteins may also be used as templates for PCR amplification.

Typically, in PCR techniques, oligonucleotide primers complementary to two 5' regions in the DNA region to be amplified are synthesized. The polymerase chain reaction is then carried out using the two primers. See Innis, et al. (eds.) (1990) *PCR Protocols: A Guide to Methods and Applications* Academic Press, San Diego, Calif. Primers can be selected to amplify the entire regions encoding a full-length p150, p130, VCP, tsg101, or KWC02 protein or to amplify smaller DNA segments as desired. Once such regions are PCR-amplified, they can be sequenced and oligonucleotide probes can be prepared from sequence obtained using standard techniques. These probes can then be used to isolate DNA's encoding p150,. p130, VCP, tsg101, or KWC02 proteins.

Oligonucleotides for use as probes are usually chemically synthesized according to the solid phase phosphoramidite triester method first described by Beaucage and Carruthers (1983) *Tetrahedron Lett*. 22(20):1859–1862, or using an automated synthesizer, as described in Needham-VanDevanter, et al. (1984) *Nucleic Acids Res*. 12:6159–6168. Purification of oligonucleotides is performed e.g., by native acrylamide gel electrophoresis or by anion-exchange HPLC as described in Pearson and Regnier (1983) *J. Chrom*. 255:137–149. The sequence of the synthetic oligonucleotide can be verified using, e.g., the chemical degradation method of Maxam, A. M. and Gilbert, W. in Grossman, L. and Moldave (eds.) (1980) *Methods in Enzymology* 65:499–560 Academic Press, New York.

An isolated nucleic acid encoding a human p150, p130, VCP, tsg101, or KWC02 protein was identified. The nucleotide sequence and corresponding open reading frame are provided in SEQ ID NO: 1 through 8; with further sequences provided in SEQ ID NO: 9 and 10.

These p150, p130, VCP, tsg101, or KWC02 proteins exhibit limited similarity to portions other cyclin associated proteins or transcription factors. In particular, β-sheet and α-helix residues can be determined using, e.g., RASMOL program, see Sayle and Milner-White (1995) *TIBS* 20:374–376; or Gronenberg, et al. (1991) *Protein Engineering* 4:263–269; and other structural features are defined in Lodi, et al. (1994) *Science* 263:1762–1767.

This invention provides isolated DNA or fragments to encode a p150, p130, VCP, tsg101, or KWC02 protein. In addition, this invention provides isolated or recombinant DNA which encodes a protein or polypeptide which is capable of hybridizing under appropriate conditions, e.g., high stringency, with the DNA sequences described herein. Said biologically active protein or polypeptide can be an intact protein, or fragment, and have an amino acid sequence as disclosed in SEQ ID NO: 2, 4, 6, 8, or 10 particularly natural embodiments. Preferred embodiments will be full length natural sequences. Further, this invention contemplates the use of isolated or recombinant DNA, or fragments thereof, which encode proteins which are homologous to a p150, p130, VCP, tsg101, or KWC02 protein or which were isolated using cDNA encoding a p150, p130, VCP, tsg101, or KWC02 protein as a probe. The isolated DNA can have the respective regulatory sequences in the 5' and 3' flanks, e.g., promoters, enhancers, poly-A addition signals, and others. Also embraced are methods for making expression vectors with these sequences, or for making, e.g., expressing and purifying, protein products.

A DNA which codes for a p150, p130, VCP, tsg101, or KWC02 protein will be particularly useful to identify genes, mRNA, and cDNA species which code for related or similar proteins, as well as DNAs which code for homologous proteins from different species. There are likely homologs in other species, including primates, rodents, canines, felines, and birds. Various p150, p130, VCP, tsg101, or KWC02 proteins should be homologous and are encompassed herein. However, even proteins that have a more distant evolutionary relationship to the antigen can readily be isolated under appropriate conditions using these sequences if they are sufficiently homologous. Primate p150, p130, VCP, tsg101, or KWC02 proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Inmunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach*, IRL Press, Oxford; and Rosenberg (1992) *J. Clinical Oncology* 10:180–199.

V. Antibodies

Antibodies can be raised to various p150, p130, VCP, tsg101, or KWC02 proteins, including individual, polymorphic, allelic, strain, or species variants, and fragments thereof, both in their naturally occurring (full-length) forms and in their recombinant forms. Additionally, antibodies can be raised to p150, p130, VCP, tsg101, or KWC02 proteins in either their active forms or in their inactive forms. Anti-idiotypic antibodies may also be used.

A. Antibody Production

A number of immunogens may be used to produce antibodies specifically reactive with p150, p130, VCP, tsg101, or KWC02 proteins. Recombinant protein is the preferred immunogen for the production of monoclonal or polyclonal antibodies. Naturally occurring protein may also be used either in pure or impure form. Synthetic peptides, made using the human p150, p130, VCP, tsg101, or KWC02 protein sequences described herein, may also used as an inmunogen for the production of antibodies to p150, p130, VCP, tsg101, or KWC02 proteins. Recombinant protein can be expressed in eukaryotic or prokaryotic cells as described herein, and purified as described. Naturally folded or denatured material can be used, as appropriate, for producing antibodies. Either monoclonal or polyclonal antibodies may be generated for subsequent use in imnmunoassays to measure the protein.

Methods of producing polyclonal antibodies are known to those of skill in the art. Typically, an immunogen, preferably a purified protein, is mixed with an adjuvant and animals are immunized with the mixture. The animal's immune response to the immunogen preparation is monitored by taking test bleeds and determining the titer of reactivity to the p150, p130, VCP, tsg101, or KWC02 protein of interest. When appropriately high titers of antibody to the immunogen are obtained, usually after repeated immunizations, blood is collected from the animal and antisera are prepared. Further fractionation of the antisera to enrich for antibodies reactive to the protein can be done if desired. See, e.g., Harlow and Lane; or Coligan.

Monoclonal antibodies may be obtained by various techniques familiar to those skilled in the art. Typically, spleen cells from an animal immunized with a desired antigen are immortalized, commonly by fusion with a myeloma cell (see, Kohler and Milstein (1976) *Eur. J. Immunol.* 6:511–519, incorporated herein by reference). Alternative methods of immortalization include transformation with Epstein Barr Virus, oncogenes, or retroviruses, or other methods known in the art. Colonies arising from single inmortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according, e.g., to the general protocol outlined by Huse, et al. (1989) *Science* 246:1275–1281.

Antibodies, including binding fragments and single chain versions, against predetermined fragments of p150, p130, VCP, tsg101, or KWC02 protein can be raised by immunization of animals with conjugates of the fragments with carrier proteins as described above. Monoclonal antibodies are prepared from cells secreting the desired antibody. These antibodies can be screened for binding to normal or defective p150, p130, VCP, tsg101, or KWC02 proteins, or screened for agonistic or antagonistic activity, e.g., effect on cell cycle progression or transcription of specific genes. These monoclonal antibodies will usually bind with at least a $K_D$ of about 1 mM, more usually at least about 300 $\mu$M, typically at least about 10 $\mu$M, more typically at least about 30 $\mu$M, preferably at least about 10 $\mu$M, and more preferably at least about 3 $\mu$M or better.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.) Lange Medical Publications, Los Altos, Calif., and references cited therein; Harlow and Lane (1988) *Antibodies: A Laboratory Manual* CSH Press; Goding (1986) *Monoclonal Antibodies: Principles and Practice* (2d ed.) Academic Press, New York, N.Y.; and particularly in Kohler and Milstein (1975) *Nature* 256:495–497, which discusses one method of generating monoclonal antibodies. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, e.g., Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced. See, Cabilly, U.S. Pat. No. 4,816,567; and Queen, et al. (1989) *Proc. Nat'l Acad. Sci. USA* 86:10029–10033.

The antibodies of this invention are useful for affinity chromatography in isolating p150, p130, VCP, tsg101, or KWC02 protein. Columns can be prepared where the antibodies are linked to a solid support, e.g., particles, such as agarose, SEPHADEX, or the like, where a cell lysate or supernatant may be passed through the column, the column washed, followed by increasing concentrations of a mild denaturant, whereby purified p150, p130, VCP, tsg101, or KWC02 protein will be released.

The antibodies may also be used to screen expression libraries for particular expression products. Usually the antibodies used in such a procedure will be labeled with a moiety allowing easy detection of presence of antigen by antibody binding.

Antibodies to p150, p130, VCP, tsg101, or KWC02 proteins may be used for the identification of cell populations expressing p150, p130, VCP, tsg101, or KWC02 proteins. By assaying, e.g., by histology or otherwise, probably a destructive assay which kills that sample of cells, the expression products of cells expressing p150, p130, VCP, tsg101, or KWC02 proteins it is possible to diagnose disease, e.g., cancerous conditions.

Antibodies raised against each p150, p130, VCP, tsg101, or KWC02 protein will also be useful to raise anti-idiotypic antibodies. These will be useful in detecting or diagnosing various immunological conditions related to expression of the respective antigens.

B. Immunoassays

A particular protein can be measured by a variety of immunoassay methods. For a review of immnological and immunoassay procedures in general, see Stites and Terr (eds.) (1991) *Basic and Clinical Immunology* (7th ed.). Moreover, the immunoassays of the present invention can be performed in many configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; and Harlow and Lane *Antibodies, A Laboratory Manual*, supra, each of which is incorporated herein by reference. See also Chan (ed.) (1987) *Immunoassay: A Practical Guide* Academic Press, Orlando, Fla.; Price and Newman (eds.) (1991) *Principles and Practice of Immunoassays* Stockton Press, NY; and Ngo (ed.) (1988) *Non-isotopic Immunoassays* Plenum Press, NY.

Immunoassays for measurement of p150, p130, VCP, tsg101, or KWC02 proteins can be performed by a variety of methods known to those skilled in the art. In brief, immunoassays to measure the protein can be either competitive or noncompetitive binding assays. In competitive binding assays, the sample to be analyzed competes with a labeled analyte for specific binding sites on a capture agent bound to a solid surface. Preferably the capture agent is an antibody specifically reactive with p150, p130, VCP, tsg101, or KWC02 proteins produced as described above. The concentration of labeled analyte bound to the capture agent is inversely proportional to the amount of free analyte present in the sample.

In a competitive binding immunoassay, the p150, p130, VCP, tsg101, or KWC02 protein present in the sample competes with labeled protein for binding to a specific binding agent, for example, an antibody specifically reactive with the p150, p130, VCP, tsg101, or KWC02 protein. The binding agent may be bound to a solid surface to effect separation of bound labeled protein from the unbound labeled protein. Alternately, the competitive binding assay may be conducted in liquid phase and a variety of techniques known in the art may be used to separate the bound labeled protein from the unbound labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the inmunoassay allows for detection or quantitation of the protein.

p150, p130, VCP, tsg101, or KWC02 proteins may also be determined by a variety of noncompetitive immunoassay methods. For example, a two-site, solid phase sandwich immunoassay may be used. In this type of assay, a binding agent for the protein, for example an antibody, is attached to a solid support. A second protein binding agent, which may also be an antibody, and which binds the protein at a different site, is labeled. After binding at both sites on the protein has occurred, the unbound labeled binding agent is removed and the amount of labeled binding agent bound to the solid phase is measured. The amount of labeled binding agent bound is directly proportional to the amount of protein in the sample.

Western blot analysis can be used to determine the presence of p150, p130, VCP, tsg101, or KWC02 proteins in a sample. Electrophoresis is carried out, for example, on a tissue sample suspected of containing the protein. Following electrophoresis to separate the proteins, and transfer of the proteins to a suitable solid support, e.g., a nitrocellulose filter, the solid support is incubated with an antibody reactive with the protein. This antibody may be labeled, or alternatively may be detected by subsequent incubation with a second labeled antibody that binds the primary antibody.

The immunoassay formats described above employ labeled assay components. The label may be coupled directly or indirectly to the desired component of the assay according to methods well known in the art. A wide variety of labels and methods may be used. Traditionally, a radioactive label incorporating $^3$H, $^{125}$I, $^{35}$S, $^{14}$C, or $^{32}$P was used. Non-radioactive labels include proteins which bind to labeled antibodies, fluorophores, chemiluminescent agents, enzymes, and antibodies which can serve as specific binding pair members for a labeled protein. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference.

Antibodies reactive with a particular protein can also be measured by a variety of immunoassay methods. For a review of immunological and immunoassay procedures applicable to the measurement of antibodies by immunoassay techniques, see Stites and Terr (eds.) *Basic and Clinical Immunology* (7th ed.) supra; Maggio (ed.) *Enzyme Immunoassay*, supra; and Harlow and Lane *Antibodies. A Laboratory Manual*, supra.

In brief, immunoassays to measure antisera reactive with p150, p130, VCP, tsg101, or KWC02 proteins can be either competitive or noncompetitive binding assays. In competitive binding assays, the sample analyte competes with a labeled analyte for specific binding sites on a capture agent bound to a solid surface. Preferably the capture agent is a purified recombinant p150, p130, VCP, tsg101, or KWC02 protein produced as described above. Other sources of p150, p130, VCP, tsg101, or KWC02 proteins, including isolated or partially purified naturally occurring protein, may also be used. Noncompetitive assays include sandwich assays, in which the sample analyte is bound between two analyte-specific binding reagents. One of the binding agents is used as a capture agent and is bound to a solid surface. The second binding agent is labeled and is used to measure or detect the resultant complex by visual or instrument means. A number of combinations of capture agent and labeled binding agent can be used. A variety of different immunoassay formats, separation techniques, and labels can be also be used similar to those described above for the measurement of p150, p130, VCP, tsg101, or KWC02 proteins.

V. Making p150, p130, VCP, tsg101, or KWC02 proteins; Mimetics

DNAs which encode a p150, p130, VCP, tsg101, or KWC02 protein or fragments thereof can be obtained by chemical synthesis, screening cDNA libraries, or by screening genomic libraries prepared from a wide variety of cell lines or tissue samples. Methods for doing so, or making expression vectors are described herein.

These DNAs can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies. Each p150, p130, VCP, tsg101, or KWC02 protein or its fragments can be expressed in host cells that are transformed or transfected with appropriate expression vectors. These molecules can be substantially purified to be free of protein or cellular contaminants, other than those derived from the recombinant host, and therefore are particularly useful in pharmaceutical compositions when combined with a pharmaceutically acceptable carrier and/or diluent. The antigen, e.g., p150, p130, VCP, tsg101, or KWC02 protein, or portions thereof, may be expressed as fusions with other proteins or possessing an epitope tag.

Expression vectors are typically self-replicating DNA or RNA constructs containing the desired antigen gene or its fragments, usually operably linked to appropriate genetic control elements that are recognized in a suitable host cell. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently from the host cell.

The vectors of this invention contain DNAs which encode a p150, p130, VCP, tsg101, or KWC02 protein, or a fragment thereof, typically encoding, e.g., a biologically active polypeptide, or protein. The DNA can be under the control of a viral promoter and can encode a selection marker. This invention further contemplates use of such expression vectors which are capable of expressing eukaryotic cDNA coding for a p150, p130, VCP, tsg101, or KWC02 protein in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of a p150, p130, VCP, tsg101, or KWC02 protein gene or its fragments into the host DNA by recombination, or to integrate a promoter which controls expression of an endogenous gene. vectors, as used herein, contemplate plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector, but many other forms of vectors which serve an equivalent function are suitable for use herein. See, e.g., Pouwels, et al. (1985 and Supplements) *Cloning Vectors: A Laboratory Manual* Elsevier, N.Y.; and Rodriquez, et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and Pichia, and species of the genus Dictyostelium. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express p150, p130, VCP, tsg101, or KWC02 proteins or 6p150, p130, VCP, tsg101, or KWC02 protein fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in Rodriguez and Denhardt (eds.) *Vectors: A Survey of Molecular Cloning Vectors and Their Uses* 10:205–236 Buttersworth, Boston, Mass.

Lower eukaryotes, e.g., yeasts and Dictyostelium, may be transformed with p150, p130, VCP, tsg101, or KWC02 protein sequence containing vectors. For purposes of this invention, the most common lower eukaryotic host is the baker's yeast, *Saccharomyces cerevisiae*. It will be used generically to represent lower eukaryotes although a number of other strains and species are also available. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are typically the preferred host cells for expression of the functionally active p150, p130, VCP, tsg101, or KWC02 protein. In principle, many higher eukaryotic tissue culture cell lines may be used, e.g., insect baculovirus expression systems, whether from an invertebrate or vertebrate source. However, mammalian cells are preferred to achieve proper processing, both cotranslationally and posttranslationally. Transformation or transfection and propagation of such cells is routine. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610.

It is likely that p150, p130, VCP, tsg101, or KWC02 proteins need not be glycosylated to elicit biological responses. However, it will occasionally be desirable to express a p150, p130, VCP, tsg101, or KWC02 protein polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, the p150, p130, VCP, tsg101, or KWC02 protein gene may be co-transformed with one or more genes encoding mammalian or other glycosylating enzymes. It is further understood that over glycosylation may be detrimental to p150, p130, VCP, tsg101, or KWC02 protein biological activity, and that one of skill may perform routine testing to optimize the degree of glycosylation which confers optimal biological activity.

A p150, p130, VCP, tsg101, or KWC02 protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochem. Biophys. Acta* 988:427–454; Tse, et al. (1985) *Science* 230:1003–1008; and Brunner, et al. (1991) *J. Cell Biol.* 114:1275–1283.

Now that p150, p130, VCP, tsg101, or KWC02 proteins have been characterized, fragments or derivatives thereof can be prepared by conventional processes for synthesizing peptides. These include processes such as are described in Stewart and Young (1984) *Solid Phase Peptide Synthesis* Pierce Chemical Co., Rockford, Ill.; Bodanszky and Bodanszky (1984) *The Practice of Peptide Synthesis* Springer-Verlag, New York, N.Y.; and Bodanszky (1984) *The Principles of Peptide Synthesis* Springer-Verlag, New York, N.Y. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. The p150, p130, VCP, tsg101, or KWC02 proteins of this invention can be obtained in varying degrees of purity depending upon its desired use. Purification can be accomplished by use of known protein purification techniques or by the use of the antibodies or binding partners herein described, e.g., in immunoabsorbant affinity chromatography. This immunoabsorbant affinity chromatography is carried out by first linking the antibodies to a solid support and then contacting the linked antibodies with solubilized lysates of appropriate source cells, lysates of other cells expressing the protein, or lysates or supernatants of cells producing the p150, p130, VCP, tsg101, or KWC02 proteins as a result of recombinant DNA techniques, see below.

Multiple cell lines may be screened for one which expresses a p150, p130, VCP, tsg101, or KWC02 protein at a high level compared with other cells. Various cell lines, e.g., a mouse thymic stromal cell line TA4, is screened and selected for its favorable handling properties. Natural p150, p130, VCP, tsg101, or KWC02 proteins can be isolated from natural sources, or by expression from a transformed cell using an appropriate expression vector. Purification of the expressed protein is achieved by standard procedures, or may be combined with engineered means for effective purification at high efficiency from cell lysates or supernatants. Epitope or other tags, e.g., FLAG or $His_6$ segments, can be used for such purification features.

VI. Physical Variants

This invention also encompasses proteins or peptides having substantial amino acid sequence similarity with an amino acid sequence of a p150, p130, VCP, tsg101, or KWC02 protein. Natural variants include individual, polymorphic, allelic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural polymorphic, allelic, and interspecies variations in each respective protein sequence. Typical homologous proteins or peptides will have from 50–100% similarity (if gaps can be introduced), to 75–100% similarity (if conservative substitutions are included) over fixed stretches of amino acids with the amino acid sequence of the p150, p130, VCP, tsg101, or KWC02 protein. Similarity measures will be at least about 50%, generally at least 65%, usually at least 70%, preferably at least 75%, and more preferably at least 90%, and in particularly preferred embodiments, at least 96% or more. See also Needleham, et al. (1970) *J. Mol. Biol.* 48:443–453; Sankoff, et al. (1983) *Time Warps, String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group, Madison, Wis. Stretches of amino acids will be at least about 10 amino acids, usually about 20 amino acids, usually 50 amino acids, preferably 75 amino acids, and in particularly preferred embodiments at least about 100 amino acids. Identity can also be measures over amino acid stretches of about 98, 99, 110, 120, 130, etc.

Nucleic acids encoding mammalian p150, p130, VCP, tsg101, or KWC02 proteins will typically hybridize to the nucleic acid sequence of SEQ ID NO: 1, 3, 5, 7 or 9 under stringent conditions. For example, nucleic acids encoding human p150, p130, VCP, tsg101, or KWC02 proteins will normally hybridize to the nucleic acid of SEQ ID NO: 1, 3, 5, 7, or 9 under stringent hybridization conditions. Generally, stringent conditions are selected to be about 10° C. lower than the thermal melting point (Tm) for the probe sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.2 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids which will bind to disclosed sequences in 50% formamide and 200 mM NaCl at 42° C.

An isolated p150, p130, VCP, tsg101, or KWC02 protein DNA can be readily modified by nucleotide substitutions, nucleotide deletions, nucleotide insertions, and short inversions of nucleotide stretches. These modifications result in novel DNA sequences which encode p150, p130, VCP, tsg101, or KWC02 protein antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant p150, p130, VCP, tsg101, or KWC02 protein derivatives include predetermined or site-specific mutations of the respective protein or its fragments. "Mutant p150, p130, VCP, tsg101, or KWC02 protein" encompasses a polypeptide otherwise falling within the homology definition of the human p150, p130, VCP, tsg101, or KWC02 protein as set forth above, but having an amino acid sequence which differs from that of a p150, p130, VCP, tsg101, or KWC02 protein as found in nature, whether by way of deletion, substitution, or insertion. In particular, "site specific mutant p150, p130, VCP, tsg101, or KWC02 protein" generally includes proteins having significant similarity with a protein having a sequence of SEQ ID NO: 2, 4, 6, 8 or 10, e.g., natural embodiments, and as sharing various biological activities, e.g., antigenic or immunogenic, with those sequences, and in preferred embodiments contain most or all of the disclosed sequence. This applies also to polymorphic variants from different individuals. Similar concepts apply to different p150, p130, VCP, tsg101, or KWC02 proteins, particularly those found in various warm blooded animals, e.g., mammals and birds. As stated before, it is emphasized that descriptions are generally meant to encompass other p150, p130, VCP, tsg101, or KWC02 proteins, not limited to the human embodiments specifically discussed.

Although site specific mutation sites are predetermined, mutants need not be site specific. p150, p130, VCP, tsg101, or KWC02 protein mutagenesis can be conducted by making amino acid insertions or deletions. Substitutions, deletions, insertions, or any combinations may be generated to arrive at a final construct. Insertions include amino- or carboxyl-terminal fusions, e.g. epitope tags. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See also, Sambrook, et al. (1989) and Ausubel, et al. (1987 and Supplements). The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these proteins. A heterologous fusion protein is a fusion of proteins or segments which are naturally not normally fused in the same manner. Thus, the fusion product of an iinunoglobulin with a p150, p130, VCP, tsg101, or KWC02 protein polypeptide is a continuous protein molecule having sequences fused in a typical peptide linkage, typically made as a single translation product and exhibiting properties derived from each source peptide. A similar concept applies to heterologous nucleic acid sequences.

In addition, new constructs may be made from combining similar functional domains from other proteins. For example, protein-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992. Thus, new chimeric polypeptides exhibiting new combinations of specificities will result from the functional linkage of protein-binding specificities and other functional domains.

VII. Functional Variants

The blocking of physiological response to p150, p130, VCP, tsg101, or KWC02 protein may result from the inhibition of binding of the protein to its binding partner, e.g., through competitive,inhibition. Thus, in vitro assays of the present invention will often use isolated protein, membranes from cells expressing a recombinant membrane associated p150, p130, VCP, tsg101, or KWC02 protein, soluble fragments comprising binding segments of these proteins, or fragments attached to solid phase substrates. These assays will also allow for the diagnostic determination of the effects of either binding segment mutations and modifications, or protein mutations and modifications, e.g., protein analogs. This invention also contemplates the use of competitive drug screening assays, e.g., where neutralizing antibodies to antigen or binding partner fragments compete with a test compound for binding to the protein. In this manner, the antibodies can be used to detect the presence of a polypeptide which shares one or more antigenic binding sites of the protein and can also be used to occupy binding sites on the protein that might otherwise interact with a binding partner.

"Derivatives" of p150, p130, VCP, tsg101, or KWC02 protein antigens include amino acid sequence mutants, glycosylation variants, and covalent or aggregate conjugates with other chemical moieties. Covalent derivatives can be prepared by linkage of functionalities to groups which are found in p150, p130, VCP, tsg101, or KWC02 protein amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents.

A major group of derivatives are covalent conjugates of the p150, p130, VCP, tsg101, or KWC02 protein or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between p150, p130, VCP, tsg101, or KWC02 protein and other homologous or heterologous proteins are also provided. Heterologous polypeptides may be fusions between different surface markers, resulting in, e.g., a hybrid protein exhibiting binding partner specificity. Likewise, heterologous fusions may be constructed which would exhibit a combination of properties or activities of the derivative proteins. Typical examples are fusions of a reporter polypeptide, e.g., luciferase, with a segment or domain of a protein, e.g., a segment involved in binding partner interaction, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) Science 241:812–816. The fusion partner can be constructed such that it can be cleaved off such that a protein of substantially natural length is generated.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity proteins.

This invention also contemplates the use of derivatives of p150, p130, VCP, tsg101, or KWC02 protein other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of proteins or other binding proteins. For example, a p150, p130, VCP, tsg101, or KWC02 protein antigen can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-p150, p130, VCP, tsg101, or KWC02 protein antibodies or its respective binding partner. The p150, p130, VCP, tsg101, or KWC02 protein can also be labeled with a detectable group, e.g., radioiodinated by the chloramine T procedure, covalently bound to rare earth chelates, or conjugated to another fluorescent moiety for use in diagnostic assays. Purification of p150, p130, VCP, tsg101, or KWC02 proteins may be effected by immobilized antibodies or binding partner.

Isolated p150, p130, VCP, tsg101, or KWC02 protein genes will allow transformation of cells lacking expression of corresponding p150, p130, VCP, tsg101, or KWC02 protein, e.g., either species types or cells which lack corresponding proteins and exhibit negative background activity. Expression of transformed genes will allow isolation of antigenically pure cell lines, with defined or single specie variants. This approach will allow for more sensitive detection and discrimination of the physiological effects of p150, p130, VCP, tsg101, or KWC02 binding proteins. Subcellular fragments, e.g., cytoplasts or membrane fragments, can be isolated and used.

VIII. Binding Agent:p150, p130, VCP, tsg101, or KWC02 Protein Complexes

A p150, p130, VCP, tsg101, or KWC02 protein that specifically binds to or that is specifically immnoreactive with an antibody generated against a defined immunogen, such as an immunogen consisting of the amino acid sequence of SEQ ID NO: 2, 3, 4, 6, 8, or 10 is typically determined in an immunoassay. The immunoassay uses a polyclonal antiserum which was raised to a protein of SEQ ID NO: 2, 3, 4, 6, 8 or 10. This antiserum is selected to have low crossreactivity against other intracellular regulatory proteins and any such crossreactivity is removed by immunoabsorption prior to use in the immunoassay.

In order to produce antisera for use in an immunoassay, the protein of SEQ ID NO: 2, 3, 4, 6, or 10 is isolated as described herein. For example, recombinant protein may be produced in a mammalian cell line. An inbred strain of mice such as BALB/c is immunized with the protein of SEQ ID NO: 2, 3, 4, 6, 8, or 10 using a standard adjuvant, such as Freund's adjuvant, and a standard mouse immunization protocol (see Harlow and Lane, supra). Alternatively, a synthetic peptide, preferably near full length, derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other intracellular proteins, using a competitive binding immunoassay such as the one described in Harlow and Lane, supra, at pages 570–573. Preferably two intracellular proteins are used in this determination in conjunction with human p150, p130, VCP, tsg101, or KWC02 protein.

Immunoassays in the competitive binding format can be used for the crossreactivity determinations. For example, a protein of SEQ ID NO: 2, 3, 4, 6, 8, or 10 can be immobilized to a solid support. Proteins added to the assay compete with the binding of the antisera to the immobilized antigen. The ability of the above proteins to compete with the binding of the antisera to the immobilized protein is compared to the protein of SEQ ID NO: 2, 3, 4, 6, 8, or 10. The percent crossreactivity for the above proteins is calculated, using standard calculations. Those antisera with less than 10% crossreactivity with each of the proteins listed above are selected and pooled. The cross-reacting antibodies are then removed from the pooled antisera by imrunoabsorption with the above-listed proteins.

The immunoabsorbed and pooled antisera are then used in a competitive binding immunoassay as described above to compare a second protein to the immunogen protein (e.g., the p150, p130, VCP, tsg101, or KWC02 protein of SEQ ID NO: 2, 3, 4, 6, 8, or 10). In order to make this comparison, the two proteins are each assayed at a wide range of concentrations and the amount of each protein required to inhibit 50% of the binding of the antisera to the immobilized protein is determined. If the amount of the second protein required is less than twice the amount of the protein, e.g., of SEQ ID NO: 2 that is required, then the second protein is said to specifically bind to an antibody generated to the immunogen.

It is understood that each of p150, p130, VCP, tsg101, or KWC02 proteins are members of respective families of homologous proteins that comprise two or more genes. For a particular gene product, such as the human p150, p130, VCP, tsg101, or KWC02 protein, the term refers not only to the amino acid sequences disclosed herein, but also to other proteins that are polymorphic, allelic, non-allelic, or species variants. It is also understood that the term "p150, p130, VCP, tsg101, or KWC02 protein" includes nonnatural mutations introduced by deliberate mutation using conventional recombinant technology such as single site mutation, or by excising short sections of DNA encoding p150, p130, VCP, tsg101, or KWC02 proteins, or by substituting new amino acids, or adding new amino acids. Such minor alterations should substantially maintain the immunoidentity of the original molecule and/or its biological activity. Thus, these alterations include proteins that are specifically immunoreactive with a designated naturally occurring p150, p130, VCP, tsg101, or KWC02 protein, for example, the human p150, p130, VCP, tsg101, or KWC02 protein shown in SEQ ID NO: 2, 3, 4, 6, 8, or 10. The biological properties of the altered proteins can be determined by expressing the protein in an appropriate cell line and measuring, e.g., a proliferative effect. Particular protein modifications considered minor would include conservative substitution of amino acids with similar chemical properties, as described above for the p150, p130, VCP, tsg101, or KWC02 protein as a whole. By aligning a protein optimally with the protein of SEQ ID NO: 2, 3, 4, 6, 8, or 10, and by using the conventional immunoassays described herein to determine immunoidentity, or by using proliferative assays, one can determine the protein compositions of the invention.

IX. Uses

The present invention provides reagents which will find use in diagnostic applications as described elsewhere herein, e.g., in the general description for developmental abnormalities, or below in the description of kits for diagnosis.

p150, p130, VCP, tsg101, or KWC02 nucleotides, e.g., human p150, p130, VCP, tsg101, or KWC02 DNA or RNA, may be used as a component in a forensic assay. For instance, the nucleotide sequences provided may be labeled using, e.g., $^{32}P$ or biotin and used to probe standard restriction fragment polymorphism blots, providing a measurable character to aid in distinguishing between individuals. Such probes may be used in well-known forensic techniques such as genetic fingerprinting. In addition, nucleotide probes made from p150, p130, VCP, tsg101, or KWC02 sequences may be used in in situ assays to detect chromosomal abnormalities. For instance, rearrangements in the human chromosome encoding a p150, p130, VCP, tsg101, or KWC02 gene may be detected via well-known in situ techniques, using p150, p130, VCP, tsg101, or KWC02 probes in conjunction with other known chromosome markers.

Antibodies and other binding agents directed towards p150, p130, VCP, tsg101, or KWC02 proteins or nucleic acids may be used to purify the corresponding p150, p130, VCP, tsg101, or KWC02 molecule. As described in the Examples below, antibody purification of p150, p130, VCP, tsg101, or KWC02 protein components is both possible and practicable. Antibodies and other binding agents may also be used in a diagnostic fashion to determine whether p150, p130, VCP, tsg101, or KWC02 protein components are present in a tissue sample or cell population using well-known techniques described herein. The ability to attach a binding agent to a p150, p130, VCP, tsg101, or KWC02 protein provides a means to diagnose disorders associated with p150, p130, VCP, tsg101, or KWC02 protein misregulation. Antibodies and other p150, p130, VCP, tsg101, or KWC02 protein binding agents may also be useful as histological markers. As described in the examples below, p150, p130, VCP, tsg101, or KWC02 protein expression is limited to specific tissue types. By directing a probe, such as an antibody or nucleic acid to a p150, p130, VCP, tsg101, or KWC02 protein it is possible to use the probe to distinguish tissue and cell types in situ or in vitro.

This invention also provides reagents with significant therapeutic value. The p150, p130, VCP, tsg101, or KWC02 protein (naturally occurring or recombinant), fragments thereof, and antibodies thereto, along with compounds identified as having binding affinity to a p150, p130, VCP, tsg101, or KWC02 protein, are useful in the treatment of conditions associated with abnormal physiology or development, including abnormal proliferation, e.g., cancerous conditions, or degenerative conditions. Abnormal proliferation, regeneration, degeneration, and atrophy may be modulated by appropriate therapeutic treatment using the compositions provided herein. For example, a disease or disorder associated with abnormal expression or abnormal signaling by a p150, p130, VCP, tsg101, or KWC02 protein is a target for an agonist or antagonist of the protein. The proteins likely play a role in regulation or development of neuronal or hematopoietic cells, e.g., lymphoid cells, which affect immunological responses.

Other abnormal developmental conditions are known in cell types shown to possess p150, p130, VCP, tsg101, or KWC02 protein mRNA by northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, NY. Developmental or functional abnormalities, e.g., of the neuronal or immune system, cause significant medical abnormalities and conditions which may be susceptible to prevention or treatment using compositions provided herein.

Recombinant p150, p130, VCP, tsg101, or KWC02 protein or p150, p130, VCP, tsg101, or KWC02 protein antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or fragments thereof can identify compounds having binding affinity to p150, p130, VCP, tsg101, or KWC02 protein, including isolation of associated components. Subsequent biological assays can then be utilized to determine if the compound has intrinsic stimulating activity and is therefore a blocker or antagonist in that it blocks the activity of the protein. Likewise, a compound having intrinsic stimulating activity can activate the binding partner and is thus an agonist in that it simulates the activity of a p150, p130, VCP, tsg101, or KWC02 protein. This invention further contemplates the therapeutic use of antibodies to p150, p130, VCP, tsg101, or KWC02 protein as antagonists. This approach should be particularly useful with other p150, p130, VCP, tsg101 $_1$, or KWC02 protein species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration.

p150, p130, VCP, tsg101, or KWC02 protein, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, N.Y.; Lieberman, et al. (eds.) (1990) *Pharmaceutical Dosage Forms: Tablets* Dekker, N.Y.; and Lieberman, et al. (eds.) (1990) *Pharmaceutical Dosage Forms: Disperse Systems* Dekker, N.Y. The therapy of this invention may be combined with or used in association with other therapeutic agents.

Both the naturally occurring and the recombinant forms of the p150, p130, VCP, tsg101, or KWC02 protein of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, and other descriptions of chemical diversity libraries, which describe means for testing of binding affinity by a plurality of compounds. The development of suitable assays can be greatly facilitated by the availability of large amounts of purified, soluble p150, p130, VCP, tsg101, or KWC02 protein as provided by this invention.

For example, antagonists can normally be found once the protein has been structurally defined. Testing of potential protein analogs is now possible upon the development of highly automated assay methods using a purified binding partner. In particular, new agonists and antagonists will be discovered by using screening techniques described herein. Of particular importance are compounds found to have a combined binding affinity for multiple p150, p130, VCP, tsg101, or KWC02 protein binding components, e.g., compounds which can serve as antagonists for species variants of a p150, p130, VCP, tsg101, or KWC02 protein.

This invention is particularly useful for screening compounds by using recombinant protein in a variety of drug screening techniques. The advantages of using a recombinant protein in screening for specific binding partners include: (a) improved renewable source of the p150, p130, VCP, tsg101, or KWC02 protein from a specific source; (b) potentially greater number of binding partners per cell giving better signal to noise ratio in assays; and (c) species variant specificity (theoretically giving greater biological and disease specificity).

One method of drug screening utilizes eukaryotic or prokaryotic host cells which are stably transformed with recombinant DNA molecules expressing a p150, p130, VCP, tsg101, or KWC02 protein binding counterpart. Cells may be isolated which express a binding counterpart in isolation from any others. Such cells, either in viable or fixed form, can be used for standard protein binding assays. See also, Parce, et al. (1989) *Science* 246:243–247; and Owicki, et al. (1990) *Proc. Nat'l Acad. Sci. USA* 87:4007–4011, which describe sensitive methods to detect cellular responses. Competitive assays are particularly useful, where the cells (source of p150, p130, VCP, tsg101, or KWC02 protein) are contacted and incubated with a labeled binding partner or antibody having known binding affinity to the protein, such as $^{125}$I-antibody, and a test sample whose binding affinity to the binding composition is being measured. The bound and free labeled binding compositions are then separated to assess the degree of protein binding. The amount of test compound bound is inversely proportional to the amount of labeled binding partner binding to the known source. Any one of numerous techniques can be used to separate bound from free protein to assess the degree of protein binding. This separation step could typically involve a procedure such as adhesion to filters followed by washing, adhesion to plastic followed by washing, or centrifugation of the cell membranes. Viable cells could also be used to screen for the effects of drugs on p150, p130, VCP, tsg101, or KWC02 protein mediated functions, e.g., second messenger levels, i.e., cell proliferation; inositol phosphate pool changes, transcription using a luciferase-type assay; and others. Some detection methods allow for elimination of a separation step, e.g., a proximity sensitive detection system.

Another method utilizes membranes from transformed eukaryotic or prokaryotic host cells as the source of a p150, p130, VCP, tsg101, or KWC02 protein. These cells are stably transformed with DNA vectors directing the expression of a p150, p130, VCP, tsg101, or KWC02 protein, e.g., an engineered membrane bound form. Essentially, the membranes would be prepared from the cells and used in a protein binding assay such as the competitive assay set forth above.

Still another approach is to use solubilized, unpurified or solubilized, purified p150, p130, VCP, tsg101, or KWC02 protein from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to a p150, p130, VCP, tsg101 $_1$, or KWC02 protein antibody and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al., supra. Then all the pins are reacted with solubilized, unpurified or solubilized, purified p150, p130, VCP, tsg101, or KWC02 protein antibody, and washed. The next step involves detecting bound p150, p130, VCP, tsg101, or KWC02 protein antibody.

Rational drug design may also be based upon structural studies of the molecular shapes of the p150, p130, VCP, tsg101, or KWC02 protein and other effectors or analogs. See, e.g., *Methods in Enzymology* vols. 202 and 203. Effectors may be other proteins which mediate other functions in response to protein binding, or other proteins which normally interact with the binding partner. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography* Academic Press, NY.

A purified p150, p130, VCP, tsg101, or KWC02 protein can be coated directly onto plates for use in the aforementioned drug screening techniques. However, non-neutralizing antibodies to these proteins can be used as capture antibodies to immobilize the respective protein on the solid phase.

X. Kits

This invention also contemplates use of p150, p130, VCP, tsg101, or KWC02 proteins, fragments thereof, peptides, and their fusion products in a variety of diagnostic kits and methods for detecting the presence of p150, p130, VCP, tsg101, or KWC02 protein or a p150, p130, VCP, tsg101, or KWC02 binding partner. Typically the kit will have a compartment containing either a defined p150, p130, VCP, tsg101, or KWC02 protein peptide or gene segment or a reagent which recognizes one or the other, e.g., binding partner fragments or antibodies.

A kit for determining the binding affinity of a test compound to a p150, p130, VCP, tsg101, or KWC02 protein would typically comprise a test compound; a labeled compound, e.g., a binding agent or antibody having known binding affinity for the p150, p130, VCP, tsg101, or KWC02 protein; a source of p150, p130, VCP, tsg101, or KWC02 protein (naturally occurring or recombinant); and a means for separating bound from free labeled compound, such as a solid phase for immobilizing the p150, p130, VCP, tsg101, or KWC02 protein. Once compounds are screened, those having suitable binding affinity to the p150, p130, VCP, tsg101, or KWC02 protein can be evaluated in suitable biological assays, as are well known in the art, to determine whether they act as agonists or antagonists to the binding partner. The availability of recombinant p150, p130, VCP, tsg101, or KWC02 protein polypeptides also provide well defined standards for calibrating such assays.

A preferred kit for determining the concentration of, for example, a p150, p130, VCP, tsg101, or KWC02 protein in a sample would typically comprise a labeled compound, e.g., binding partner or antibody, having known binding affinity for the p150, p130, VCP, tsg101, or KWC02 protein, a source of p150, p130, VCP, tsg101, or KWC02 protein (naturally occurring or recombinant), and a means for separating the bound from free labeled compound, for example, a solid phase for immobilizing the p150, p130, VCP, tsg101, or KWC02 protein. Compartments containing reagents, and instructions, will normally be provided.

Antibodies, including antigen binding fragments, specific for the p150, p130, VCP, tsg101, or KWC02 protein or fragments thereof are useful in diagnostic applications to detect the presence of elevated levels of p150, p130, VCP, tsg101, or KWC02 protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and antigen-p150, p130, VCP, tsg101, or KWC02 protein complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the antibody to a p150, p130, VCP, tsg101, or KWC02 protein or to a particular fragment thereof. Similar assays have also been extensively discussed in the literature. See, e.g., Harlow and Lane (1988) *Antibodies: A Laboratory Manual*, CSH Press, NY; Chan (ed.) (1987) *Immunoassay: A Practical Guide* Academic Press, Orlando, Fla.; Price and Newman (eds.) (1991) *Principles and Practice of Immunoassay* Stockton Press, NY; and Ngo (ed.) (1988) *Nonisotopic Immunoassay* Plenum Press, NY.

Anti-idiotypic antibodies may have similar use to diagnose presence of antibodies against a p150, p130, VCP, tsg101, or KWC02 protein, as such may be diagnostic of various abnormal states. For example, overproduction of p150, p130, VCP, tsg101, or KWC02 protein may result in production of various immunological or other medical reactions which may be diagnostic of abnormal physiological states, e.g., in cell growth, activation, or differentiation.

Frequently, the reagents for diagnostic assays are supplied in kits, so as to optimize the sensitivity of the assay. For the subject invention, depending upon the nature of the assay, the protocol, and the label, either labeled or unlabeled antibody or binding partner, or labeled p150, p130, VCP, tsg101, or KWC02 protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the drug screening and the diagnostic assays may be used without modification, or may be modified in a variety of ways. For example, labeling may be achieved by covalently or non-covalently joining a moiety which directly or indirectly provides a detectable signal. In any of these assays, the protein, test compound, p150, p130, VCP, tsg101, or KWC02 protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free protein, or alternatively the bound from the free test compound. The p150, p130, VCP, tsg101, or KWC02 protein can be immobilized on various matrices followed by washing. Suitable matrices include plastic such as an ELISA plate, filters, and beads. Methods of immobilizing the p150, p130, VCP, tsg101, or KWC02 protein to a matrix include, without limitation, direct adhesion to plastic, use of a capture antibody, chemical coupling, and biotin-avidin. The last step in this approach involves the precipitation of protein/binding partner or antigen/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a p150, p130, VCP, tsg101, or KWC02 protein. These sequences can be used as probes for detecting levels of the p150, p130, VCP, tsg101, or KWC02 protein message in samples from natural sources, or patients suspected of having an abnormal condition, e.g., cancer or developmental problem. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out using many conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

The broad scope of this invention is best understood with reference to the following examples, which are not intended to limit the invention to specific embodiments.

EXAMPLES

I. General Methods

Many of the standard methods below are described or referenced, e.g., in Maniatis, et al. (1982) *Molecular Cloning, A Laboratory Manual* Cold Spring Harbor Laboratory, Cold Spring Harbor Press, NY; Sambrook, et al. (1989) *Molecular Cloning: A Laboratory Manual* (2d ed.) Vols. 1–3, CSH Press, NY; Ausubel, et al., *Biology* Greene Publishing Associates, Brooklyn, N.Y.; or Ausubel, et al. (1987 and Supplements) *Current Protocols in Molecular Biology* Wiley/Greene, NY; Innis, et al. (eds.) (1990) *PCR Protocols: A Guide to Methods and Applications* Academic Press, NY. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification," *Methods in Enzymology* vol. 182, and other volumes in this series; Coligan, et al. (1995 and supplements) *Current Protocols in Protein Science* John Wiley and Sons, New York, N.Y.; P. Matsudaira (ed.) (1993) *A Practical Guide to Protein and Peptide Purification for Microsequencing*, Academic Press, San Diego, Calif.; and manufacturer's literature on use of protein purification products, e.g., Pharmacia, Piscataway, N.J., or Bio-Rad, Richmond, Calif. Combination with recombinant techniques allow fusion to appropriate segments (epitope tags), e.g., to a FLAG sequence or an equivalent which can be fused, e.g., via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, NY; and Crowe, et al. (1992) *OIAexpress: The High Level Expression & Protein Purification System* QUIAGEN, Inc., Chatsworth, Calif.

Standard immunological techniques are described, e.g., in Hertzenberg, et al. (eds. 1996) *Weir's Handbook of Experimental Immunology* vols. 1–4, Blackwell Science; Coligan (1991 and periodic supplements) *Current Protocols in Immunology* Wiley/Greene, NY; and *Methods in Enzymology* volumes. 70, 73, 74, 84, 92, 93, 108, 116, 121, 132, 150, 162, and 163. Assays for neural cell biological activities are described, e.g., in Wouterlood (ed. 1995) *Neuroscience Protocols* modules 10, Elsevier; *Methods in Neurosciences* Academic Press; and *Neuromethods* Humana Press, Totowa, N.J. Methodology of developmental systems is described, e.g., in Meisami (ed.) *Handbook of Human Growth and Developmental Biology* CRC Press; and Chrispeels (ed.) *Molecular Techniques and Approaches in Developmental Biology* Interscience.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

II. Isolation of Human p150, p130, VCP, tsg101, and KWC02 Clones p150, p130, and VCP were isolated as described above. Briefly, monoclonal antibodies, see, e.g., Lees, et al. (1992) *Genes and Dev.* 6:1874–1885 raised against human cyclin E were used to immunoprecipitate proteins from ML-1 (myeloid leukemia) cells. Proteins that co-immunoprecipitated with cyclin E were visualized by SDS-PAGE, see, e.g., Coligan, et al. (eds.) (1995 and periodic supplements) *Current Protocols in Protein Science*, John Wiley and Sons, New York, N.Y. Proteins of interest were purified in large quantities by affinity purification and subsequently subjected to sequencing by mass spectroscopy.

See, e.g., P. Matsudaira (ed.) (1993) *A Practical Guide to Protein and Peptide Purification for Microsequencing*, Academic Press, San Diego, Calif. Peptide sequences from p150 were used to design degenerate primers, which were used to in low stringency PCR to isolate a 60 bp fragment. This fragment was subsequently used to screen an activated human Inonocyte cDNA library (U937, Bacon and McClanahan, DNAX Research Institute, Palo Alto, Calif.) and isolate a clone of 4.4 kb encoding a protein of about 1107 amino acids and a molecular weight of 123 kD. p130 and VCP peptide sequences were used to carefully screen the available public databases, e.g., Merck-WashU public database (St. Louis, Mo.). Sequence from ESTs identified from these databases were used to screen the U937 library to isolate full length clones. Extension of partial sequences can be routinely completed using methods well known in the art, e.g., from the identified sources.

Human tsg101 was isolated by low-stringency PCR in a peripheral human blood monocyte cDNA library (provided by Bacon and McClanahan, DNAX Research Institute, Palo Alto, Calif.). A 1.5 kb clone encoding about a 391 amino acid protein was subsequently isolated and sequenced. KWC02 was isolated from a subtraction of resting human monocytes library (U937) from human elutriated monocytes stimulated with LPS, IFNγ, and IL-10. See, e.g., See, Figdor, et al. (1982) *Blood* 60:46–53; and Plas, et al. (1988) *Expt'l. Hematol.* 16:355–359. Two classes of full length clones were isolated of 1.7 kb and 1.9 kb. The 1.9 kb clone encodes a predicted protein of about 503 amino acids.

III. Isolation of a Primate p150, p130, VCP, tsg101, or KWC02 Clones

Similar methods are used as above to isolate an appropriate corresponding monkey or other primate gene. Preferably a full length coding sequence is used for hybridization. Similar source materials as indicated above are used to isolate natural genes, including genetic, polymorphic, allelic, or strain variants. Other species variants are also isolated using similar methods. Alternatively, sequence databases may provide useful information, including the possibility of complete sequences.

IV. Isolation of an Avian p150, p130, VCP, tsg101, or KWC02 Clone

An appropriate avian source is selected as above. Similar methods are utilized to isolate a species variant, though the level of similarity will typically be lower for avian protein as compared to a human to mouse sequence.

V. Expression; Purification; Characterization

Proteins of interest are immunoprecipitated and affinity purified as described above, e.g., from a natural or recombinant source.

Alternatively, with an appropriate clone from above, the coding sequence is inserted into an appropriate expression vector. This may be in a vector specifically selected for a prokaryote, yeast, insect, or higher vertebrate, e.g., mammalian expression system. Standard methods are applied to produce the gene product, preferably as a soluble secreted molecule, but will, in certain instances, also be made as an intracellular protein. Intracellular proteins typically require cell lysis to recover the protein, and insoluble inclusion bodies are a common starting material for further purification.

With a clone encoding a vertebrate p150, p130, VCP, tsg101, or KWC02 protein, recombinant production means are used, although natural forms may be purified from appropriate sources. The protein product is purified by standard methods of protein purification, in certain cases, e.g., coupled with immunoaffinity methods. Immunoaffinity methods are used either as a purification step, as described above, or as a detection assay to determine the separation properties of the protein.

Preferably, the protein is secreted into the medium, and the soluble product is purified from the medium in a soluble form. Alternatively, as described above, inclusion bodies from prokaryotic expression systems are a useful source of material. Typically, the insoluble protein is solubilized from the inclusion bodies and refolded using standard methods. Purification methods are developed as described above.

The product of the purification method described above is characterized to determine many structural features. Standard physical methods are applied, e.g., amino acid analysis and protein sequencing. The resulting protein is subjected to CD spectroscopy and other spectroscopic methods, e.g., NMR, ESR, mass spectroscopy, etc. The product is characterized to determine its molecular form and size, e.g., using gel chromatography and similar techniques. Understanding of the chromatographic properties will lead to more gentle or efficient purification methods.

Prediction of glycosylation sites may be made, e.g., as reported in Hansen, et al. (1995) *Biochem. J.* 308:801–813.

The purified protein is also be used to identify other binding partners of P150, P130, VCP, tsg101, or KWC02 as described, e.g., in Fields and Song (1989) *Nature* 340:245–246.

VI. Preparation of Antibodies Against Vertebrate p150, p130, VCP, tsg101, or KWC02

With protein produced, as above, animals are immunized to produce antibodies. Polyclonal antiserum is raised using non-purified antigen, though the resulting serum will exhibit higher background levels. Preferably, the antigen is purified using standard protein purification techniques, including, e.g., affinity chromatography using polyclonal serum indicated above. Presence of specific antibodies is detected using defined synthetic peptide fragments.

Polyclonal serum is raised against a purified antigen, purified as indicated above, or using, e.g., a plurality of, synthetic peptides. A series of overlapping synthetic peptides which encompass all of the full length sequence, if presented to an animal, will produce serum recognizing most linear epitopes on the protein. Such an antiserum is used to affinity purify protein, which is, in turn, used to introduce intact full length protein into another animal to produce another antiserum preparation.

Similar techniques ate used to generate induce monoclonal antibodies to either unpurified antigen, or, preferably, purified antigen.

VII. Cellular and Tissue Distribution

Distribution of the protein or gene products are determined, e.g., using immunohistochemistry with an antibody reagent, as produced above, by Western blotting of cell lysates, or by screening for nucleic acids encoding the respective protein. Either hybridization or PCR methods are used to detect DNA, cDNA, or message content. Histochemistry allows determination of the specific cell types within a tissue which express higher or lower levels of message or DNA. Antibody techniques are useful to quantitate protein in a biological sample, including a liquid or tissue sample. Immunoassays are developed to quantitate protein. Also FACS analysis may be used to evaluate expression in a cell population. Appropriate tissue samples or cell types are isolated and prepared for such detection. Commercial tissue blots are available, e.g., from Clontech (Mountain View, Calif.). Alternatively, cDNA library Southern blots can be analyzed.

VIII. Antagonizing p150, p130, VCP, tsg101, or KWC02 Proteins.

The inhibition of cell cycle progression is especially important for the control of abnormally proliferative diseases, e.g., cancer. Several methods are available to accomplish this control. The ability of cyclin binding is inhibited by the use, e.g., of antibodies raised against the cyclin binding proteins. Other elements include, e.g., peptidomimetics which are peptides designed to mimic the binding site of cyclin associated proteins and disrupt the interaction of these proteins with cyclin. The most effective method to block cell cycle progression is the use of small molecules, e.g., to block the interaction of the associated proteins with cyclin, or to block downstream activity of the associated proteins, as described, e.g., in Hung, et al. (1996) *Chemistry and Biology* 3:623–639. Exposure of a cell to these permeable small molecules should cause a conditional loss of function of the target protein.

Also included in this category is the use of gene therapy to block the expression of the cyclin associated protein or gene transcription factors. Methods of using gene therapy are described, e.g., in Goodnow (1992) "Transgenic Animals" in Roitt (ed.) *Encyclopedia of Immunology*, Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach*, IRL Press, Oxford; and Rosenberg (1992) *J. Clinical Oncology* 10:180–199. Also included is the use of antisense RNA in gene therapy to block expression of the target gene, or proper splicing of gene transcripts.

IX. Induction of JAK/STAT Proteins by KWC02

Because KWC02 Is a homolog of the IRFs, binding of this protein induces the phosphorylation of JAK/STAT proteins, which are found, e.g., associated with the IFNγ and IL-10 receptors. JAK/STATs are necessary for signal transduction. This assay is performed as described, e.g., in Ho, et al. (1995) *Mol. Cell. Biol.* 15:5043–5–53.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated or recombinant polynucleotide encoding a polypeptide comprising the amino acid sequence of SEQ ID NO:4, SEQ ID NO:12, or SEQ ID NO:13.

2. An expression vector comprising the polynucleotide of claim 1.

3. A host cell comprising the expression vector of claim 2.

4. The host cell of claime 3, wherein said host cell is:
   a) a prokaryotic cell; or
   b) a eukaryotic cell.

5. A method of producing a polypeptide of SEQ ID NO:4, SEQ ID NO:12, or SEQ ID NO:13 comprising culturing the host cell of claim 4 under conditions suitable for expression of the polypeptide.

6. The polynucleotide of claim 1, wherein the polynucdeotide is detectably labeled.

7. The polynucleotide of claim 1, wherein the polynucleotide comprises SEQ ID NO:3 or SEQ ID NO:11.

8. The polynucleotide of claim 7, wherein the polynucleotide is detectably labeled.

9. A method of detecting a polynucleotide encoding a polypeptide comprising the amino acid sequence of SEQ ID NO:4, SEQ ID NO:12, or SEQ ID NO:13 comprising:
   a) contacting a sample containing nucleic acids with the polynucleotide of claim 8 under conditions suitable for formation of a duplex; and
   b) detecting the duplex.

* * * * *